(12) United States Patent
Gottschling et al.

(10) Patent No.: US 8,110,575 B2
(45) Date of Patent: Feb. 7, 2012

(54) COMPOUNDS

(75) Inventors: Dirk Gottschling, Mittelbiberach (DE);
Georg Dahmann, Attenweiler (DE);
Henri Doods, Warthausen (DE);
Annekatrin Heimann, Biberach (DE);
Stephan Georg Mueller, Warthausen (DE); Klaus Rudolf, Warthausen (DE);
Gerhard Georg Schaenzle, Warthausen (DE); Dirk Stenkamp, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/743,007

(22) PCT Filed: Nov. 21, 2008

(86) PCT No.: PCT/EP2008/065962
§ 371 (c)(1),
(2), (4) Date: Sep. 13, 2010

(87) PCT Pub. No.: WO2009/065920
PCT Pub. Date: May 28, 2009

(65) Prior Publication Data
US 2011/0021500 A1  Jan. 27, 2011

(30) Foreign Application Priority Data
Nov. 22, 2007  (EP) .................................. 07121350

(51) Int. Cl.
*A01N 43/58* (2006.01)
*A61K 31/50* (2006.01)
*C07D 239/02* (2006.01)

(52) U.S. Cl. ........ 514/247; 544/319; 546/61; 548/301.7; 548/302.1; 548/302.7

(58) Field of Classification Search .................. 514/247; 544/319; 548/301.7, 302.1, 302.7; 546/61
See application file for complete search history.

(56) References Cited

FOREIGN PATENT DOCUMENTS

| WO | 03040128 A1 | 5/2003 |
|---|---|---|
| WO | 2007000340 A2 | 1/2007 |

OTHER PUBLICATIONS

International Search Report, Form PCT/ISA/210, for corresponding PCT/EP2008/065962, Date of mailing Jul. 21, 2009.

*Primary Examiner* — Paul V. Ward
(74) *Attorney, Agent, or Firm* — Michael P. Morris; Alan R. Stempel

(57) ABSTRACT

The present invention relates to new CGRP-antagonists of general formula I

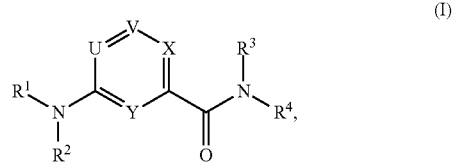

wherein U, V, X, Y, $R^1$, $R^2$, $R^3$ and $R^4$ are defined as in the description, the tautomers, the isomers, the diastereomers, the enantiomers, the hydrates, the mixtures thereof and the salts thereof and the hydrates of the salts, particularly the physiologically acceptable salts thereof with inorganic or organic acids or bases, medicaments containing these compounds, their use and processes for preparing them.

20 Claims, No Drawings

COMPOUNDS

The present invention relates to new CGRP-antagonists of general formula I

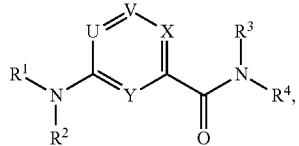

wherein U, V, X, Y, $R^1$, $R^2$, $R^3$ and $R^4$ are defined as stated hereinafter, the tautomers, the isomers, the diastereomers, the enantiomers, the hydrates, the mixtures thereof and the salts thereof and the hydrates of the salts, particularly the physiologically acceptable salts thereof with inorganic or organic acids or bases, medicaments containing these compounds, their use and processes for preparing them.

DETAILED DESCRIPTION OF THE INVENTION

In the above general formula I in a first embodiment
$R^1$ denotes a group of general formulae IIa or IIb

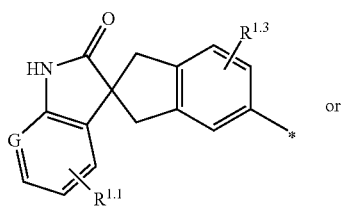

and
$R^2$ denotes H or $C_{1-3}$-alkyl, or
$R^1$ and $R^2$ together with the nitrogen atom to which they are bound denote a group of general formulae IIIa or IIIb

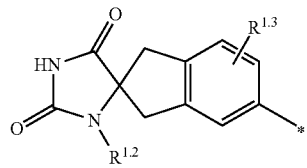

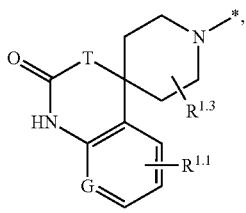

G denotes C—$R^{1.1}$ or N,
T denotes N—$R^{1.2}$ or O,
$R^{1.1}$ independently of one another denote
  (a) H,
  (b) halogen, $C_{1-3}$-alkyl, —OH, —CN, $C_{1-3}$-alkyl-O—, —C(O)—O—$C_{1-3}$-alkyl, $C_{2-4}$-alkenyl, —$C_{2-4}$-alkynyl, $C_{1-3}$-alkyl-S—, cyclopropyl, —$NH_2$, —COOH, —NH—C(O)—O—$C_{1-3}$-alkyl, —NH—C(O)—$C_{1-3}$-alkyl,
  (c) a $C_{1-3}$-alkyl group or $C_{1-3}$-alkyl-O— group, wherein each methylene group is substituted by up to two fluorine atoms and each methyl group is substituted by up to three fluorine atoms,
$R^{1.2}$ independently of one another denote
  (a) H or
  (b) $C_{1-3}$ alkyl,
$R^{1.3}$ denotes
  (a) H,
  (b) F, —CN, $C_{1-3}$-alkyl, —$CO_2$—$R^{1.3.1}$ or
  (c) a $C_{1-3}$-alkyl group, wherein each methylene group may be substituted by up to two fluorine atoms and each methyl group may be substituted by up to three fluorine atoms,
$R^{1.3.1}$ denotes
  (a) H,
  (b) $C_{1-6}$-alkyl,
$R^3$ denotes
  (a) H,
  (b) $C_{1-6}$-alkylene-$R^{3.1}$,
  (c) a $C_{3-6}$-cycloalkyl group substituted by one or two groups $R^{3.2}$,
  (d) a $C_{5-7}$-cycloalkenyl group substituted by one or two groups $R^{3.2}$,
  (e) an aryl group substituted by one or two groups $R^{3.2}$,
  (f) a heterocyclyl group substituted by one or two groups $R^{3.2}$,
  (g) a $C_{5-7}$-cycloalkyl group, which may be fused to an aryl or heteroaryl group and is additionally substituted by one or two groups $R^{3.2}$,
  (h) a heteroaryl group substituted by one or two groups $R^{3.2}$,
  (i) a $C_{1-3}$-alkyl group, wherein each methylene group is substituted by up to two fluorine atoms and each methyl group is substituted by up to three fluorine atoms,
  (j) a dicyclopropylmethyl group,
$R^{3.1}$ denotes
  (a) H,
  (b) an aryl group substituted by the groups $R^{3.1.1}$ and $R^{3.1.2}$,
  (c) a heteroaryl group substituted by the groups $R^{3.1.1}$ and $R^{3.1.2}$,
  (d) a $C_{2-4}$-alkynyl group,
$R^{3.1.1}$ denotes
  (a) H,
  (b) halogen, $C_{1-3}$-alkyl, —OH, —CN, —O—$C_{1-3}$-alkyl, —O—C(O)—$C_{1-3}$-alkyl, —$NR^{3.1.1.1}R^{3.1.1.2}$,

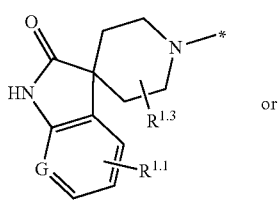

—S(O)$_m$—C$_{1-3}$-alkyl, —NR$^{3.1.1.1}$—C(O)—C$_{1-3}$-alkyl, —C(O)—NR$^{3.1.1.1}$R$^{3.1.1.2}$, —C(O)—O—R$^{3.1.1.3}$, —NR$^{3.1.1.1}$—C(O)—O—C$_{1-3}$-alkyl, —O—C(O)—NR$^{3.1.1.1}$R$^{3.1.1.2}$,
  (c) a C$_{1-3}$-alkyl or —O—C$_{1-3}$-alkyl group, wherein each methylene group is substituted by up to two fluorine atoms and each methyl group is substituted by up to three fluorine atoms,
R$^{3.1.1.1}$ denotes H, C$_{1-3}$-alkyl and
R$^{3.1.1.2}$ denotes H, C$_{1-3}$-alkyl, or
R$^{3.1.1.1}$ and R$^{3.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—C$_{1-3}$-alkyl, —OCF$_3$, C$_{1-3}$-alkyl and CF$_3$,
R$^{3.1.1.3}$ denotes H, C$_{1-3}$-alkyl,
R$^{3.1.2}$ denotes
  (a) H,
  (b) halogen, C$_{1-3}$-alkyl, —OH, —CN, —O—C$_{1-3}$-alkyl,
  (c) a C$_{1-3}$-alkyl- or —O—C$_{1-3}$-alkyl group, wherein each methylene group is substituted by up to two fluorine atoms and each methyl group is substituted by up to three fluorine atoms, or
R$^{3.2}$ independently of one another denote
  (a) H,
  (b) halogen, C$_{1-3}$-alkyl, —OH, —CN, —O—C$_{1-3}$-alkyl, —O—C(O)—C$_{1-3}$-alkyl, —NR$^{3.2.1}$R$^{3.2.2}$, —S(O)$_m$—C$_{1-3}$-alkyl, —NR$^{3.2.1}$—C(O)—C$_{1-3}$-alkyl, —C(O)—NR$^{3.2.1}$R$^{3.2.2}$, —C(O)—O—R$^{3.2.3}$, —NR$^{3.2.1}$—C(O)—O—C$_{1-3}$-alkyl, —O—C(O)—NR$^{3.2.1}$R$^{3.2.2}$,
  (c) a C$_{1-3}$-alkyl- or —O—C$_{1-3}$-alkyl group, wherein each methylene group is substituted by up to two fluorine atoms and each methyl group is substituted by up to three fluorine atoms,
R$^{3.2.1}$ denotes H, C$_{1-3}$-alkyl and
R$^{3.2.2}$ denotes H, C$_{1-3}$-alkyl, or
R$^{3.2.1}$ and R$^{3.2.2}$ together with the nitrogen atom to which they are bound, also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—C$_{1-3}$-alkyl, —OCF$_3$, C$_{1-3}$-alkyl and CF$_3$,
R$^{3.2.3}$ denotes H, C$_{1-3}$-alkyl,
R$^4$ denotes
  (a) H,
  (b) C$_{1-6}$-alkylene-R$^{4.1}$,
  (c) a C$_{3-6}$-cycloalkyl group substituted by one or two groups R$^{4.2}$,
  (d) a C$_{5-7}$-cycloalkenyl group substituted by one or two groups R$^{4.2}$,
  (e) an aryl group substituted by one or two groups R$^{4.2}$,
  (f) a heterocyclyl group substituted by one or two groups R$^{4.2}$,
  (g) a C$_{5-7}$-cycloalkyl group, which may be fused to an aryl or heteroaryl group and is additionally substituted by one or two groups R$^{4.2}$,
  (h) a heteroaryl group substituted by one or two groups R$^{4.2}$,
  (i) a C$_{1-3}$-alkyl group, wherein each methylene group is substituted by up to two fluorine atoms and each methyl group is substituted by up to three fluorine atoms,
  (j) a dicyclopropylmethyl group, R$^{4.1}$ denotes
  (a) H,
  (b) an aryl group substituted by the groups R$^{4.1.1}$ and R$^{4.1.2}$,
  (c) a heteroaryl group substituted by the groups R$^{4.1.1}$ and R$^{4.1.2}$,
  (d) a C$_{2-4}$-alkynyl group,
R$^{4.1.1}$ denotes
  (a) H,
  (b) halogen, C$_{1-3}$-alkyl, —OH, —CN, —O—C$_{1-3}$-alkyl, —O—C(O)—C$_{1-3}$-alkyl, —NR$^{4.1.1.1}$R$^{4.1.1.2}$, —S(O)$_m$—C$_{1-3}$-alkyl, —NR$^{4.1.1.1}$—C(O)—C$_{1-3}$-alkyl, —C(O)—NR$^{4.1.1.1}$R$^{4.1.1.2}$, —C(O)—O—R$^{4.1.1.3}$, —NR$^{4.1.1.1}$—C(O)—O—C$_{1-3}$-alkyl, —O—C(O)—NR$^{4.1.1.1}$R$^{4.1.1.2}$,
  (c) a C$_{1-3}$-alkyl- or —O—C$_{1-3}$-alkyl group, wherein each methylene group is substituted by up to two fluorine atoms and each methyl group is substituted by up to three fluorine atoms,
R$^{4.1.1.1}$ denotes H, C$_{1-3}$-alkyl and
R$^{4.1.1.2}$ denotes H, C$_{1-3}$-alkyl, or
R$^{4.1.1.1}$ and R$^{4.1.1.2}$ together with the nitrogen atom to which they are bound, also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—C$_{1-3}$-alkyl, —OCF$_3$, C$_{1-3}$-alkyl and CF$_3$,
R$^{4.1.1.3}$ denotes H, C$_{1-3}$-alkyl,
R$^{4.1.2}$ denotes
  (a) H,
  (b) halogen, C$_{1-3}$-alkyl, —OH, —CN, —O—C$_{1-3}$-alkyl,
  (c) a C$_{1-3}$-alkyl- or —O—C$_{1-3}$-alkyl group, wherein each methylene group is substituted by up to two fluorine atoms and each methyl group is substituted by up to three fluorine atoms, or
R$^{4.2}$ independently of one another denote
  (a) H,
  (b) halogen, C$_{1-3}$-alkyl, —OH, —CN, —O—C$_{1-3}$-alkyl, —O—C(O)—C$_{1-3}$-alkyl, —NR$^{4.2.1}$R$^{4.2.2}$, —S(O)$_m$—C$_{1-3}$-alkyl, —NR$^{4.2.1}$—C(O)—C$_{1-3}$-alkyl, —C(O)—NR$^{4.2.1}$R$^{4.2.2}$, —C(O)—O—R$^{4.2.3}$, —NR$^{4.2.1}$—C(O)—O—C$_{1-3}$-alkyl, —O—C(O)—NR$^{4.2.1}$R$^{4.2.2}$,
  (c) a C$_{1-3}$-alkyl- or —O—C$_{1-3}$-alkyl group, wherein each methylene group is substituted by up to two fluorine atoms and each methyl group is substituted by up to three fluorine atoms,
R$^{4.2.1}$ denotes H, C$_{1-3}$-alkyl and
R$^{4.2.2}$ denotes H, C$_{1-3}$-alkyl, or
R$^{4.2.1}$ and R$^{4.2.2}$ together with the nitrogen atom to which they are bound, also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—C$_{1-3}$-alkyl, —OCF$_3$, C$_{1-3}$-alkyl and CF$_3$,
R$^{4.2.3}$ denotes H, C$_{1-3}$-alkyl, or
R$^3$ and R$^4$ together with the nitrogen atom to which they are bound denote:
  (a) a saturated 5-, 6-, 7- or 9-membered heterocyclic group, which is substituted at a carbon atom by a group R$^{4.3}$ or by two groups R$^{4.3}$ and R$^{4.4}$,
  (b) a saturated 5-, 6- or 7-membered heterocyclic group, which is substituted at two adjacent carbon atoms by in each case a group R$^{4.3}$ and R$^{4.4}$,
  (c) a saturated 5-, 6- or 7-membered heterocyclic group, which is substituted at a carbon atom by a group R$^{4.3}$ or by two groups R$^{4.3}$ and R$^{4.4}$ and is additionally fused to a 5-, 6- or 7-membered cycloalkyl or heterocyclyl group, wherein the fused-on cycloalkyl or heterocyclyl group is substituted by 1, 2 or 3 groups $R^{4.5}$,
(d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$,
(e) a monounsaturated 5-, 6- or 7-membered heterocyclic group, which is substituted at a carbon atom by a group $R^{4.3}$ or by two groups $R^{4.3}$ and $R^{4.4}$ and additionally is fused to a 5- or 6-membered heteroaryl group, wherein the fused-on heteroaryl group is substituted by 1, 2 or 3 groups $R^{4.5}$, or
(f) a heteroaryl group, which is substituted at 1, 2 or 3 carbon atoms by in each case a group $R^{4.5}$, $R^{4.3}$ independently of one another denote
 (a) H, $C_{1-3}$-alkyl, HO—$C_{1-3}$-alkylene, $C_{2-6}$-alkynyl, aryl, —$C_{1-3}$-alkylene-$R^{4.3.1}$, $C_{1-3}$-alkyl-O—C(O)—, HO—C(O)—, F, —O—$C_{1-3}$-alkyl, —OH, —CN,
 (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N—, $C_{3-6}$-cycloalkyl-, heterocyclyl, heteroaryl, aryl, $R^{4.4}$ denotes
 (a) H, $C_{1-3}$-alkyl, —OH, —O—$C_{1-3}$-alkyl or
 (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound, also denote a $C_{3-6}$-cycloalkyl, $C_{5-6}$-cycloalkenyl or heterocyclyl group, $R^{4.5}$ independently of one another denote
 (a) H,
 (b) halogen, $C_{1-3}$-alkyl, —OH, —O—$C_{1-3}$-alkyl, —S(O)$_m$—$C_{1-3}$-alkyl, —$NR^{4.5.2}R^{4.5.3}$, —CN, —$NO_2$, —C(O)—O—$R^{4.5.1}$, —C(O)—$NR^{4.5.2}R^{4.5.3}$,
 (c) a $C_{1-3}$-alkyl- or —O—$C_{1-3}$-alkyl group, wherein each methylene group is substituted by up to two fluorine atoms and each methyl group is substituted by up to three fluorine atoms,
 (d) aryl, heteroaryl, $R^{4.5.1}$ denotes H, $C_{1-3}$ alkyl,
$R^{4.5.2}$ denotes H, $C_{1-3}$ alkyl,
$R^{4.5.3}$ denotes H, $C_{1-3}$-alkyl, or
$R^{4.5.2}$ and $R^{4.5.3}$ together with the nitrogen atom to which they are bound also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —$OCF_3$, $C_{1-3}$-alkyl and $CF_3$, U denotes N,N-oxide or C—$R^5$,
V denotes N or C—$R^6$,
X denotes N,N-oxide or C—$R^7$,
Y denotes N or C—$R^8$,
 while not more than three of the above-mentioned groups U, V, X and Y simultaneously represent a nitrogen atom,
$R^5$ denotes H, halogen, —CN, $C_{1-3}$-alkyl, —$CF_3$, $C_{2-6}$-alkynyl,
$R^6$ denotes H, $C_{1-3}$-alkyl, —$NR^{6.1}R^{6.2}$ or —O—$C_{1-3}$-alkyl,
$R^{6.1}$ denotes H or $C_{1-6}$-alkyl,
$R^{6.2}$ denotes H or —$SO_2$—$C_{1-3}$-alkyl,
$R^7$ denotes H, halogen, —CN, $C_{1-3}$-alkyl, —$CF_3$, $C_{2-6}$-alkynyl and
$R^8$ denotes H, halogen or $C_{1-3}$-alkyl, the tautomers, the diastereomers, the enantiomers, the hydrates, the mixtures thereof and the salts thereof and the hydrates of the salts, particularly the physiologically acceptable salts thereof with inorganic or organic acids or bases.

A second embodiment of the present invention comprises the compounds of the above general formula I, wherein U, V, X, Y, $R^3$ and $R^4$ are defined as hereinbefore in the first embodiment and $R^1$ denotes a group selected from

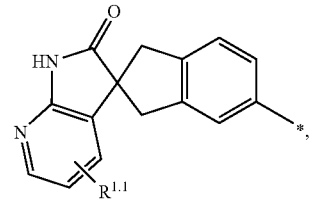

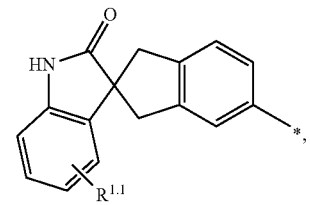

$R^{1.1}$ denotes
 (a) H,
 (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S—, —$NH_2$,
 (c) a $C_{1-3}$-alkyl group or $C_{1-3}$-alkyl-O— group, wherein each methylene group is substituted by up to two fluorine atoms and each methyl group is substituted by up to three fluorine atoms, and $R^{1.2}$ denotes H or $CH_3$ and
$R^2$ denotes H or $C_{1-3}$-alkyl, the tautomers, the diastereomers, the enantiomers, the hydrates, the mixtures thereof and the salts thereof and the hydrates of the salts, particularly the physiologically acceptable salts thereof with inorganic or organic acids or bases.

A third embodiment of the present invention consists in the compounds of the above general formula I, wherein U, V, X, Y, $R^3$ and $R^4$ are defined as hereinbefore in the first embodiment and $R^1$ and $R^2$ together with the nitrogen atom to which they are attached denote a group selected from

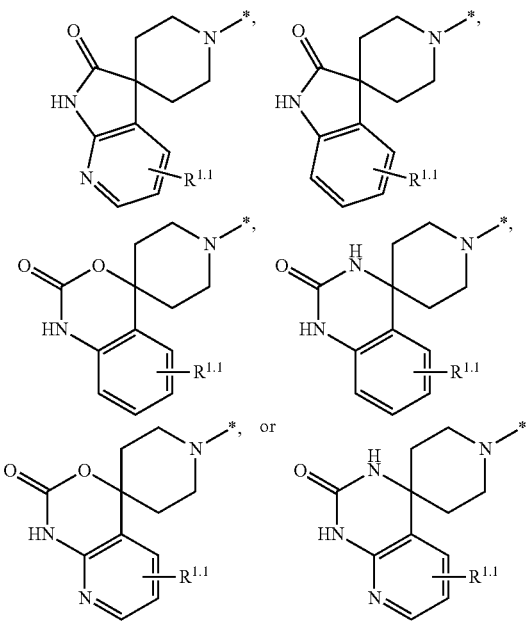

and

R[1.1] denotes (a) H, (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$ alkynyl, $C_{1-3}$-alkyl-S, —$NH_2$, (c) a $C_{1-3}$-alkyl group or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourth embodiment of the present invention consists in the compounds of the above general formula I, wherein U, V, X, Y, $R^3$ and $R^4$ are as hereinbefore defined in the first embodiment and $R^1$ denotes a group selected from

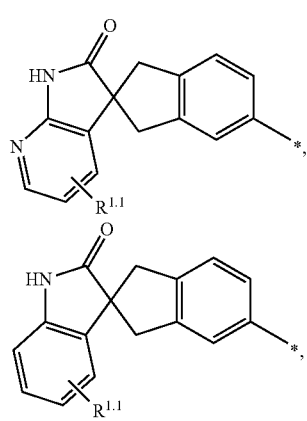

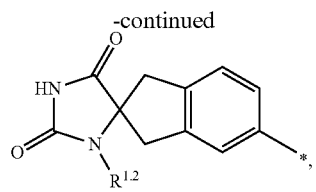

R[1.1] denotes (a) F, $CH_3$, —OH, —O—$CH_3$ or (b) $CF_3$ and $R^2$ denotes H or $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifth embodiment of the present invention consists in the compounds of the above general formula I, wherein U, V, X, Y, $R^3$ and $R^4$ are defined as hereinbefore in the first embodiment and $R^1$ and $R^2$ together with the nitrogen atom to which they are attached denote a group selected from

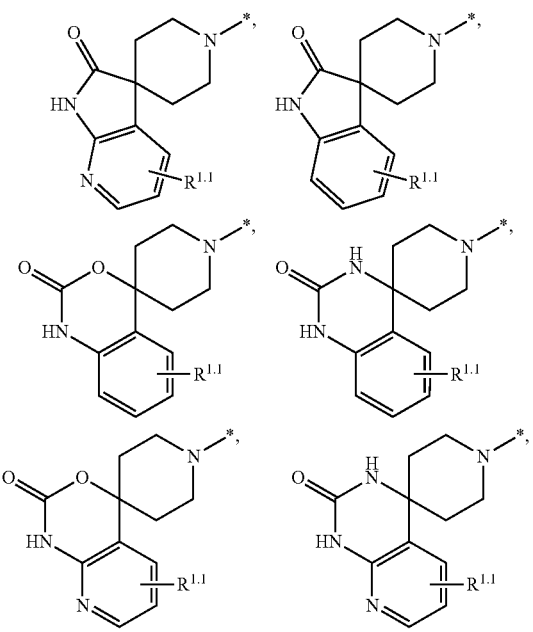

and

R[1.1] denotes (a) F, $CH_3$, —OH, —O—$CH_3$ or (b) $CF_3$, the tautomers, the diastereomers, the enantiomers, the hydrates, the mixtures thereof and the salts thereof as well as the hydrates of the salts, particularly the physiologically acceptable salts thereof with inorganic or organic acids or bases.

A sixth embodiment of the present invention consists in the compounds of the above general formula I, wherein U, V, X, Y, $R^3$ and $R^4$ are as hereinbefore defined in the first embodiment and $R^1$ denotes a group selected from

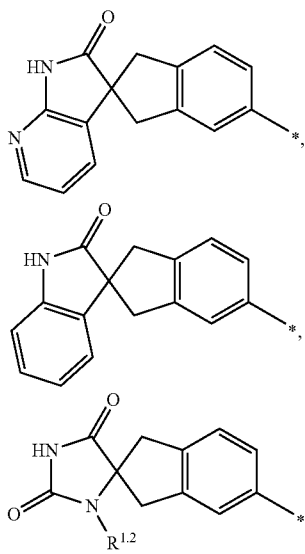

and $R^2$ denotes H, the tautomers, the diastereomers, the enantiomers, the hydrates, the mixtures thereof and the salts thereof as well as the hydrates of the salts, particularly the physiologically acceptable salts thereof with inorganic or organic acids or bases.

A seventh embodiment of the present invention consists in the compounds of the above general formula I, wherein U, V, X, Y, $R^3$ and $R^4$ are defined as hereinbefore in the first embodiment and $R^1$ and $R^2$ together with the nitrogen atom to which they are attached denote a group selected from

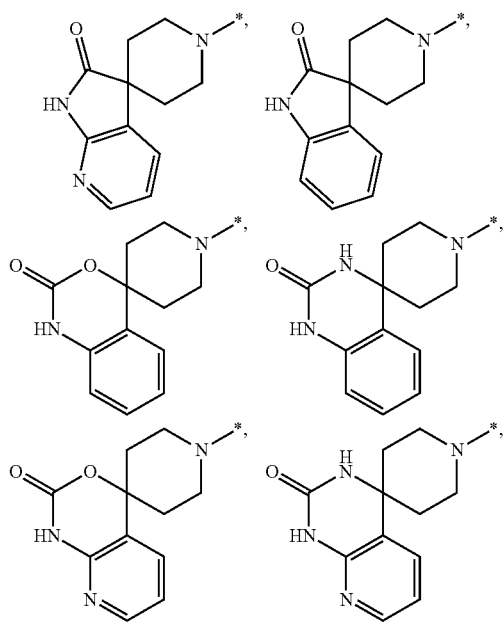

the tautomers, the diastereomers, the enantiomers, the hydrates, the mixtures thereof and the salts thereof as well as the hydrates of the salts, particularly the physiologically acceptable salts thereof with inorganic or organic acids or bases.

An eighth embodiment of the present invention comprises the compounds of the above general formula I, wherein U, V, X, Y, $R^1$ and $R^2$ are as hereinbefore defined in the first, second, fourth or sixth embodiment and $R^3$ denotes
- (a) H,
- (b) $C_{1-6}$-alkyl,
- (c) a $C_{3-6}$-cycloalkyl group substituted by one or two groups $R^{3.2}$,
- (d) a $C_{1-3}$-alkyl group, wherein each methylene group is substituted by up to two fluorine atoms and each methyl group is substituted by up to three fluorine atoms, $R^{3.2}$ independently of one another denote
- (a) H,
- (b) halogen, $C_{1-3}$-alkyl, —OH, —O—$C_{1-3}$-alkyl,
- (c) a $C_{1-3}$-alkyl- or —O—$C_{1-3}$-alkyl group, wherein each methylene group is substituted by up to two fluorine atoms and each methyl group is substituted by up to three fluorine atoms, $R^4$ denotes
- (a) H,
- (b) $C_{1-6}$-alkylene-$R^{4.1}$,
- (c) a $C_{3-6}$-cycloalkyl group substituted by one or two groups $R^{4.2}$,
- (d) a $C_{5-7}$-cycloalkenyl group substituted by one or two groups $R^{4.2}$,
- (e) an aryl group substituted by one or two groups $R^{4.2}$,
- (f) a $C_{5-7}$-cycloalkyl group which may be fused to an aryl group and is additionally substituted by one or two groups $R^{4.2}$, or
- (g) a heteroaryl group substituted by one or two groups $R^{4.2}$, $R^{4.1}$ denotes
- (a) H,
- (b) a phenyl group substituted by the groups $R^{4.1.1}$ and $R^{4.1.2}$,
- (c) a heteroaryl group substituted by the groups $R^{4.1.1}$ and $R^{4.1.2}$,
- (d) a $C_{2-3}$-alkynyl group, $R^{4.1.1}$ denotes
- (a) H,
- (b) halogen, $C_{1-3}$-alkyl, —OH, —CN, —O—$C_{1-3}$-alkyl, —NR$^{4.1.1.1}$R$^{4.1.1.2}$, —S—$C_{1-3}$-alkyl, —NR$^{4.1.1.1}$—C(O)—$C_{1-3}$-alkyl, —C(O)—NR$^{4.1.1.1}$R$^{4.1.1.2}$, —C(O)—O—R$^{4.1.1.3}$,
- (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.1}$ denotes H, $C_{1-3}$-alkyl,
$R^{4.1.1.2}$ denotes H, $C_{1-3}$-alkyl, or
$R^{4.1.1.1}$ and $R^{4.1.1.2}$ together with the nitrogen atom to which they are bound also denote a group selected from morpholinyl, thiomorpholinyl, piperidinyl, piperazinyl, pyrrolidinyl and azetidinyl, $R^{4.1.1.3}$ denotes H, $C_{1-3}$-alkyl, $R^{4.1.2}$ denotes
- (a) H,
- (b) halogen, $C_{1-3}$-alkyl, —OH, —O—$C_{1-3}$-alkyl,
- (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ independently of one another denote
  (a) H,
  (b) halogen, $C_{1-3}$-alkyl, —OH, —CN, —O—$C_{1-3}$-alkyl, —$NR^{4.2.1}R^{4.2.2}$, —S—$C_{1-3}$-alkyl, —$NR^{4.2.1}$—C(O)—$C_{1-3}$-alkyl, —C(O)—$NR^{4.2.1}R^{4.2.2}$, —C(O)—O—$R^{4.2.3}$,
  (c) a $C_{1-3}$-alkyl- or —O—$C_{1-3}$-alkyl group, wherein each methylene group is substituted by up to two fluorine atoms and each methyl group is substituted by up to three fluorine atoms,
$R^{4.2.1}$ denotes H, $C_{1-3}$-alkyl and
$R^{4.2.2}$ denotes H, $C_{1-3}$-alkyl, or
$R^{4.2.1}$ and $R^{4.2.2}$ together with the nitrogen atom to which they are bound also denote a group which is selected from among morpholinyl, thiomorpholinyl, piperidinyl, piperidonyl, piperazinyl, pyrrolidinyl and azetidinyl, and which may additionally be substituted by one or two groups selected from among F, —OH, —O—$C_{1-3}$-alkyl, —OCF$_3$, $C_{1-3}$-alkyl and CF$_3$,
$R^{4.2.3}$ denotes H, $C_{1-3}$-alkyl,
$R^3$ and $R^4$ together with the nitrogen atom to which they are bound denote:
  (a) a saturated 5-, 6-, 7- or 9-membered heterocyclic group, which is substituted at a carbon atom by a group $R^{4.3}$ or by two groups $R^{4.3}$ and $R^{4.4}$,
  (b) a saturated 5-, 6- or 7-membered heterocyclic group, which is substituted at two adjacent carbon atoms by in each case a group $R^{4.3}$ and $R^{4.4}$,
  (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl- or heterocyclyl group, wherein the fused-on cycloalkyl or heterocyclyl group is substituted by 1, 2 or 3 groups $R^{4.5}$,
  (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$,
  (e) a monounsaturated 5-, 6- or 7-membered heterocyclic group, which is substituted at a carbon atom a group $R^{4.3}$ or by two groups $R^{4.3}$ and $R^{4.4}$ and is additionally fused to a 5- or 6-membered heteroaryl group, wherein the fused-on heteroaryl group is substituted by 1, 2 or 3 groups $R^{4.5}$, or
  (f) a heteroaryl group which is substituted by a group $R^{4.5}$ at 1, 2 or 3 carbon atoms,
$R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN,
$R^{4.3.1}$ denotes H, $C_{1-3}$-alkyl-O—C(O)—, —NH$_2$, ($C_{1-4}$-alkyl)-NH—, ($C_{1-4}$-alkyl)$_2$N—, heterocyclyl,
$R^{4.4}$ denotes
  (a) H, $C_{1-3}$-alkyl, —OH, —O—$C_{1-3}$-alkyl or
  (b) a $C_{1-3}$-alkyl- or —O—$C_{1-3}$-alkyl group, wherein each methylene group is substituted by up to two fluorine atoms and each methyl group is substituted by up to three fluorine atoms,
$R^{4.3}$ and $R^{4.4}$ together with the carbon atoms to which they are bound also denote a $C_{3-6}$-cycloalkyl, $C_{5-6}$-cycloalkenyl or heterocyclyl group,
$R^{4.5}$ independently of one another denote
  (a) H,
  (b) halogen, $C_{1-3}$-alkyl, —OH, —O—$C_{1-3}$-alkyl, —NH$_2$, —CN, —C(O)—O—$R^{4.5.1}$, —C(O)—$NR^{4.5.2}R^{4.5.3}$,
  (c) a $C_{1-3}$-alkyl- or —O—$C_{1-3}$-alkyl group, wherein each methylene group is substituted by up to two fluorine atoms and each methyl group is substituted by up to three fluorine atoms,
  (d) phenyl,
$R^{4.5.1}$ denotes H, $C_{1-3}$-alkyl,
$R^{4.5.2}$ denotes H, $C_{1-3}$-alkyl and
$R^{4.5.3}$ denotes H, $C_{1-3}$-alkyl,
the tautomers, the diastereomers, the enantiomers, the hydrates, the mixtures thereof and the salts thereof and the hydrates of the salts, particularly the physiologically acceptable salts thereof with inorganic or organic acids or bases.

A ninth embodiment of the present invention comprises the compounds of the above general formula I, wherein U, V, X, Y, $R^1$ and $R^2$ are defined as hereinbefore in the first, second, fourth or sixth embodiment and
$R^3$ denotes
  (a) H,
  (b) $C_{1-6}$-alkyl,
  (c) a $C_{3-6}$-cycloalkyl substituted by one or two groups $R^{3.2}$, or
  (d) a $C_{1-3}$-alkyl group, wherein each methylene group is substituted by up to two fluorine atoms and each methyl group is substituted by up to three fluorine atoms,
$R^{3.2}$ independently of one another denote
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group, wherein each methylene group is substituted by up to two fluorine atoms and each methyl group is substituted by up to three fluorine atoms,
$R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$ or
  (f) a $C_{5-6}$-cycloalkyl group, which may be fused to a phenyl group and which is additionally substituted by one or two groups $R^{4.2}$,
$R^{4.1}$ denotes
  (a) H or
  (b) a phenyl group substituted by the groups $R^{4.1.1}$ and $R^{4.1.2}$,
$R^{4.1.1}$ denotes
  (a) H,
  (b) halogen, $C_{1-3}$-alkyl, —OH, —O—$C_{1-3}$-alkyl, —CN, —C(O)—O—$R^{4.1.1.3}$,
  (c) a $C_{1-3}$-alkyl- or —O—$C_{1-3}$-alkyl group, wherein each methylene group is substituted by up to two fluorine atoms and each methyl group is substituted by up to three fluorine atoms,
$R^{4.1.1.3}$ denotes H, $C_{1-3}$-alkyl,
$R^{4.1.2}$ denotes
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group, wherein each methylene group is substituted by up to two fluorine atoms and each methyl group is substituted by up to three fluorine atoms, or
$R^{4.2}$ independently of one another denote
  (a) H,
  (b) halogen, $C_{1-3}$-alkyl, —OH, —O—$C_{1-3}$-alkyl, —CN, —O—C(O)—$C_{1-3}$-alkyl, (c) a $C_{1-3}$-alkyl- or —O—$C_{1-3}$-alkyl group, wherein each methylene group is substituted by up to two fluorine atoms and each methyl group is substituted by up to three fluorine atoms, $R^3$ and $R^4$ together with the nitrogen atom to which they are bound denote:
  (a) a saturated 5- or 6-membered heterocyclic group, which is substituted at a carbon atom by a group $R^{4.3}$ or by two groups $R^{4.3}$ and $R^{4.4}$,
  (b) a saturated 5- or 6-membered heterocyclic group, which is substituted at two adjacent carbon atoms by a group $R^{4.3}$ and $R^{4.4}$ in each case,
  (c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, wherein the fused-on cycloalkyl or heterocyclyl group is substituted by 1, 2 or 3 groups $R^{4.5}$,
  (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$,
  (e) a monounsaturated 5-, 6- or 7-membered heterocyclic group, which is substituted at a carbon atom by a group $R^{4.3}$ or by two groups $R^{4.3}$ and $R^{4.4}$ and is additionally fused to a 5- or 6-membered heteroaryl group, wherein the fused-on heteroaryl group is substituted by 1, 2 or 3 groups $R^{4.5}$ and is selected from among

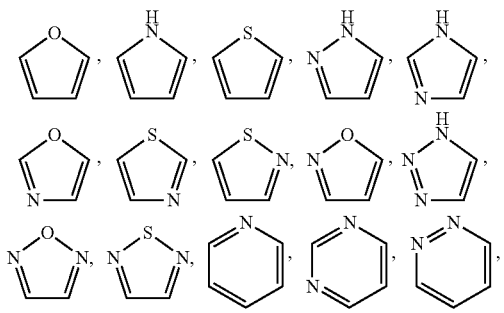

(f) a heteroaryl group, which is substituted in each case by a group $R^{4.5}$ at 1, 2 or 3 carbon atoms, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, $C_{1-3}$-alkyl-O—C(O)—, —NH$_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
  (a) H, $C_{1-3}$-alkyl, —OH, —O—$C_{1-3}$-alkyl,
  (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl or heterocyclyl group, and $R^{4.5}$ independently of one another denote
  (a) H,
  (b) halogen, $C_{1-3}$-alkyl, —OH, —O—$C_{1-3}$-alkyl, —NH$_2$, —CN,
  (c) a $C_{1-3}$-alkyl- or —O—$C_{1-3}$-alkyl group, wherein each methylene group is substituted by up to two fluorine atoms and each methyl group is substituted by up to three fluorine atoms, or
  (d) phenyl, the tautomers, the diastereomers, the enantiomers, the hydrates, the mixtures thereof and the salts thereof and the hydrates of the salts, particularly the physiologically acceptable salts thereof with inorganic or organic acids or bases.

A tenth embodiment of the present invention comprises the compounds of the above general formula I, wherein U, V, X, Y, $R^1$ and $R^2$ are defined as hereinbefore in the first, second, fourth or sixth embodiment and $R^3$ denotes
  (a) H,
  (b) $C_{1-6}$-alkyl,
  (c) a $C_{3-6}$-cycloalkyl group substituted by one or two groups $R^{3.2}$ or
  (d) a $C_{1-3}$-alkyl group, wherein each methylene group is substituted by up to two fluorine atoms and each methyl group is substituted by up to three fluorine atoms, $R^{3.2}$ independently of one another denote
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group, wherein each methylene group is substituted by up to two fluorine atoms and each methyl group is substituted by up to three fluorine atoms, $R^4$ denotes
  (a) H,
  (b) $C_{1-6}$-alkylene-$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) a phenyl group substituted by one or two groups $R^{4.2}$ or
  (f) a $C_{5-6}$-cycloalkyl group, which may be fused to a phenyl group and is additionally substituted by one or two groups $R^{4.2}$, $R^{4.1}$ denotes
  (a) H or
  (b) a phenyl group substituted by the groups $R^{4.1.1}$ and $R^{4.1.2}$, $R^{4.1.1}$ denotes
  (a) H,
  (b) halogen, $C_{1-3}$-alkyl, —OH, —O—$C_{1-3}$-alkyl, —CN, —C(O)—O—$R^{4.1.1.3}$,
  (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.3}$ denotes H, $C_{1-3}$-alkyl, $R^{4.1.2}$ denotes
  (a) H,
  (b) halogen, $C_{1-3}$-alkyl, —OH, —O—$C_{1-3}$-alkyl,
  (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ denotes
  (a) H,
  (b) halogen, $C_{1-3}$-alkyl, —OH, —O—$C_{1-3}$-alkyl, —CN,
  (c) a $C_{1-3}$-alkyl- or —O—$C_{1-3}$-alkyl group, wherein each methylene group is substituted by up to two fluorine atoms and each methyl group is substituted by up to three fluorine atoms, or $R^3$ and $R^4$ together with the nitrogen atom to which they are bound denote:
(a) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$,
(b) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at two adjacent carbon atoms by a group $R^{4.3}$ and $R^{4.4}$ in each case,
(c) a saturated 5-, 6- or 7-membered heterocyclic group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, wherein the fused-on cycloalkyl or heterocyclyl group is substituted by 1, 2 or 3 groups $R^{4.5}$,
(d) a monounsaturated 5-, 6- or 7-membered heterocyclic group, which is selected from among

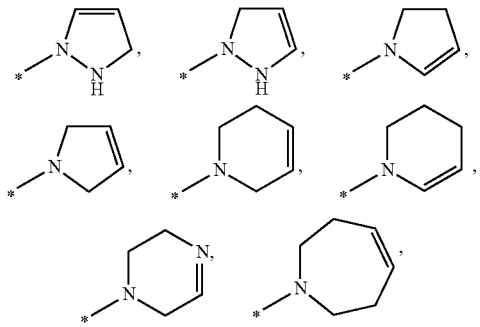

and which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$,
(e) a monounsaturated 5-, 6- or 7-membered heterocyclic group, which is selected from among

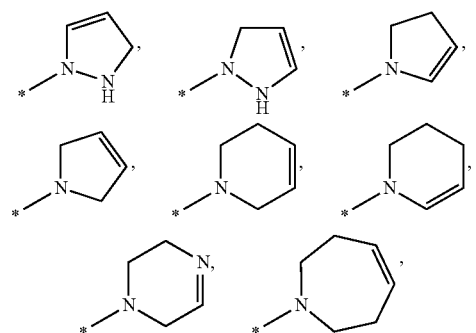

and which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.5}$ and is selected from among

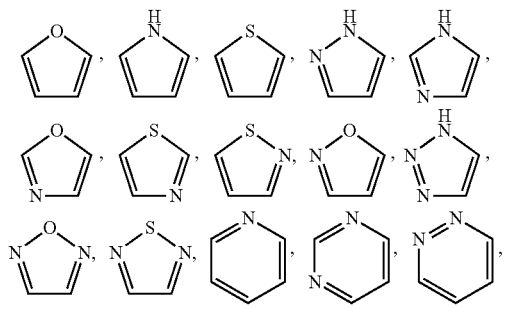

(f) a heteroaryl group, which is selected from among indole, isoindole, azaindole, indazole and benzimidazole, and which is substituted by a group $R^{4.5}$ at 1, 2 or 3 carbon atoms, $R^{4.3}$ denotes H, $C_{1-3}$-alkyl, phenyl, —$C_{1-3}$-alkylene-$R^{4.3.1}$, —$C_{1-3}$-alkyl-O—C(O)—, HO—C(O)—, F, —O—$C_{1-3}$-alkyl, —OH, —CN, $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
(a) H, $C_{1-3}$-alkyl, —OH, —O—$C_{1-3}$-alkyl or
(b) a $C_{1-3}$-alkyl or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl group or a heterocyclyl group which is selected from among azetidinyl, pyrrolidinyl, piperidinyl and azepanyl, and $R^{4.5}$ independently of one another denote
(a) H,
(b) halogen, $C_{1-3}$-alkyl, —OH, —O—$C_{1-3}$-alkyl, —$NH_2$, —CN,
(c) a $C_{1-3}$-alkyl- or —O—$C_{1-3}$-alkyl group, wherein each methylene group is substituted by up to two fluorine atoms and each methyl group is substituted by up to three fluorine atoms, or
(d) phenyl, the tautomers, the diastereomers, the enantiomers, the hydrates, the mixtures thereof and the salts thereof and the hydrates of the salts, particularly the physiologically acceptable salts thereof with inorganic or organic acids or bases.

An eleventh embodiment of the present invention comprises the compounds of the above general formula I, wherein U, V, X, Y, $R^1$ and $R^2$ are defined as hereinbefore in the first, second, fourth or sixth embodiment and $R^3$ denotes
(a) H,
(b) $C_{1-3}$-alkyl or
(c) a $C_{1-3}$-alkyl group, wherein each methylene group is substituted by up to two fluorine atoms and each methyl group is substituted by up to three fluorine atoms, and R[4] denotes H, cyclopropyl or a group selected from

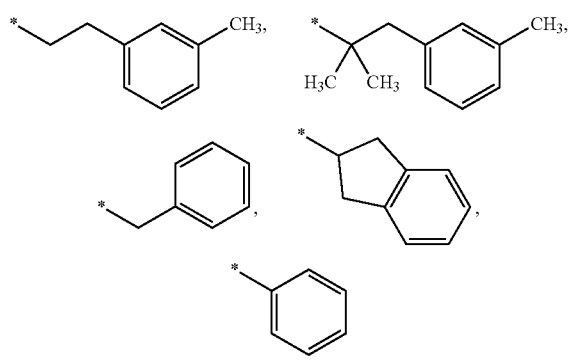

or

R[3] and R[4] together with the nitrogen atom to which they are attached denote a group selected from

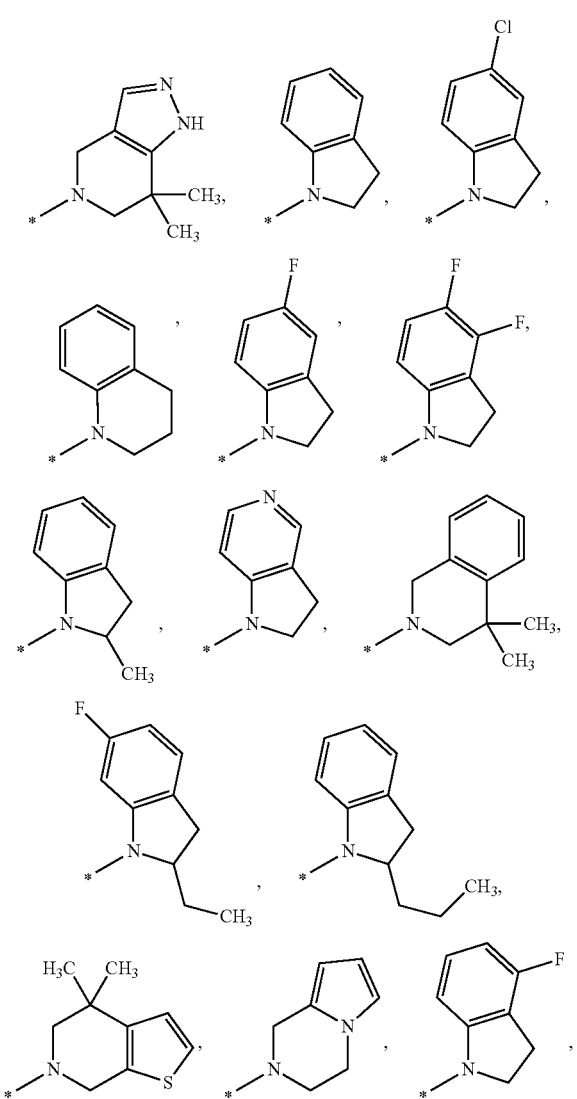

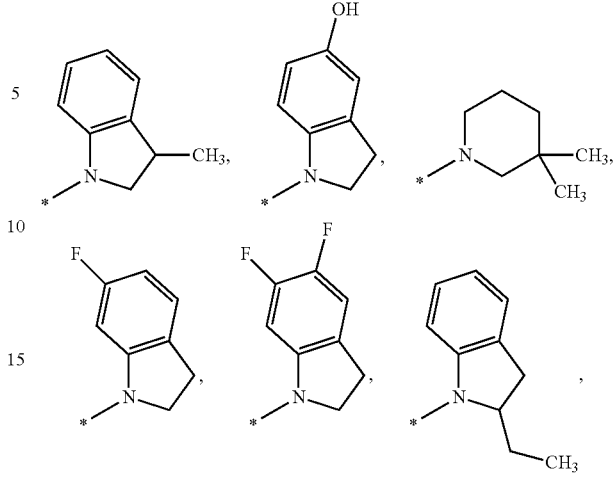

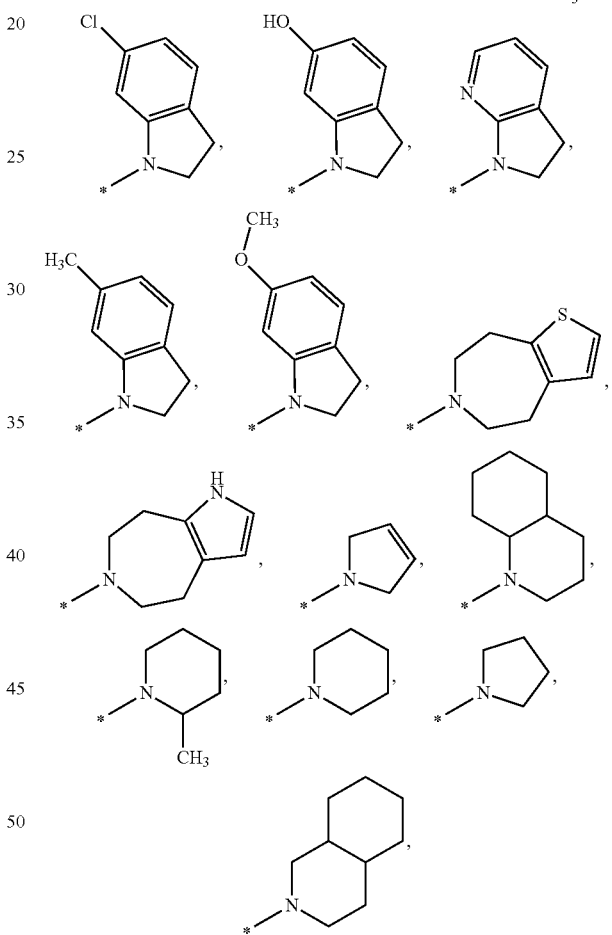

the tautomers, the diastereomers, the enantiomers, the hydrates, the mixtures thereof and the salts thereof as well as the hydrates of the salts, particularly the physiologically acceptable salts thereof with inorganic or organic acids or bases.

A twelfth embodiment of the present invention consists in the compounds of the above general formula I, wherein U, V, X, Y, R[1] and R[2] are as hereinbefore defined in the third, fifth or seventh embodiment and R[3] and R[4] together with the nitrogen atom to which they are attached denote a monounsaturated 5-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O), HO—C(O)—, F, —O—$C_{1-3}$-alkyl, —OH, —CN, $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
 (a) H, $C_{1-3}$-alkyl, —OH, —O—$C_{1-3}$-alkyl or
 (b) a $C_{1-3}$-alkyl- or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denote
 (a) H,
 (b) halogen, $C_{1-3}$-alkyl, —OH, —O—$C_{1-3}$-alkyl, —$NH_2$, —CN,
 (c) a $C_{1-3}$-alkyl- or —O—$C_{1-3}$-alkyl group wherein each methylene group is substituted by up to two fluorine atoms and each methyl group is substituted by up to three fluorine atoms, or
 (d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A thirteenth embodiment of the present invention consists in the compounds of the above general formula I, wherein U, V, X, Y, $R^1$ and $R^2$ are as hereinbefore defined in the third, fifth or seventh embodiment and $R^3$ and $R^4$ together with the nitrogen atom to which they are attached denote a group of general formulae IVa or IVb

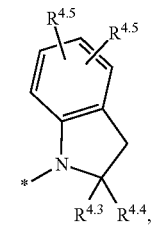

(IVa)

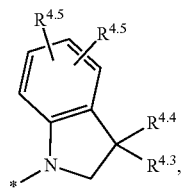

(IVb)

$R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, $R^{4.3.1}$ denotes H, $C_{1-3}$-alkyl-O—C(O)—, —$NH_2$, ($C_{1-4}$-alkyl)-NH—, ($C_{1-4}$-alkyl)$_2$N—, morpholinyl, thiomorpholinyl, piperidinyl, pyrrolidinyl, azetidinyl, $R^{4.4}$ denotes
 (a) H, $C_{1-3}$-alkyl, —OH, —O—$C_{1-3}$-alkyl or
 (b) a $C_{1-3}$-alkyl- or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denote
 (a) H,
 (b) halogen, $C_{1-3}$-alkyl, —OH, —O—$C_{1-3}$-alkyl, —$NH_2$, —CN, $NO_2$,
 (c) a $C_{1-3}$-alkyl- or —O—$C_{1-3}$-alkyl group wherein each methylene group is substituted by up to two fluorine atoms and each methyl group is substituted by up to three fluorine atoms, or
 (d) phenyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourteenth embodiment of the present invention consists in the compounds of the above general formula I, wherein U, V, X, Y, $R^1$ and $R^2$ are as hereinbefore defined in the third, fifth or seventh embodiment and $R^3$ and $R^4$ together with the nitrogen atom to which they are attached denote a group selected from

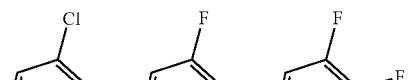

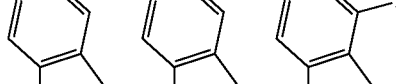

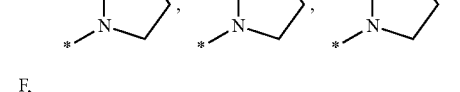

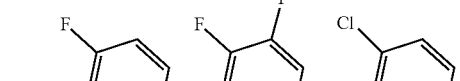

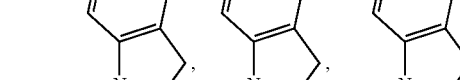

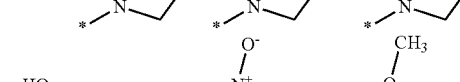

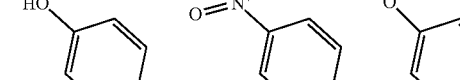

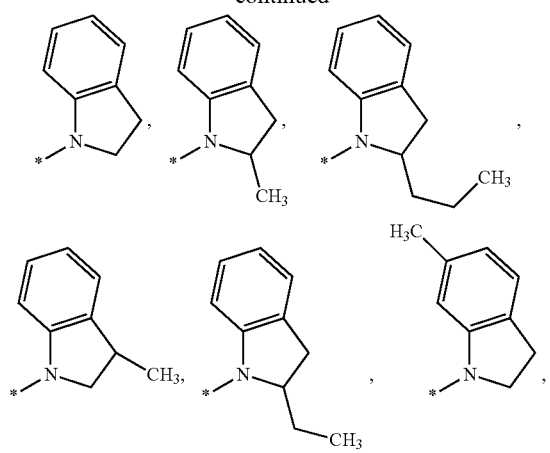

the tautomers, the diastereomers, the enantiomers, the hydrates, the mixtures thereof and the salts thereof as well as the hydrates of the salts, particularly the physiologically acceptable salts thereof with inorganic or organic acids or bases.

A fifteenth embodiment of the present invention consists in the compounds of the above general formula I, wherein $R^1$, $R^2$, $R^3$ and $R^4$ are as hereinbefore defined in the first, second, third, fourth, fifth, sixth, seventh, eighth, ninth, tenth, eleventh, twelfth, thirteenth or fourteenth embodiment and U—V—X denotes a group selected from —N=N—(C—R$^7$)=, —N=(C—R$^6$)—N=, —N=(C—R$^6$)—(C—R$^7$)=, —(N-oxide)=(C—R$^6$)—(C—R$^7$)=, —(C—R$^5$)=N—N=, —(C—R$^5$)=N—(C—R$^7$)=, —(C—R$^5$)=N(oxide)-(C—R$^7$)=, —(C—R$^5$)=(C—R$^6$)—N=, —(C—R$^5$)=(C—R$^6$)—(N-oxide)=, —(C—R$^5$)=(C—R$^6$)—(C—R$^7$)=, $R^5$ denotes H, —CN, $R^6$ denotes H, —NR$^{6.1}$R$^{6.2}$ or —O—C$_{1-3}$-alkyl, $R^{6.1}$ denotes H or C$_{1-6}$-alkyl, $R^{6.2}$ denotes H or —SO$_2$—C$_{1-3}$-alkyl, $R^7$ denotes H or —CN and Y denotes N or CH, the tautomers, the diastereomers, the enantiomers, the hydrates, the mixtures thereof and the salts thereof as well as the hydrates of the salts, particularly the physiologically acceptable salts thereof with inorganic or organic acids or bases.

A sixteenth embodiment of the present invention consists in the compounds of the above general formula I, wherein $R^1$, $R^2$, $R^3$ and $R^4$ are as hereinbefore defined in the first, second, third, fourth, fifth, sixth, seventh, eighth, ninth, tenth, eleventh, twelfth, thirteenth or fourteenth embodiment and the ring

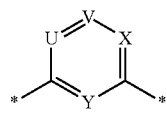

denotes a group selected from

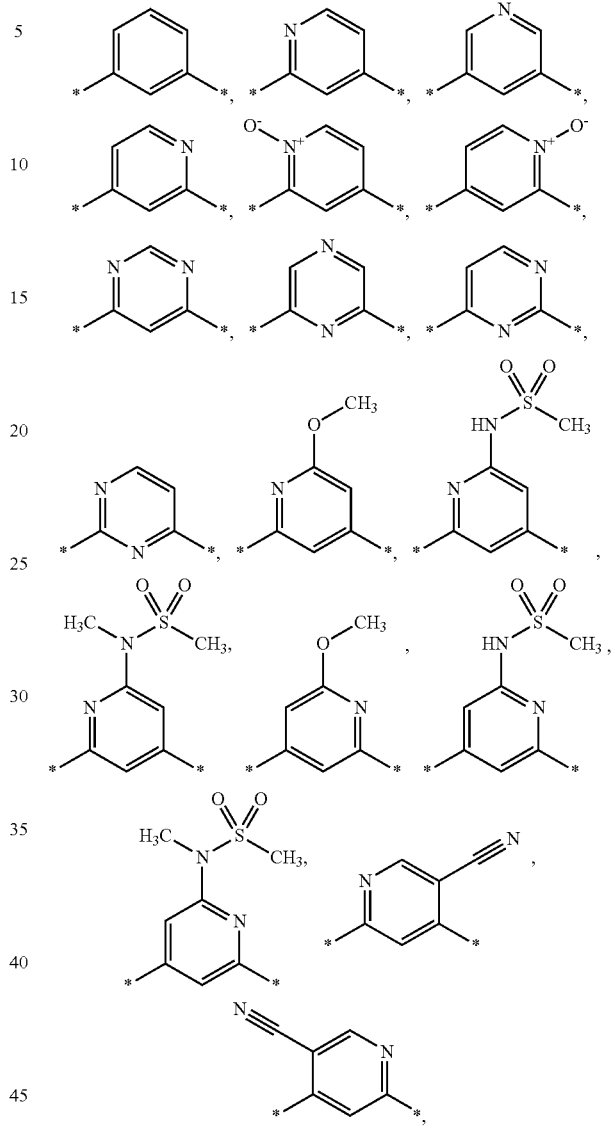

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventeenth embodiment of the present invention consists in the compounds of general formula I wherein $R^1$ denotes a group selected from

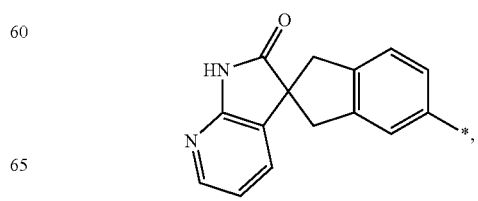

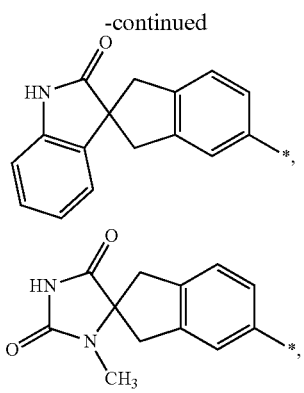
$R^2$ denotes H,
$R^3$ denotes
  (a) H,
  (b) $C_{1-3}$-alkyl or
  (c) a $C_{1-3}$-alkyl group wherein each methylene group is substituted by up to two fluorine atoms and each methyl group is substituted by up to three fluorine atoms, and
$R^4$ denotes H, cyclopropyl or a group selected from
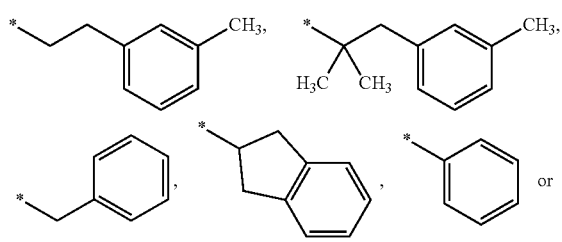
or
$R^3$ and $R^4$ together with the nitrogen atom to which they are attached denote a group selected from
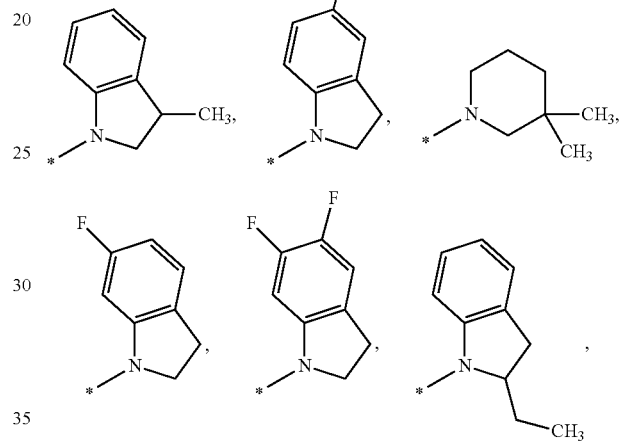
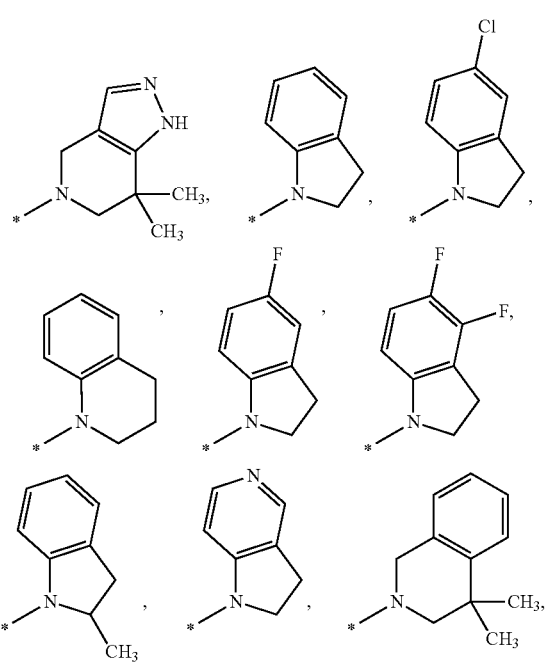
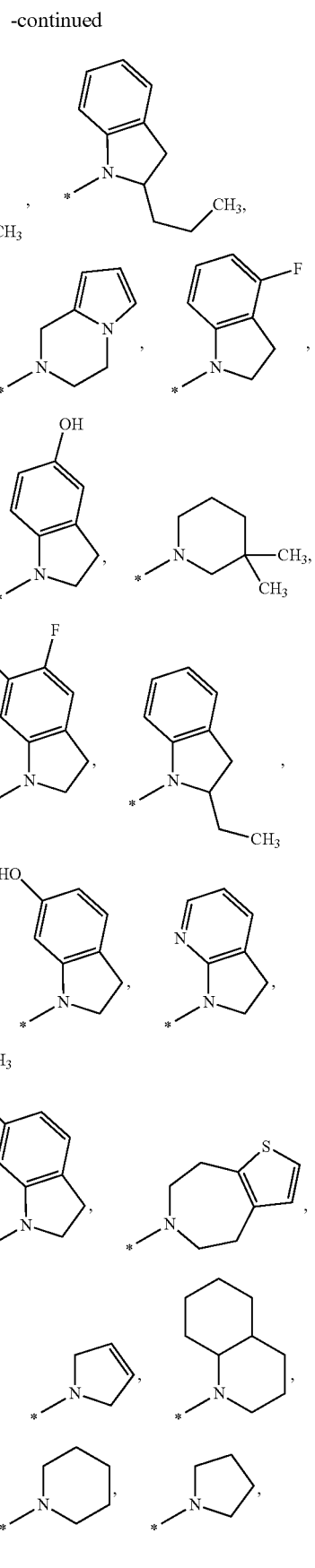
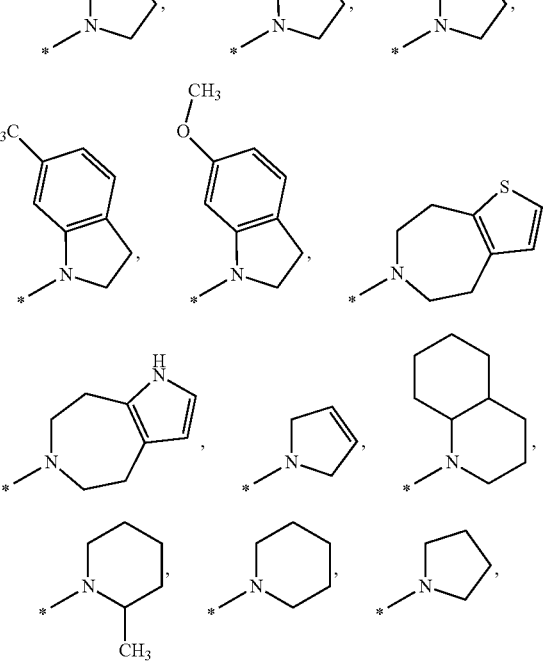

-continued

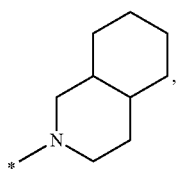

and the ring

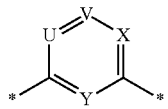

denotes a group selected from

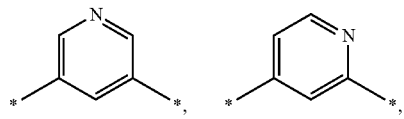

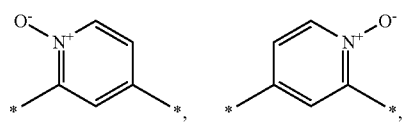

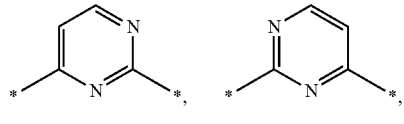

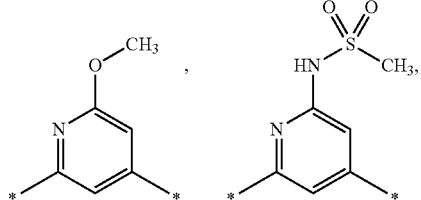

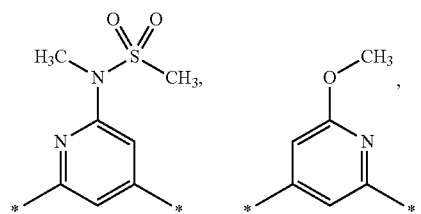

-continued

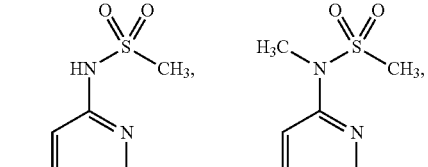

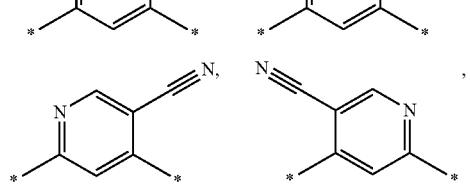

the tautomers, the diastereomers, the enantiomers, the hydrates, the mixtures thereof and the salts thereof as well as the hydrates of the salts, particularly the physiologically acceptable salts thereof with inorganic or organic acids or bases.

An eighteenth embodiment of the present invention consists in the compounds of the above general formula I wherein $R^1$ and $R^2$ together with the nitrogen atom to which they are attached denote a group selected from

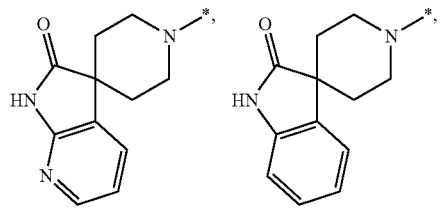

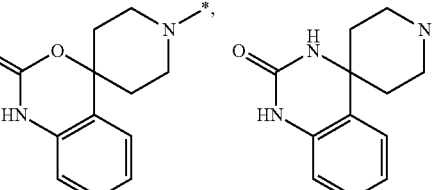

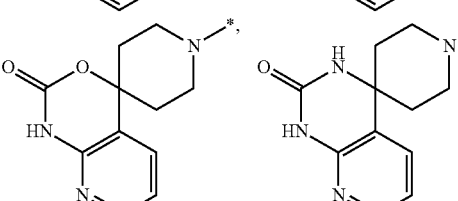

$R^3$ and $R^4$ together with the nitrogen atom to which they are attached denote a group selected from

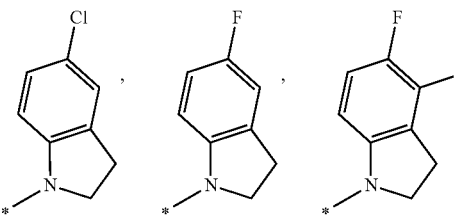

-continued

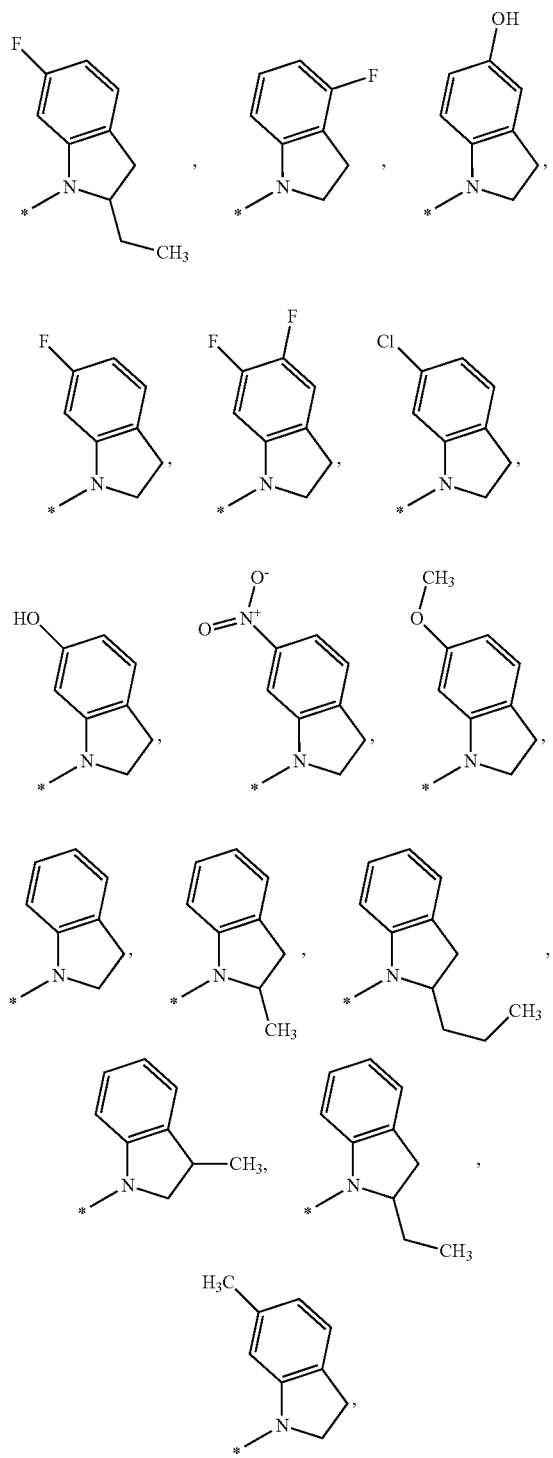

and the ring

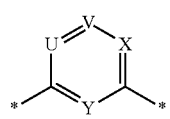

denotes a group selected from

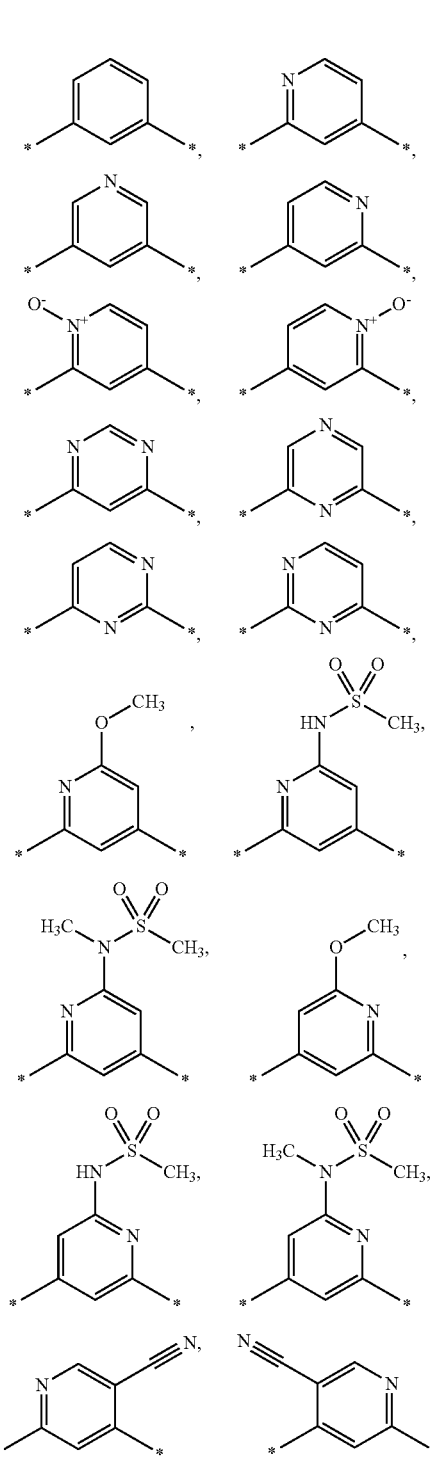

the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned as examples of most particularly preferred compounds of the above general formula I:

| No. | Structure |
|---|---|
| (1) | 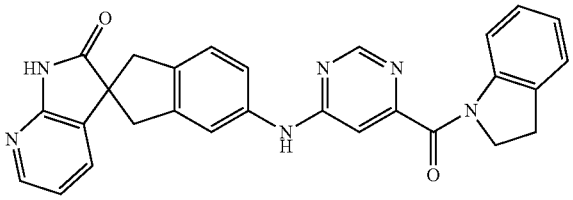 |
| (2) | 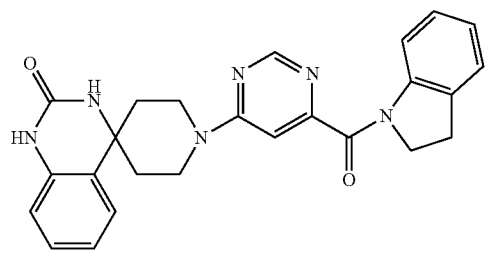 |
| (3) | 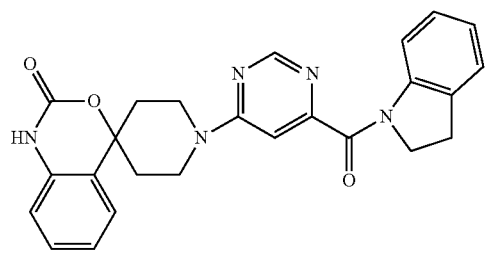 |
| (4) | 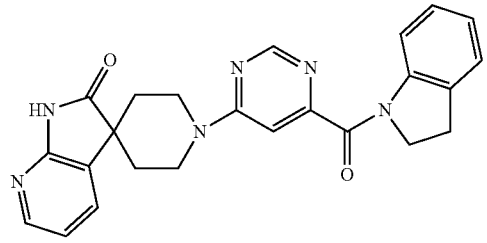 |
| (5) | 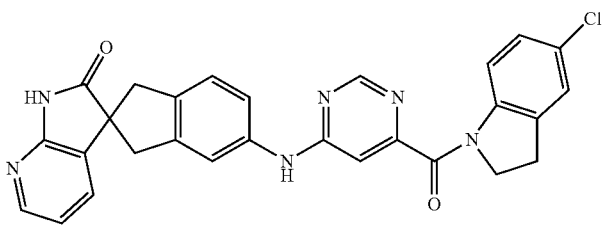 |
| (6) | 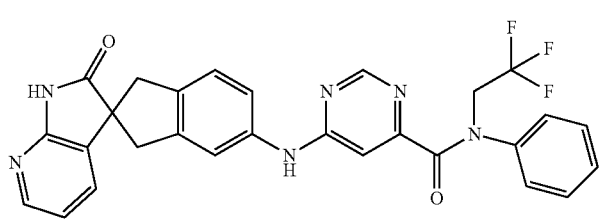 |

-continued

| No. | Structure |
|---|---|
| (7) | 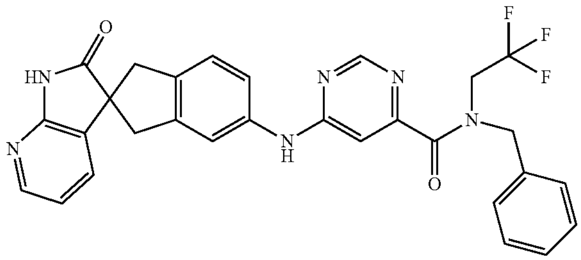 |
| (8) | 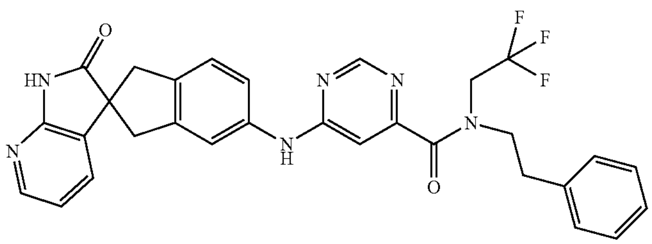 |
| (9) | 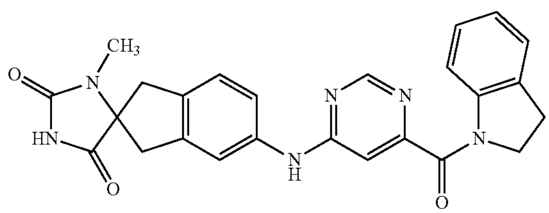 |
| (10) | 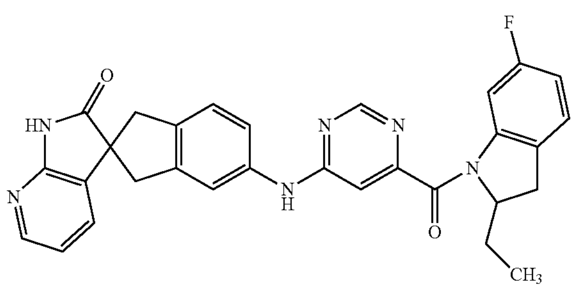 |
| (11) | 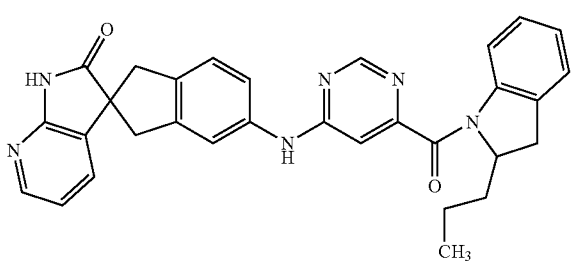 |
| (12) | 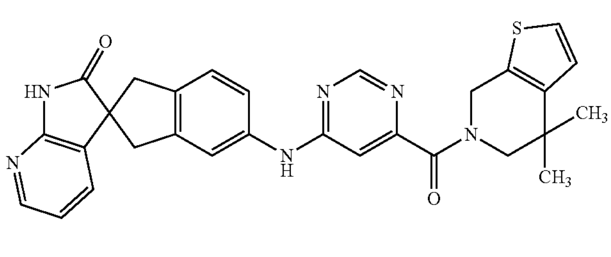 |

-continued

| No. | Structure |
|---|---|
| (13) | 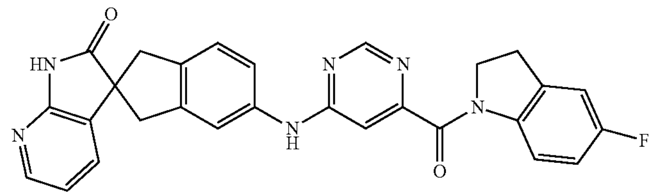 |
| (14) | 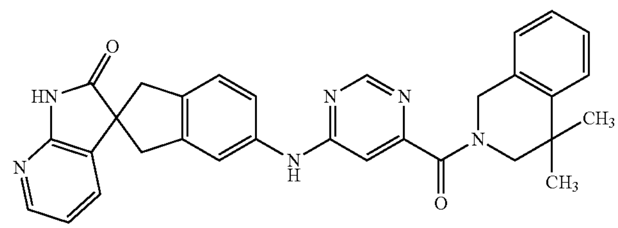 |
| (15) | 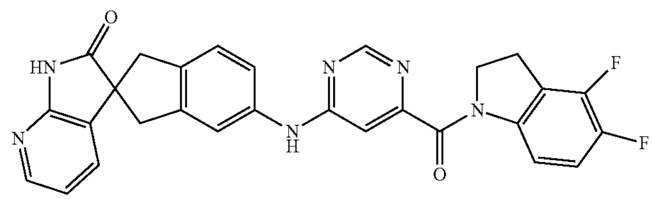 |
| (16) | 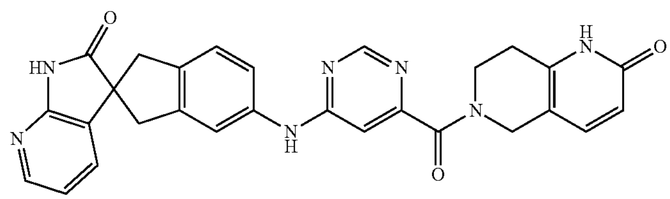 |
| (17) | 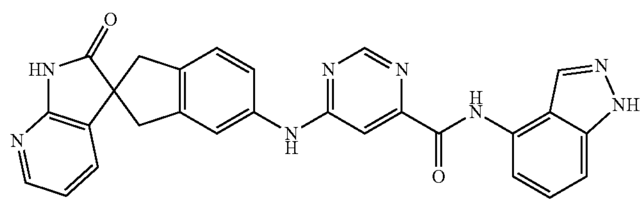 |
| (18) | 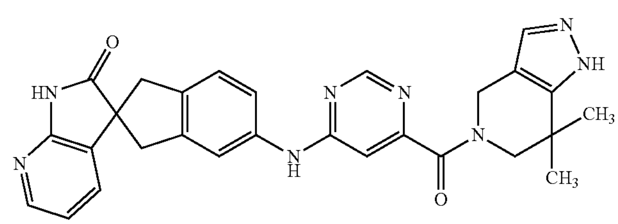 |
| (19) | 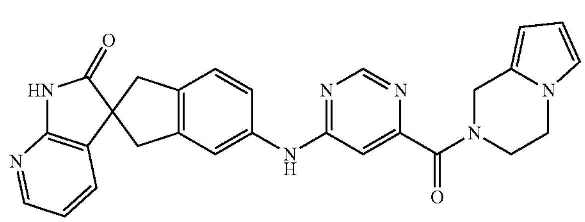 |

-continued

| No. | Structure |
|---|---|
| (20) | 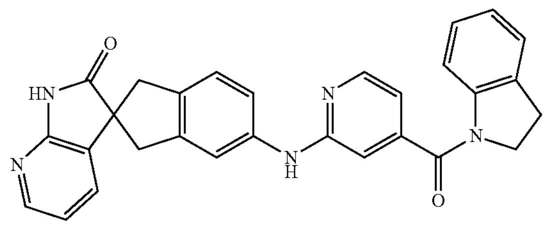 |
| (21) | 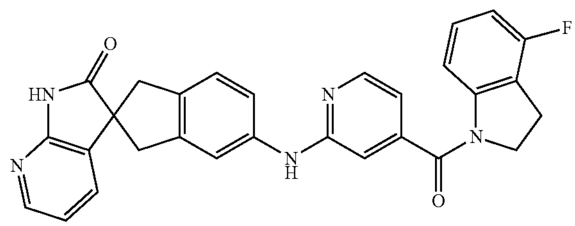 |
| (22) | 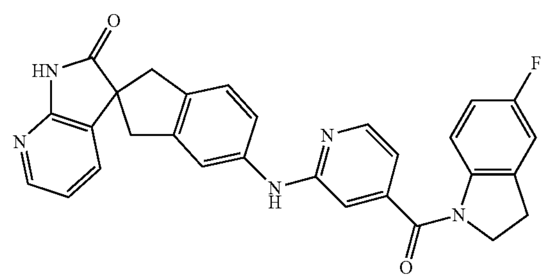 |
| (23) | 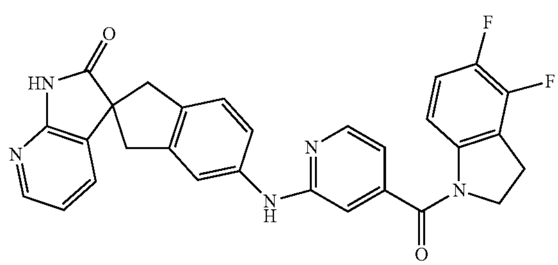 |
| (24) | 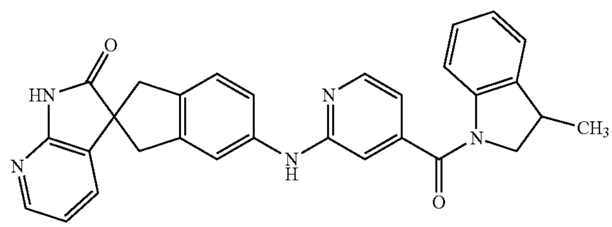 |
| (25) | 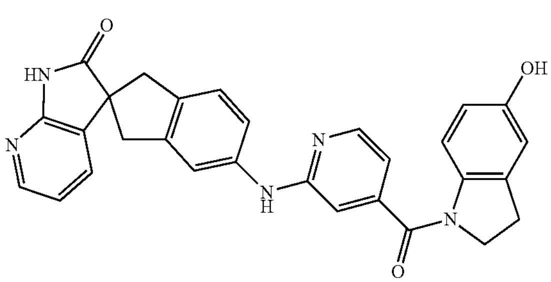 |

-continued
| No. | Structure |
|---|---|
| (26) | 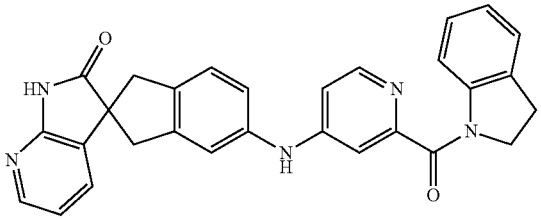 |
| (27) | 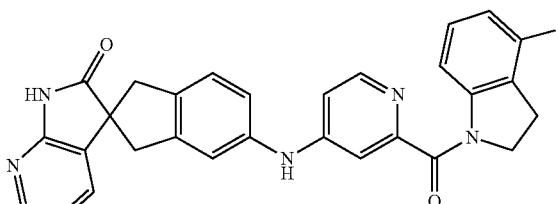 |
| (28) | 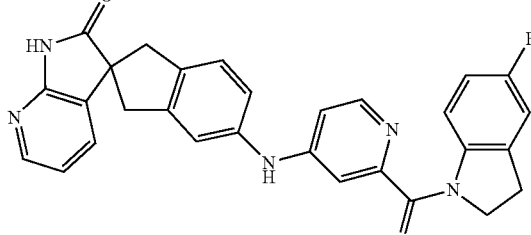 |
| (29) | 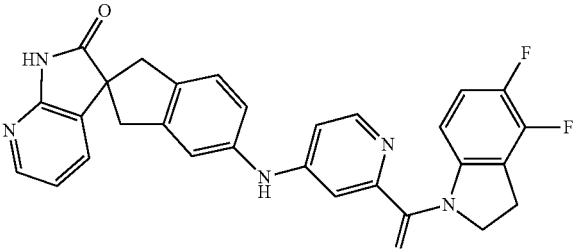 |
| (30) | 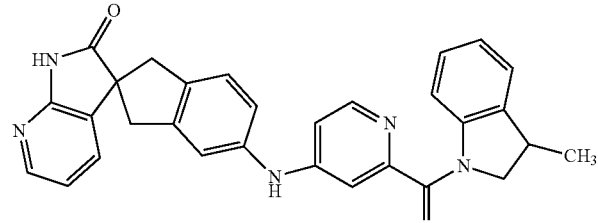 |
| (31) | 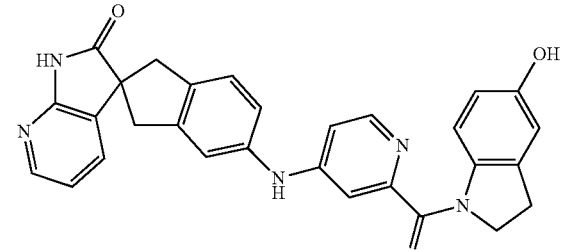 |

| No. | Structure |
|---|---|
| (32) | 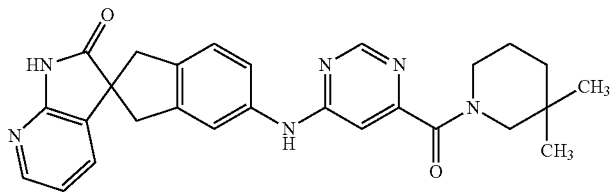 |
| (33) | 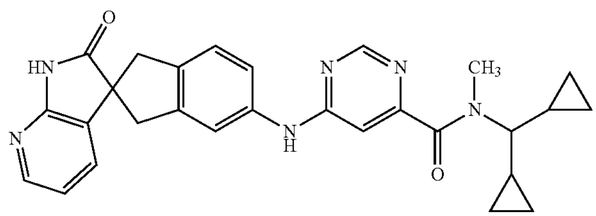 |
| (34) | 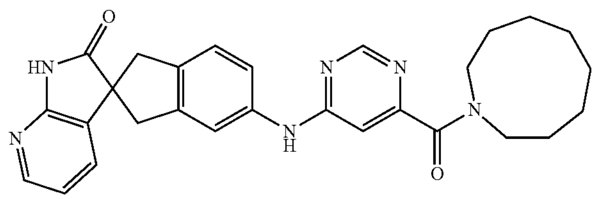 |
| (35) | 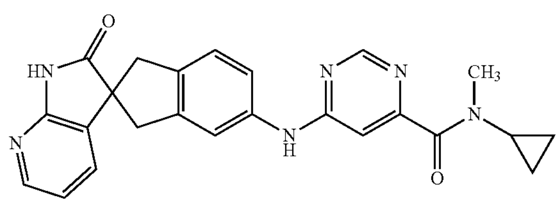 |
| (36) | 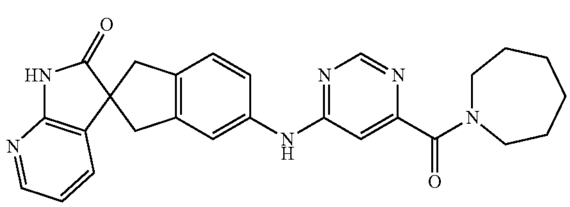 |
| (37) | 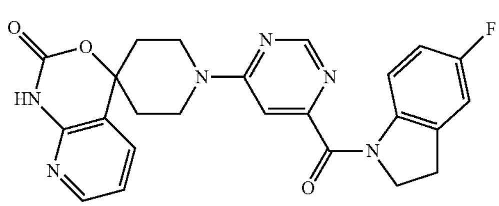 |
| (38) | 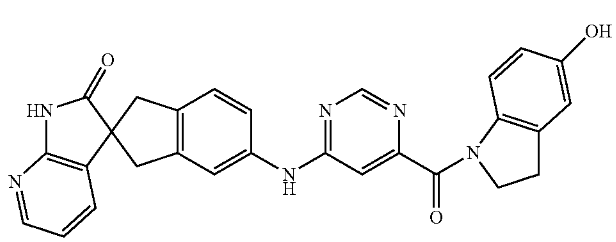 |

-continued
| No. | Structure |
|---|---|
| (39) | 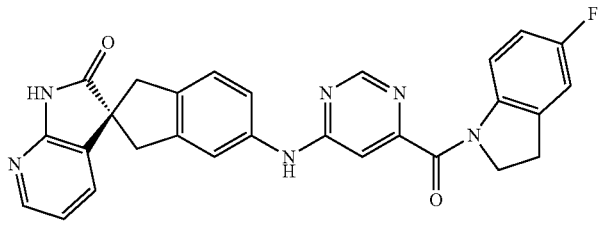 |
| (40) | 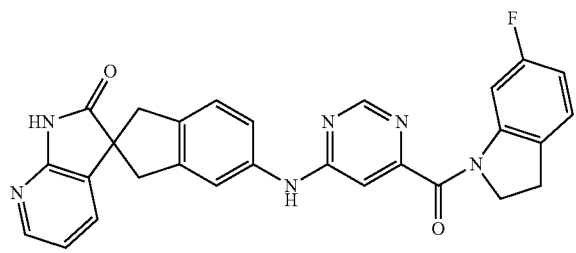 |
| (41) | 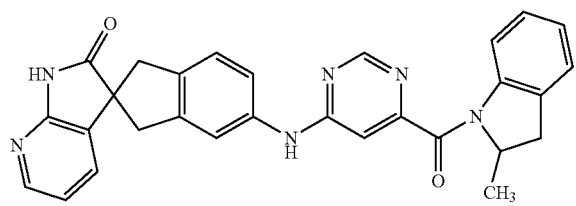 |
| (42) | 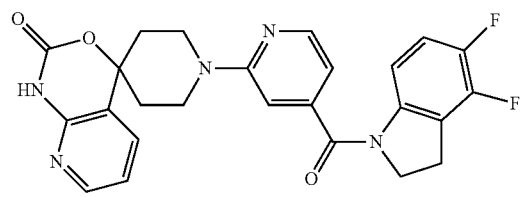 |
| (43) | 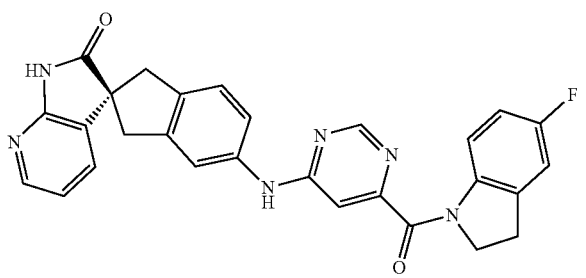 |
| (44) | 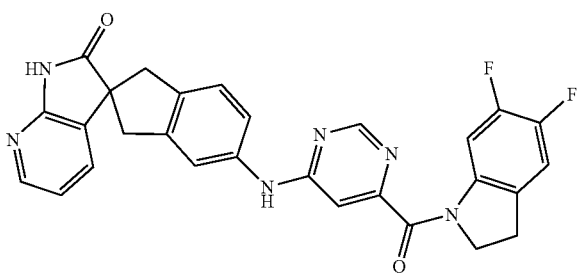 |

-continued

| No. | Structure |
|---|---|
| (45) | 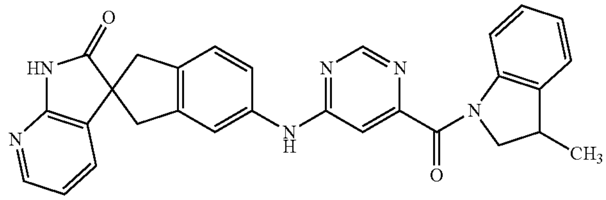 |
| (46) | 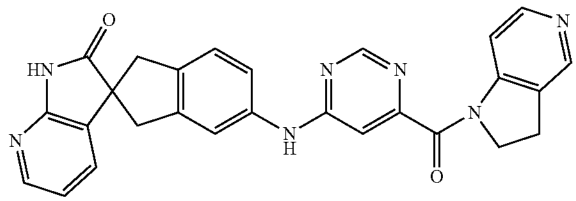 |
| (47) | 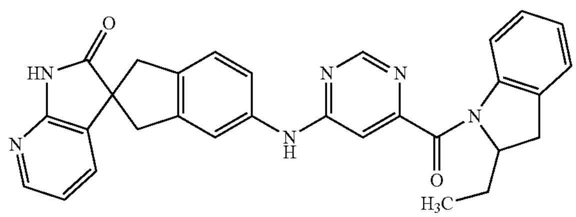 |
| (48) | 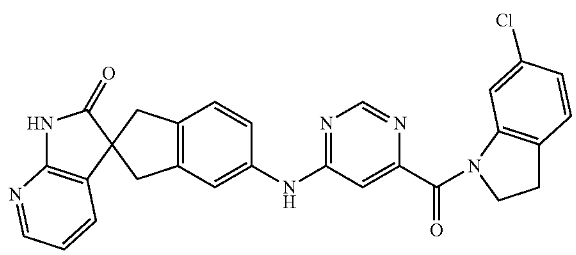 |
| (49) | 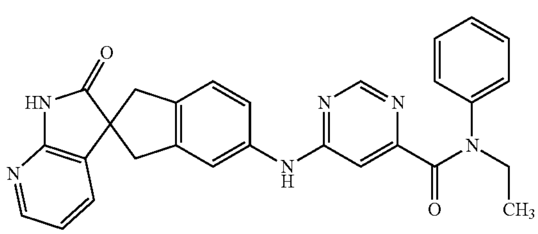 |
| (50) | 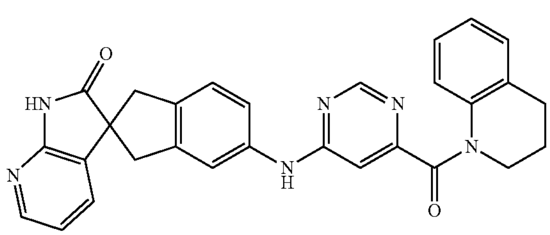 |
| (51) | 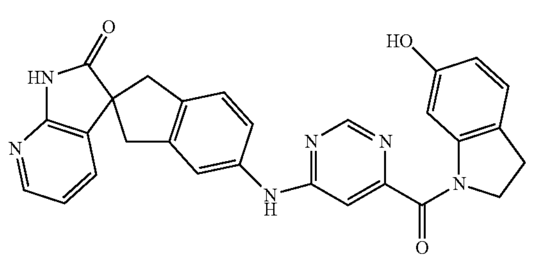 |

-continued
| No. | Structure |
|---|---|
| (52) | 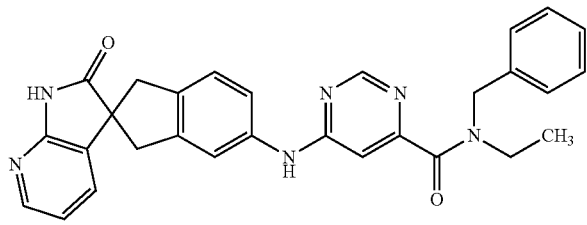 |
| (53) | 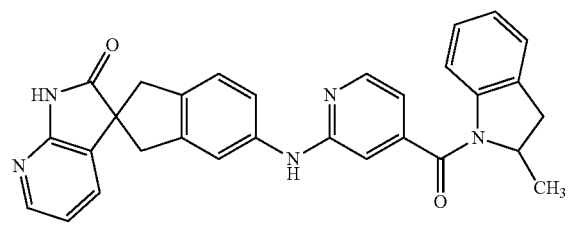 |
| (54) | 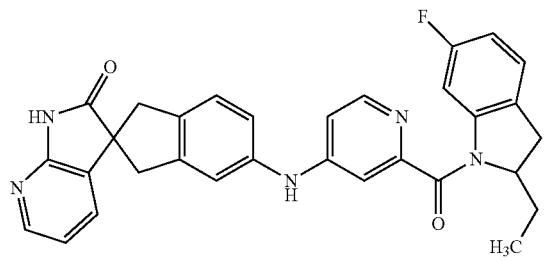 |
| (55) | 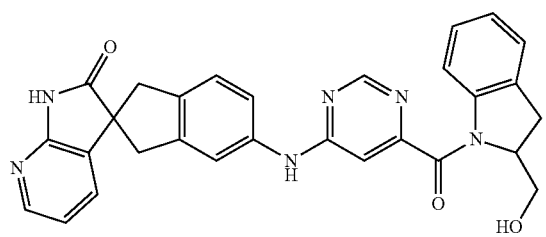 |
| (56) | 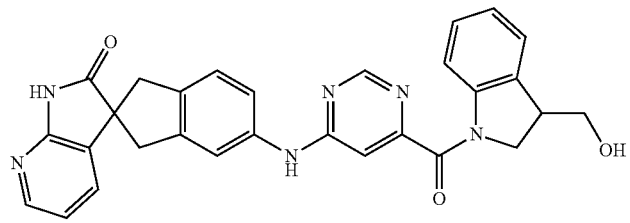 |
| (57) | 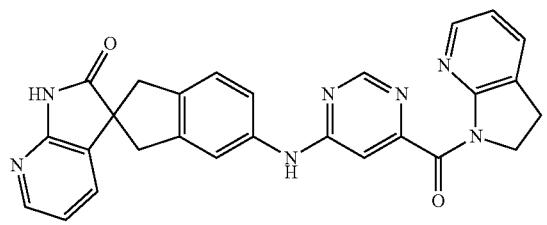 |

-continued

| No. | Structure |
|---|---|
| (58) | 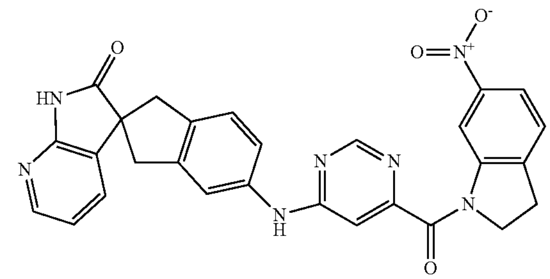 |
| (59) | 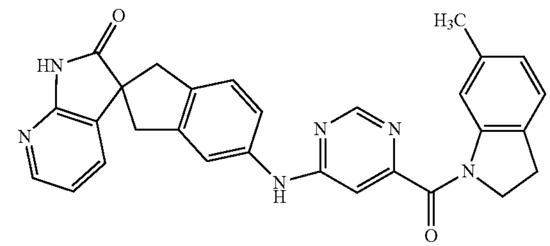 |
| (60) | 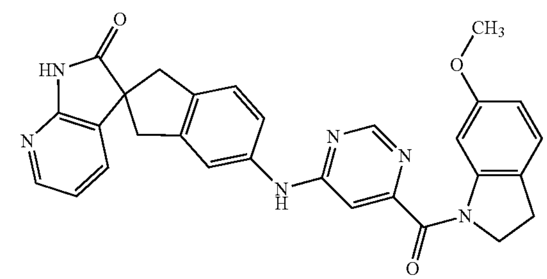 |
| (61) | 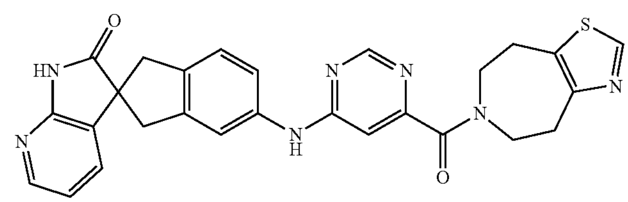 |
| (62) | 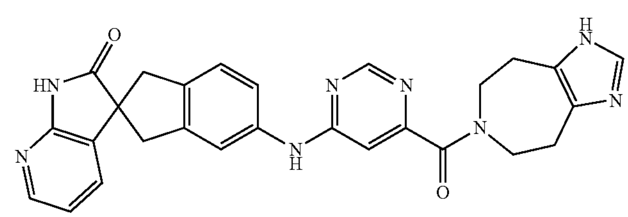 |
| (63) | 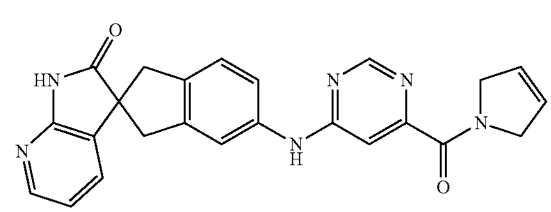 |

-continued

| No. | Structure |
|---|---|
| (64) | 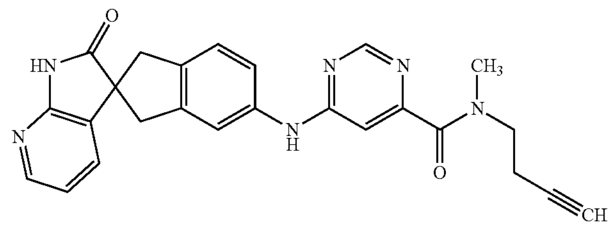 |
| (65) | 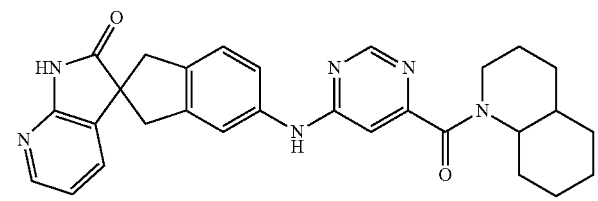 |
| (66) | 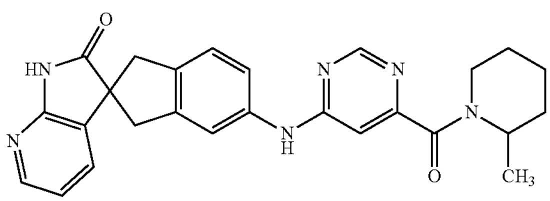 |
| (67) | 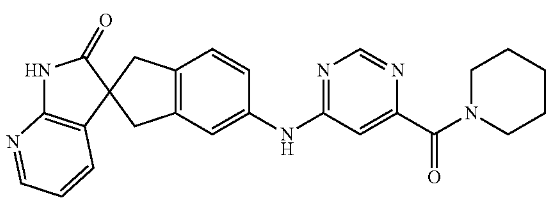 |
| (68) | 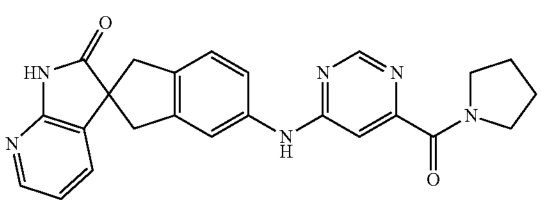 |
| (69) | 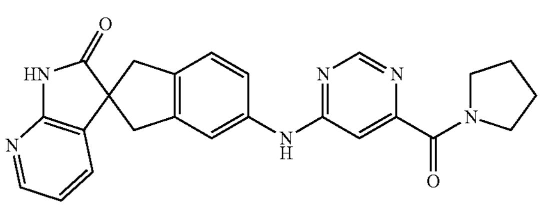 |
| (70) | 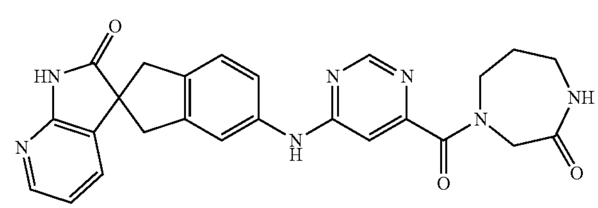 |

-continued

| No. | Structure |
|---|---|
| (71) | ![structure] | the enantiomers, the diastereomers, the hydrates, the mixtures thereof and the salts thereof and the hydrates of the salts, particularly the physiologically acceptable salts thereof with inorganic or organic acids or bases.

Terms and Definitions Used

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

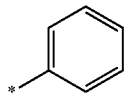

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations may optionally also be used for the above-mentioned groups Me, Et, n-Pr, i-Pr, n-Bu, i-Bu, t-Bu, etc. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms and by the term "$C_{1-3}$-alkylene" are meant branched and unbranched alkylene groups with 1 to 3 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1,1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms, by the term "$C_{5-6}$-cycloalkyl" are meant cyclic alkyl groups with 5 to 6 carbon atoms, and by the term "$C_{5-7}$-cycloalkyl" are meant cyclic alkyl groups with 5 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems, which do not form an aromatic ring system in at least one ring and in addition to carbon atoms may carry one to four heteroatoms selected from among nitrogen, oxygen and sulphur. The two nitrogen atoms and also sulphur atoms may optionally be oxidised and nitrogen atoms may be quaternised. The heterocyclic ring may contain one or two carbonyl, thiocarbonyl or cyanoimino groups adjacent to a nitrogen atom. The heterocycles mentioned previously may be linked to the rest of the molecule via a carbon atom or a nitrogen atom.

Unless otherwise stated, the heterocycles may be substituted by one or more groups selected from among:
(a) OH, NO$_2$, CN, OCF$_3$, OCHF$_2$, OCH$_2$F, NH$_2$,
(b) halogen, preferably fluorine or chlorine,
(c) C$_{1-6}$-alkyl, preferably C$_{1-3}$-alkyl, particularly preferably ethyl, methyl, iso-propyl or tert-butyl,
(d) —SO$_2$—O—C$_{1-3}$-alkyl, preferably —O-methyl,
(e) —O—C$_{1-3}$-alkyl, preferably —O-methyl or —O-ethyl,
(f) COON, COO—C$_{1-3}$-alkyl, preferably CO—O-methyl or CO—O-ethyl,
while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholinyl-5-oxide, thiomorpholinyl-5-dioxide, thiomorpholine, dihydroxazine, morpholinedione, morpholinethione, perhydrothiazinedioxide, ε-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzothiophene, tetrahydrothieno-pyridine, tetrahydrobenzofuran, tetrahydrooxazolopyridine, tetrahydro-isoxazolopyridine.

The following heterocycles are preferred according to the invention:

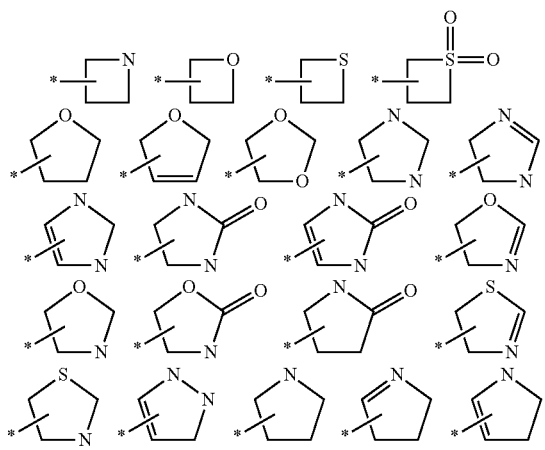

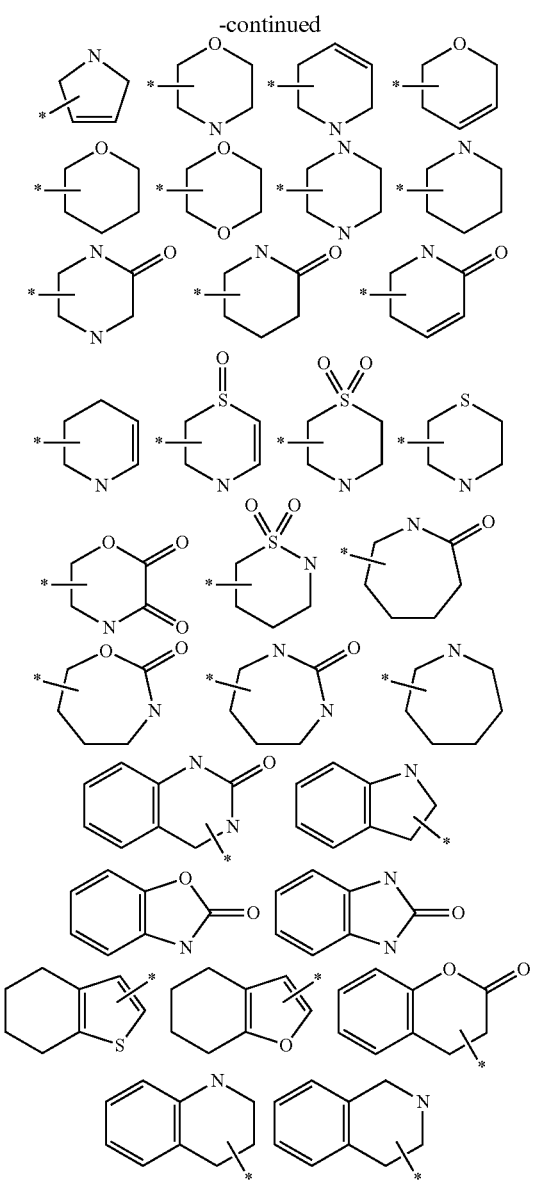

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:
(a) OH, NO$_2$, CN, OCF$_3$, OCHF$_2$, OCH$_2$F, NH$_2$,
(b) halogen, preferably fluorine or chlorine,
(c) C$_{1-6}$-alkyl, preferably C$_{1-3}$-alkyl, particularly preferably ethyl, methyl, iso-propyl or tert-butyl,
(d) —SO$_2$—O—C$_{1-3}$-alkyl, preferably —O-methyl,
(e) —O—C$_{1-3}$-alkyl, preferably —O-methyl or —O-ethyl,
(f) COON, CO—O—C$_{1-3}$-alkyl, preferably CO—O-methyl or CO—O-ethyl,
while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:

furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

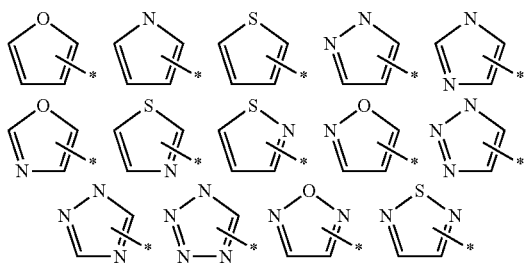

The following six-membered heterocyclic aromatic groups are preferred according to the invention:

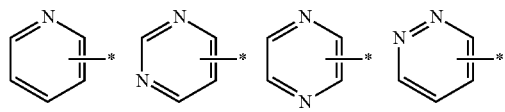

Examples of 9- or 10-membered bicyclic heteroaryl rings are as follows, but the invention is not restricted to these:

indole, isoindole, indazole, indolizine, benzofuran, benzthiophene, benzimidazole, benzoxazole, benzothiazole, benzotriazole, benzisoxazole, benzisothiazole, quinoline, isoquinoline, cinnoline, phthalazine, quinoxaline, quinazoline, pyridopyrimidine, pyridopyrazine, pyridopyridazine, pyrimidopyrimidine, pteridine, purine, quinolizine, benzoxazolecarbonitrile, quinoline, isoquinoline, quinolizine, pteridine, purine, quinolizine, benzoxazole-carbonitrile.

The following bicyclic heteroaryl rings are preferred according to this invention:

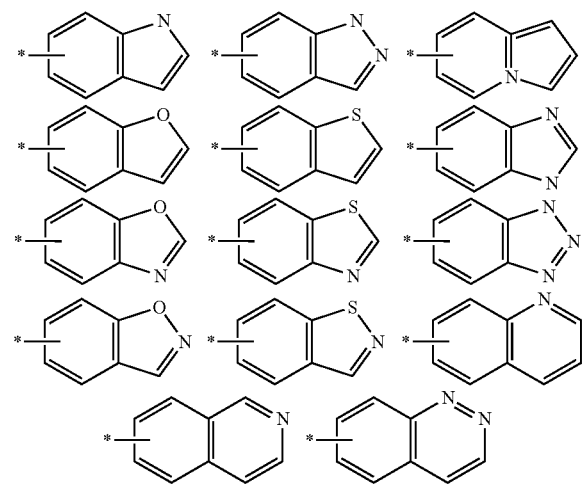

-continued

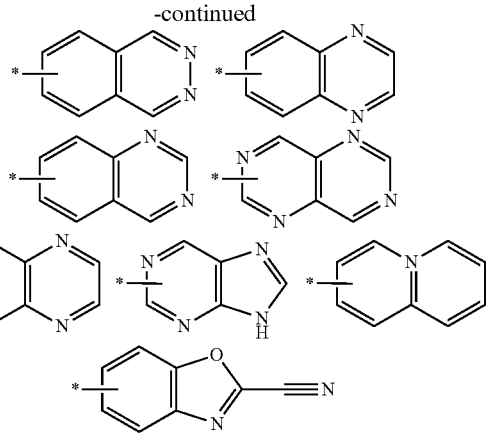

Unless otherwise stated, the heteroaryls previously mentioned may be substituted by one or more groups selected from among:

(a) OH, $NO_2$, CN, $OCF_3$, $OCHF_2$, $OCH_2F$, $NH_2$, (b) halogen, preferably fluorine or chlorine, (c) $C_{1-6}$-alkyl, preferably $C_{1-3}$-alkyl, particularly preferably ethyl, methyl, iso-propyl or tert-butyl, (d) —$SO_2$—O—$C_{1-3}$-alkyl, preferably —O-methyl, (e) —O—$C_{1-3}$-alkyl, preferably —O-methyl or —O-ethyl, (f) COOH, CO—O—$C_{1-3}$-alkyl, preferably CO—O-methyl or CO—O-ethyl, while the groups may be identical or different.

Bicyclic heteroaryl rings may preferably be substituted in the phenyl group.

By the term "halogen" are meant fluorine, chlorine, bromine or iodine atoms.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

Compounds with a carbon double bond may be present in both the E and the Z form.

If a compound may be present in different tautomeric forms, the compound shown is not restricted to one tautomeric form, but includes all the tautomeric forms. This also applies in particular to nitrogen-containing heteroaryls:

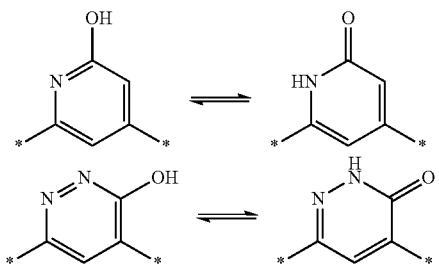

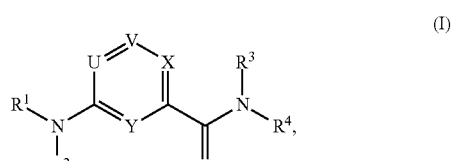

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs. (1986), Elsevier)

This invention also includes those metabolites that are derived from the compounds of general formula I. By metabolites are meant, in this context, compounds that are formed in-vivo from the compound of general formula I after administration. Examples of metabolites include:

methyl groups of the compound of general formula I may be converted into the corresponding hydroxymethyl groups. (—$CH_3$->—$CH_2OH$)

alkoxy groups of the compound of general formula I may be converted into the corresponding hydroxyl groups. (—OR->—OH)

secondary amines of the compound of general formula I may be converted into the corresponding primary amines. (—$NR_1R_2$->—$NHR_1$ or —$NHR_2$)

nitrogen atoms of the compound of general formula I may be converted into the corresponding nitrogen oxides. (=N—->=$N^+$—($O^-$)—)

Methods of Preparation

The invention also relates to a process for preparing the compounds of general formula I, wherein the substituents U, V, X, Y, $R^1$, $R^2$, $R^3$ and $R^4$ are as hereinbefore defined.

Some methods of preparing the compounds of general formula I according to the invention are illustrated in the following synthesis schemes and Examples.

In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

The compounds according to the invention may be prepared according to the schemes and specific examples provided or corresponding modifications thereof. Modifications to these reactions which are known to the skilled man but not described in detail here may also be implemented. The general methods of preparing the compounds according to the invention will become apparent to the skilled man from a study of the following schemes.

Starting compounds are commercially available or are prepared by processes which are described in the literature, known in the art or as described herein. Before the reaction is carried out corresponding functional groups in the compounds may be protected by conventional protective groups. These protective groups may be cleaved again at a suitable stage within the reaction sequence using methods familiar to the skilled man.

In the reactions described below, any reactive groups present such as hydroxy, carboxy, amino, alkylamino, amide or imino groups may be protected during the reaction by conventional protective groups that are cleaved again after the reaction.

For example
a suitable protective group for a hydroxy group may be the methoxy, benzyloxy, trimethylsilyl, acetyl, benzoyl, tert.-butyl, trityl, benzyl or tetrahydropyranyl group,
suitable protective groups for a carboxyl group may be the trimethylsilyl, methyl, ethyl, tert.-butyl, benzyl or tetrahydropyranyl group, and
suitable protective groups for an amide group may be the N-methoxymethyl-(MOM), N-benzyloxymethyl (BOM), N-(trimethylsilyl)ethoxymethyl (SEM), N-tert-butyldimethylsiloxymethyl, N-tert-butyldimethylsilyl (TBDMS), N-triisopropylsilyl-(TIPS), N-benzyl, N-4-methoxybenzyl (PMB), N-triphenylmethyl (Trt), N-tert-butoxycarbonyl (BOC), N-benzyloxycarbonyl (Cbz) or N-trimethylsilylethylsulphonyl (SES)
a suitable protective group for an amino, alkylamino or imino group may be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their cleavage are described in T. W. Greene, P. G. M. Wuts, "Protective Groups in Organic Synthesis", Wiley, 1991 and 1999.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of TBAF and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and in the presence of an excess of a base such as morpholine at temperatures between 0 and 100° C., preferably at ambient temperature and under an inert gas, or by treating with a catalytic amount of tris-(triphenylphosphine)-rhodium(I)chloride in a solvent such as aqueous ethanol and optionally in the presence of a base such as 1,4-diazabicyclo-[2,2,2]octane at temperatures between 20 and 70° C.

The following methods of preparing the compounds of general formula I according to the invention and their precursors have proved particularly suitable:

Scheme 1:

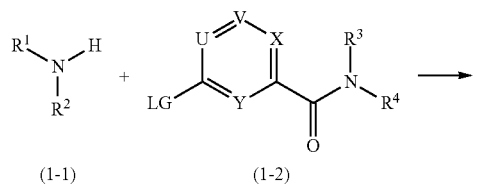

(1-1)    (1-2)

-continued

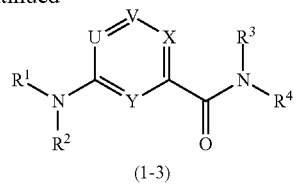

(1-3)

A compound of general formula (1-3), wherein U, V, X, Y, $R^1$, $R^2$, $R^3$ and $R^4$ are as hereinbefore defined, may be prepared by reacting an amine or aniline of general formula (1-1), wherein $R^1$ and $R^2$ are as hereinbefore defined, with an electron-poor compound of general formula (1-2), wherein U, V, X, Y, $R^3$ and $R^4$ are as hereinbefore defined and LG denotes a leaving group. Halides, preferably chlorides and bromides, —SO$_2$CH$_3$, —OSO$_2$CH$_3$, —OSO$_2$C$_6$H$_4$—CH$_3$ or —S—CH$_3$ (—S—CH$_3$ requires further reaction with an organic peroxide in order to be converted into the actual leaving group) etc. may act as the leaving group LG, but it is not restricted to this list. The use of chlorides is most particularly preferred.

The reaction may be carried out by nucleophilic aromatic substitution in an inert solvent using an auxiliary base in a temperature range of from 0° C. to the reflux temperature of the solvent. Nucleophilic aromatic substitutions are carried out in a suitable inert solvent, such as tetrahydrofuran, toluene, xylene, dialkylformamide (particularly preferably dimethylformamide), cyclic amide (particularly preferably N-methyl-pyrrolidone), 1,4-dioxane, acetonitrile or in solvent mixtures. Suitable auxiliary bases include tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. The reaction is preferably carried out in dimethylformamide, at temperatures between ambient temperature and the reflux temperature of the solvent, in the presence of a tertiary amine base.

Alternatively, structures of general formula (1-3) as shown in Scheme 1 may be synthesised by transition metal-catalysed reactions. An amine or aniline of general formula (1-1), wherein $R^1$ and $R^2$ are as hereinbefore defined, may react with a compound of general formula (1-2) wherein U, V, X, Y, $R^3$ and $R^4$ are as hereinbefore defined and LG denotes a leaving group, in an inert solvent in the presence of a catalyst and an auxiliary base. In addition, a suitable ligand may be used for the catalyst. Chlorides, bromides, iodides, trifluoroacetates, trifluoromethanesulphonates, methanesulphonates and toluenesulphonates may act as the leaving group LG, but this list is not restrictive. Xylene, tetrahydrofuran, dimethylformamide, dimethoxyethane, toluene, benzene, tert-butanol, 1,4-dioxane, acetonitrile or solvent mixtures may be used as inert solvents. The preferred solvent is xylene. Suitable bases are particularly amine bases such as e.g. triethylamine or diisopropylethylamine or also inorganic bases such as caesium carbonate, caesium acetate, potassium carbonate, potassium-tert-butoxide, sodium carbonate, sodium-tert-butoxide or potassium phosphate. Preferred reaction temperatures are from RT to the reflux temperature of the solvent at normal pressure. Typical catalysts are e.g. transition metal catalysts, such as e.g. palladium catalysts of the tris(dibenzylideneacetone)-dipalladium(0), tetrakis-(triphenylphosphine)-palladium(0), palladium-(II)-acetate, Pd(PPh$_3$)$_2$Cl$_2$, Pd(CH$_3$CN)$_2$Cl$_2$, Pd(dppf)Cl$_2$ or palladium(II)-chloride type. Typical Scheme 2:

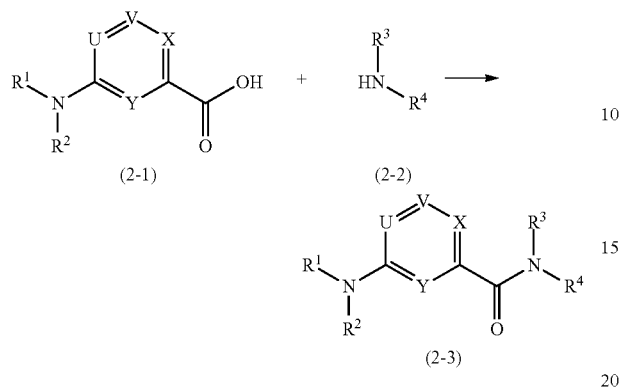

A compound of general formula (2-3), wherein U, V, X, Y, $R^1$, $R^2$, $R^3$ and $R^4$ are as hereinbefore defined, may be prepared as shown in Scheme 2 by coupling a compound of general formula (2-2), wherein $R^3$ and $R^4$ are as hereinbefore defined, with a carboxylic acid of general formula (2-1), wherein U, V, X, Y, $R^1$ and $R^2$ are as hereinbefore defined, using standard peptide-coupling reagents and a base in an inert solvent (cf. e.g. Houben-Weyl, Methoden der Organischen Chemie, vol. 15/2).

The inert solvents used may be dimethylformamide, N-methylpyrrolidone, dimethoxyethane, dichloromethane, acetonitrile or solvent mixtures. The preferred solvent is dimethylformamide. Suitable bases are especially amine bases such as e.g. triethylamine or diisopropylethylamine. Suitable coupling reagents include for example 1H-benzotriazol-1-yl-oxy-tripyrrolidino-phosphonium hexafluorophosphate (PyBOP), dicyclohexylcarbodiimide (DCC), diisopropylcarbodiimide (DIC), ethyl-(3-dimethylamino-propyl)-carbodiimide, O-(1H-benzotriazol-1-yl)-N,N-N,N-tetramethyluronium-hexafluorophosphate (HBTU) or -tetrafluoroborate (TBTU) or 1H-benzotriazol-1-yl-oxy-tris-(dimethylamino)-phosphonium-hexafluorophosphate (BOP). It is particularly preferred to use TBTU. The activation of the carboxyl group may alternatively also be carried out using a corresponding acid anhydride or acid chloride. The reaction is generally carried out in a temperature range from −20° C. to the reflux temperature of the solvent at normal pressure. Reactions are most particularly preferably carried out at ambient temperature. The speed of the reaction can be increased by the addition of 1-hydroxybenzotriazole (HOBt) or of 3-hydroxy-4-oxo-3,4-dihydro-1,2,3-benzotriazine (HOObt). Other standard coupling conditions may also be used in the synthesis of these amides.

The compounds of general formula (3-4), wherein U, V, X, Y, $R^1$ and $R^2$ are as hereinbefore defined, may be synthesised either by methods known to the skilled man or by reactions illustrated in Scheme 3 by way of example.

Scheme 3:

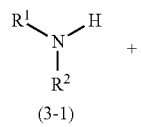

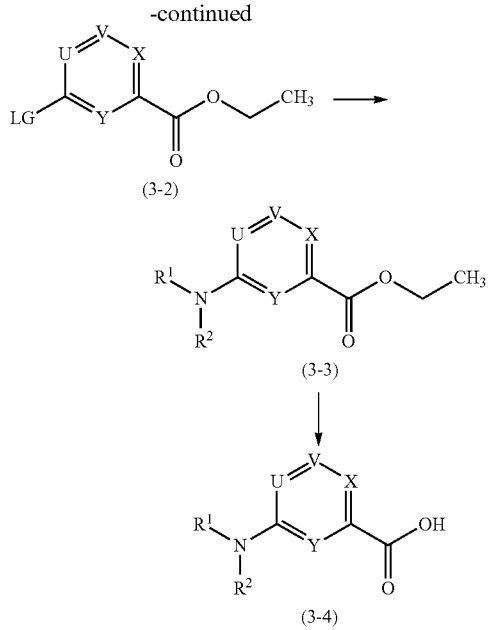

A compound of general formula (3-1), wherein $R^1$ and $R^2$ are as hereinbefore defined, may be reacted with an electron-poor compound of general formula (3-2), wherein U, V, X and Y are as hereinbefore defined and an LG denotes a leaving group. Halides, preferably chlorides and bromides, —SO$_2$CH$_3$, —OSO$_2$CH$_3$, —OSO$_2$C$_6$H$_4$—CH$_3$ or —S—CH$_3$ (—S—CH$_3$ requires further reaction with an organic peroxide in order to be converted into the actual leaving group) etc. may act as the leaving group LG, but it is not restricted to this list. The use of chlorides is most particularly preferred. The reaction may be carried out in an inert solvent using an auxiliary base in a temperature range from 0° to the reflux temperature of the solvent. The inert solvent may be tetrahydrofuran, toluene, xylene, dialkylformamide (dimethylformamide is particularly preferred), cyclic amide (N-methylpyrrolidone is particularly preferred), 1,4-dioxane, acetonitrile or solvent mixtures. Suitable auxiliary bases are especially tertiary amines such as triethylamine or ethyldiisopropylamine and alkali metal carbonates such as potassium carbonate or sodium carbonate. Preferably the reaction is carried out in dimethylformamide, at temperatures between ambient temperature and the reflux temperature of the solvent, in the presence of a tertiary amine base.

Esters of general formula (3-3), wherein U, V, X, Y, $R^1$ and $R^2$ are as hereinbefore defined, may be converted by basic or acid hydrolysis (J. March, Advanced Organic Chemistry (New York: J. Wiley and Sons, 1985) or by reaction with alkali metal salts (preferably LiI or NaCN) in an inert solvent into the acid of general formula (3-4). Inert solvents may be dialkylformamide (N,N-dimethylformamide is particularly preferred), dialkylacetamide (N,N-dimethylacetamide is particularly preferred), cyclic amide (N-methylpyrrolidone is particularly preferred). Alkaline saponification with alkali metal hydroxides such as sodium hydroxide or lithium hydroxide in inert solvents is particularly preferred. Suitable inert solvents are water and cyclic ethers such as 1,4-dioxane or tetrahydrofuran as well as solvent mixtures.

The compounds of general formula (4-3), wherein U, V, X, Y, $R^3$ and $R^4$ are as hereinbefore defined and LG denotes a leaving group, may be synthesised analogously to Scheme 4.

Scheme 4:

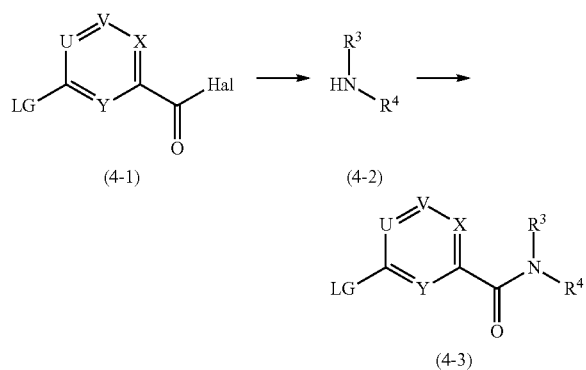

Carboxylic acid halides of general formula (4-1), wherein U, V, X and Y are as hereinbefore defined, and LG denotes a leaving group, for example a chloride or bromide, and Hal denotes a halide, e.g. a chloride or bromide, may be reacted with compounds of general formula (4-2), wherein $R^3$ and $R^4$ are as hereinbefore defined. The reaction may be carried out in an inert solvent or without a solvent. Similarly, the reaction may also be carried out with or without a base. The inert solvents used may be halogen-containing hydrocarbons (the use of dichloromethane or dichloroethane is preferred), dialkylethers (diethyl ether is preferred), cyclic ethers (1,4-dioxane or tetrahydrofuran is preferred) and aromatic hydrocarbons. Bases that may be used are tertiary amines (triethylamine or diisopropylethylamine is preferred) and aromatic amines (pyridine is preferred).

The compounds of general formula (5-3) wherein U, V, X, Y, $R^3$ and $R^4$ are as hereinbefore defined and LG denotes a leaving group may be synthesised analogously to Scheme 5.

Scheme 5:

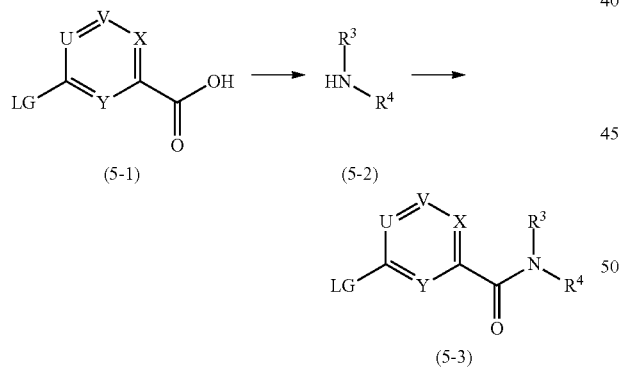

Carboxylic acids of general formula (5-1), wherein U, V, X and Y are as hereinbefore defined and LG denotes a leaving group, may be reacted with compounds of general formula (5-2), wherein $R^3$ and $R^4$ are as hereinbefore defined, using standard peptide coupling reagents and a base in an inert solvent to form amides of general formula (5-3) (cf. e.g. Houben-Weyl, Methoden der Organischen Chemie, vol. 15/2). Halides, preferably chlorides and bromides, —SO$_2$CH$_3$, —OSO$_2$CH$_3$, —OSO$_2$C$_6$H$_4$—CH$_3$ or —S—CH$_3$ (—S—CH$_3$ requires further reaction with an organic peroxide in order to be converted into the actual leaving group) may act as the leaving group LG, but it is not restricted to this list. The inert solvents used may be dimethylformamide, N-methylpyrrolidone, dimethoxyethane, dichloromethane, acetonitrile or solvent mixtures. The preferred solvent is dimethylformamide. Suitable bases are especially amine bases such as e.g. triethylamine or diisopropylethylamine. Suitable coupling reagents include for example 1H-benzotriazol-1-yl-oxy-tripyrrolidino-phosphonium-hexafluorophosphate (PyBOP), dicyclohexylcarbodiimide (DCC), diisopropylcarbodiimide (DIC), ethyl-(3-dimethylamino-propyl)-carbodiimide, O-(1H-benzotriazol-1-yl)-N,N-N,N-tetramethyl-uronium-hexafluorophosphate (HBTU) or -tetrafluoroborate (TBTU) or 1H-benzotriazol-1-yl-oxy-tris-(dimethylamino)-phosphonium-hexafluorophosphate (BOP). Particularly preferred is the use of TBTU. The activation of the carboxyl group may alternatively also be carried out using a corresponding acid anhydride or acid chloride. The reaction is generally carried out in a temperature range from −20° C. to the reflux temperature of the solvent at normal pressure. Particularly preferred is the use of diisopropylethylamine as base and dimethylformamide as solvent.

Compounds of general formula (6-3), wherein U, V, X, Y, $R^1$ and $R^2$ are as hereinbefore defined, may be prepared analogously to Scheme 6.

Scheme 6:

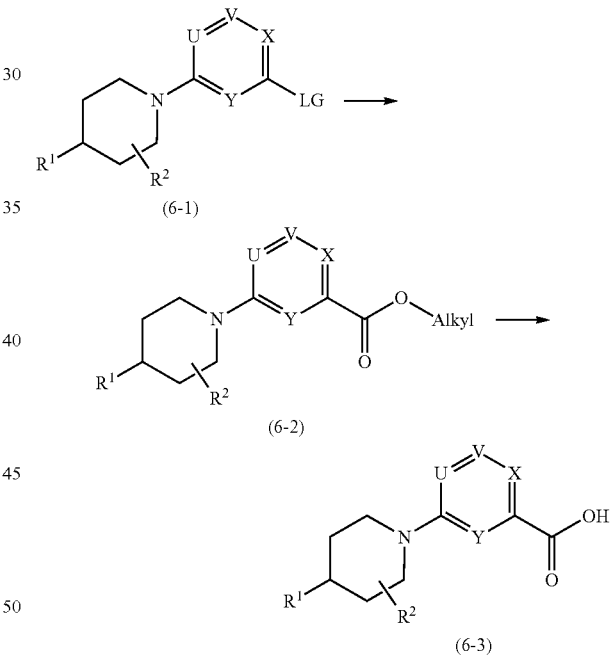

Here, a compound of general formula (6-1), wherein U, V, X, Y, $R^1$ and $R^2$ are as hereinbefore defined and LG denotes a leaving group, may be reacted with an alcohol and carbon monoxide in the presence of a catalyst and an auxiliary base. A suitable ligand may additionally be used for the catalyst. Chlorides, bromides, iodides, trifluoracetates, trifluoromethanesulphonates, methanesulphonates and toluenesulphonates may serve as the leaving group LG, but this list is not restrictive. The alcohols used are preferably methanol and ethanol, but this list is not restrictive. Suitable bases are especially amine bases such as e.g. triethylamine or diisopropylethylamine or also inorganic bases such as caesium carbonate, caesium acetate, potassium carbonate, potassium-tert-butoxide, sodium carbonate, sodium acetate, sodium-tertbutoxide or potassium phosphate. Typical catalysts are transition metal catalysts, such as e.g. palladium catalysts such as tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, $Pd(dppf)Cl_2$ or palladium (II)-chloride. Typical ligands are e.g. triphenylphosphine, tricyclohexylphosphine, tri-(tert-butyl)phosphine, 1,4-bis (diphenylphosphino)butane(dppb),1,1'-bis (diphenylphosphino) ferrocene (dppf), 1,3-bis (diisopropylphosphino)-propane, 1,3-bis (diphenylphosphino)propane(dppp), 1,4-bis (dicyclohexylphosphino)butane, 1,1'-bis (dicyclohexylphosphino)ferrocene. The pressure of carbon monoxide in the reaction vessel is from 1 bar to 100 bar, while elevated carbon monoxide pressures of 10 to 30 bar are preferred. The reactions may be carried out in a temperature range from RT to 200° C. Particularly preferred is a temperature range from 100° C. to 150° C. (M. Beller, W. Magerlein, A. F. Indolese, Ch. Fischer, Synthesis (2001) 7, 1098-1109 and literature cited therein).

Esters of general formula (6-2), wherein U, V, X, Y, $R^1$ and $R^2$ are as hereinbefore defined and alkyl denotes a $C_{1-6}$-alkyl group, may be converted by basic or acid hydrolysis (J. March, Advanced Organic Chemistry (New York: J. Wiley and Sons, 1985) or by reaction with alkali metal salts (preferably LiI or NaCN) in an inert solvent into the acid of general formula (6-3). Inert solvents may be dialkylformamides (particularly preferably N,N-dimethylformamide), dialkylacetamides (N,N-dimethylacetamide is particularly preferred), cyclic amides (N-methylpyrrolidone is particularly preferred). Alkaline saponification with alkali metal hydroxides such as sodium hydroxide or lithium hydroxide in inert solvents is particularly preferred. Suitable inert solvents are water and cyclic ethers such as 1,4-dioxane or tetrahydrofuran as well as solvent mixtures.

In some cases the end product may be further derivatised, e.g. by manipulation of the substituents. These manipulations may be, inter alia, those which are generally known to the skilled man, such as oxidation, reduction, alkylation, acylation and hydrolysis, but need not be restricted to the above.

The new compounds of general formula I according to the invention may contain one or more chiral centres. If for example there are two chiral centres present, the compounds may occur in the form of two diastereomeric pairs of antipodes. The invention includes the individual isomers as well as the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+)- or (−)-tartaric acid, (+)- or (−)-diacetyl tartaric acid, (+)- or (−)-monomethyl tartrate or (+)- or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC membranes (~20 µg protein) are incubated for 180 minutes at ambient temperature with 50 pM $^{125}$I-iodotyrosyl-Calcitonin-Gene-Related Peptide and increasing concentrations of the test substances in a total volume of 250 it (assay buffer: 10 mM tris, 50 mM NaCl, 5 mM $MgCl_2$, 1 mM EDTA, pH=7.4). The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 µM BIBN4096BS during incubation.

The concentration binding curves are analysed using computer-aided non-linear curve fitting.

The compounds mentioned hereinbefore show $K_i$ values ≤50 µm in the test described.

B. CGRP Antagonism in SK-N-MC Cells

SK-N-MC cells (~1000 cells per well) are incubated for 30 minutes in the presence of increasing concentrations of CGRP and different concentrations of the test substance.

The cAMP contents of the samples are determined using an AlphaScreen cAMP assay kit (Perkin Elmer) and the $pA_2$ values of antagonistically acting substances are determined graphically.

The compounds according to the invention exhibit CGRP-antagonistic properties in the in vitro test model described, in a dosage range between $10^{-12}$ and $10^{-4}$ M.

To demonstrate that the compounds of general formula I exhibit good to very good CGRP-antagonistic activities with different structural elements, the following Table gives the $K_i$ values obtained according to the test procedure described above. It should be noted that the compounds were selected for their different structural elements and not in order to emphasise specific compounds:

| Example | $K_i$ [nM] |
| --- | --- |
| (1) | 15 |
| (3) | 535 |
| (6) | 120 |
| (9) | 132 |

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for the treatment of irritable bowel syndrome (IBS) and for the preventive and acute-therapeutic treatment of hot flushes in oestrogen-deficient women.

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, 5-HT$_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-HT$_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. In amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

EXPERIMENTAL SECTION

As a rule IR, $^1$H-NMR and/or mass spectra have been obtained for the compounds prepared. Unless stated otherwise, $R_f$ values are determined using ready-made TLC silica gel plates 60 F254 (E. Merck, Darmstadt, Item no. 1.05714) without chamber saturation.

The ratios given for the eluants relate to units by volume of the particular solvents. The units by volume given for ammonia relate to a concentrated solution of ammonia in water ($NH_4OH$).

Eluant systems used for thin layer chromatography:
eluant A: dichloromethane/cyclohexane/methanol/$NH_4OH$=70/15/15/2
eluant B: petroleum ether/ethyl acetate=2/1

Unless stated otherwise, the acid, base and salt solutions used in working up the reaction solutions are aqueous systems of the specified concentrations. Silica gel made by Millipore (MATREX™, 35-70 µm) is used for chromatographic purifications.

The HPLC data provided are measured under the parameters listed below and using the columns mentioned:
Columns used:
(column temperature: 30° C.; injection volume: 5 µL; detection at 254 nm)

| | |
|---|---|
| S1 | Zorbax column (Agilent Technologies), SB (Stable Bond) C18; 3.5 µm; 4.6 × 75 mm |
| S2 | Waters Sunfire, SB (Stable Bond) C18; 3.5 µm; 4.6 × 75 mm |
| S3 | Agilent Bonus C18; 5 µm, 4.6 × 75 mm |
| S4 | Zorbax column (Agilent Technologies), SB (Stable Bond) C18; 1.8 µm; 3.0 × 30 mm |
| S5 | Zorbax column (Agilent Technologies), SB (Stable Bond) C18; 5 µm; 4.6 × 75 mm |
| S6 | Waters Symmetry C18; 3.5 µm; 4.6 × 75 mm |
| S7 | Waters XBridge C18; 3.5 µm; 4.6 × 75 mm (basic column) |
| S8 | Waters XBridge C18; 3.0 × 30 mm, 2.5 µm (basic column) |
| S9 | Waters Sunfire C18; 4.6 × 50 mm, 3.5 µm (column temperature 40° C.) |

Solvents used:
for the columns S1 to S6 (acid conditions) the following solvents were used:
solvent A: water (with 0.1% formic acid)
solvent B: acetonitrile (with 0.1% formic acid)
for columns S7 and S8 (basic conditions) the following solvents were used:
solvent A: water (with 0.1% NH$_4$OH)
solvent B: acetonitrile (with 0.1% NH$_4$OH)
for column S9 (acid conditions) the following solvents were used:
solvent A: water (with 0.1% trifluoroacetic acid)
solvent B: acetonitrile (with 0.1% trifluoroacetic acid)
(the percentages given relate to the total volume)
Gradients:

| Gradient (flow) | time [min] | % A | % B |
|---|---|---|---|
| G1 (0.8 mL/min) | 0.0 | 95 | 5 |
|  | 8.0 | 50 | 50 |
|  | 9.0 | 10 | 90 |
|  | 10.0 | 10 | 90 |
|  | 11.0 | 95 | 5 |

| Gradient | time [min] | % A | % B |
|---|---|---|---|
| G2 (1.6 mL/min) | 0.00 | 95 | 5 |
|  | 0.10 | 95 | 5 |
|  | 1.75 | 5 | 95 |
|  | 1.90 | 5 | 95 |
|  | 1.95 | 95 | 5 |
|  | 2.00 | 95 | 5 |

| Gradient | time [min] | % A | % B |
|---|---|---|---|
| G3 (1.6 mL/min) | 0.00 | 95 | 5 |
|  | 4.50 | 10 | 90 |
|  | 5.00 | 10 | 90 |
|  | 5.50 | 95 | 5 |

| Gradient | time [min] | % A | % B |
|---|---|---|---|
| G4 (1.6 mL/min) | 0.00 | 95 | 5 |
|  | 4.00 | 50 | 50 |
|  | 4.50 | 10 | 90 |
|  | 5.00 | 10 | 90 |
|  | 5.50 | 95 | 5 |

| Gradient | time [min] | % A | % B |
|---|---|---|---|
| G5 (1.6 mL/min) | 0.00 | 90 | 10 |
|  | 4.50 | 10 | 90 |
|  | 5.50 | 10 | 90 |

| gradient | time [min] | % A | % B |
|---|---|---|---|
| G6 (1.4 mL/min) | 0.00 | 95 | 5 |
|  | 1.80 | 10 | 90 |
|  | 2.00 | 10 | 90 |
|  | 2.20 | 95 | 5 |

| gradient | time [min] | % A | % B |
|---|---|---|---|
| G7 (1.6 mL/min) | 0.00 | 95 | 5 |
|  | 2.00 | 50 | 50 |
|  | 2.25 | 10 | 90 |
|  | 2.50 | 10 | 90 |
|  | 2.75 | 95 | 5 |

| gradient | time [min] | % A | % B |
|---|---|---|---|
| G8 (1.5 mL/min) | 0.00 | 95 | 5 |
|  | 2.00 | 00 | 100 |
|  | 2.50 | 00 | 100 |
|  | 2.60 | 95 | 5 |
|  | 2.90 | 95 | 5 |

Methods:

| Method | Column | Gradient |
|---|---|---|
| Method A | S1 | G4 |
| Method B | S2 | G4 |
| Method C | S4 | G2 |
| Method D | S6 | G4 |
| Method E | S1 | G3 |
| Method F | S3 | G3 |
| Method G | S5 | G4 |
| Method H | S1 | G5 |
| Method K | S2 | G3 |
| Method L | S1 | G2 |
| Method M | S7 | G3 |
| Method N | S2 | G1 |
| Method O | S8 | G6 |
| Method P | S4 | G7 |
| Method Q | S9 | G8 |

In preparative HPLC purifications, the products are collected either under mass control or by UV detection. The fractions containing product are combined and freeze-dried. The following columns may be used for preparative HPLC separations:

| | |
|---|---|
| S8 | Agilent Zorbax SB C18, 50 × 150 mm, 5 μm |
| S9 | Agilent Zorbax Stable Bond, 50 × 140 mm, 7 μm |
| S10 | Waters Sunfire C18, 30 × 100 mm, 5 μm |
| S11 | Waters Symmetry 50 × 140 mm, 7 μm |
| S12 | Agilent Zorbax Stable Bond C18, 30 × 100 mm, 5 μm, |

In the absence of any more information regarding the configuration, it is unclear whether there are pure enantiomers involved or whether partial or even total racemisation has taken place.

The following abbreviations are used in the test descriptions:

AcOH acetic acid
BINAP 2,2'-bis-(diphenylphosphino)-1,1'-binaphthyl
BOC tert.-butyloxycarbonyl
CAD circulating air dryer
CDI 1,1'-carbonyldiimidazole
conc. concentrated
Cyc cyclohexane
DC drying cupboard
DCM dichloromethane
DIPE diisopropylether
DIPEA diisopropylethylamine
DMF N,N-dimethylformamide
dppf 1,1'-bis-(diphenylphosphino)ferrocene
of th. of theory
d-water deionised water
EI electron jet ionisation (in MS)
eq equivalents
ESI electrospray ionisation (in MS)
EtOAc ethyl acetate
EtOH ethanol
GWM General Working Method
HATU O-(7-azabenzotriazol-1-yl)-N,N,N,N-tetramethyluronium-hexafluoro-phosphate
HCl hydrogen chloride
HPLC High Performance Liquid Chromatography
HPLC-MS HPLC coupled mass spectrometry
i.vac. in vacuo (under vacuum)
MeOH methanol
MS mass spectrometry
MW molecular weight [g/mol]
NaOAc sodium acetate
NaOH sodium hydroxide
NH$_4$OH ammonium hydroxide (aqueous ammonia solution, 30%)
NMP N-methyl-2-pyrrolidine
Pd/C palladium on charcoal
PdCl$_2$(PPh$_3$)$_2$ bis(triphenylphosphine)palladium (II) chloride
Pd$_2$dba$_3$ bis(dibenzylideneacetone) palladium (0)
PE petroleum ether
R$_f$ retention index (in TLC)
R$_t$ retention time (in HPLC)
RT ambient temperature
TBTU O-(benzotriazol-1-A-N,N,N,N-tetramethyluronium tetrafluoroborate
TEA triethylamine
TFA trifluoroacetic acid
THF tetrahydrofuran
XantPhos 4,5-bis(diphenylphosphino)-9,9-dimethylxanthene
XPhos 2-dicyclohexylphosphino-2',4',6'-triisopropylbiphenyl Preparation of the Starting Compounds Intermediate 1

1'H-Spiro[piperidin-4,2'-quinazolin]-4'(3'-H)-oe

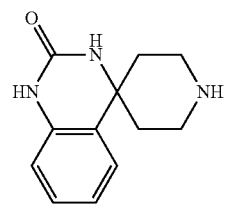

was prepared as described in Published Application WO 2003/104236.

Yield: 5.20 g (97% of th.)
ESI-MS: m/z=218 (M+H)$^+$
R$_f$ (silica gel): 0.08 (eluant A)

Intermediate 2

6-chloropyrimidine-4-carboxylic acid chloride

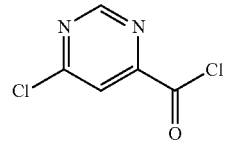

Step 1: 6-Hydroxypyrimidine-4-carboxylic acid

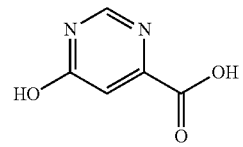

63.5 g (0.3 mol) sodium diethyloxalacetate and 30.2 g (0.3 mol) formamidine acetate were added to 24.1 g (0.6 mol) NaOH in 3.6 L water. The mixture was stirred overnight at RT. Then activated charcoal was added and the mixture was refluxed for 1 h. It was filtered off while hot and after cooling acidified with a hydrochloric acid solution. The solution was concentrated to dryness by rotary evaporation. The residue contained the desired product and was used in the next step without any further purification.

Yield: 83.0 g

Step 2: 6-chloropyrimidine-4-carboxylic acid chloride

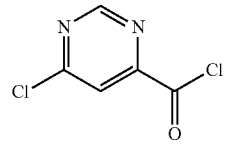

50.0 g (0.35 mol) 6-hydroxypyrimidine-4-carboxylic acid were taken and 500 mL phosphorus oxychloride were added. Then 150 g (0.72 mol) phosphorus pentachloride were added batchwise with stirring. The reaction mixture was refluxed for 5 h. The phosphorus oxychloride was distilled off and the residue was purified by vacuum distillation through a column.
Yield: 51.9 g (83% of th.)
MS: m/z=176/178/180 (M)$^+$

Intermediate 3 ethyl 6-chloropyrimidine-4-carboxylate

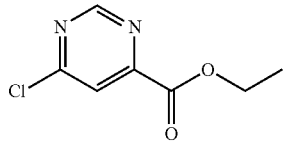

1.0 g (5.65 mmol) 6-chloropyrimidine-4-carboxylic acid chloride and 0.4 mL (6.94 mmol) ethanol were combined in 30 mL dichloromethane and stirred overnight at RT. The solvent was eliminated i.vac.
Yield: 1.0 g (95% of th.)
ESI-MS: m/z=187/189 (M+H)$^+$
R$_f$(silica gel): 0.85 (EtOAc)

Intermediate 4

Ethyl 6-(3-methyl-2,5-dioxo-1',3'-dihydrospiro[imidazolidin-4,2'-inden]-5'-ylamino)pyrimidine-4-carboxylate

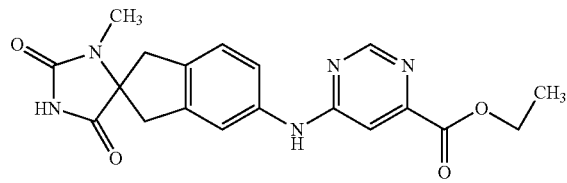

500 mg (2.16 mmol) 5'-amino-3-methyl-1',3'-dihydrospiro[imidazolidine-4,2'-indene]-2,5-dione (Bioorg. Med. Chem. Lett.; 2006; 16; 24; 6165-6169) and 400 µL (2.33 mmol) DIPEA were added to 400 mg (2.14 mmol) ethyl 6-chloropyrimidine-4-carboxylate in 10 mL DMF and the reaction mixture was stirred for 8 h at 100° C. The reaction mixture was diluted with 60 mL water and stirred for 30 min. The precipitate was suction filtered and the filtrate was extracted with dichloromethane (3×40 mL). The organic phases were combined, dried on magnesium sulphate, filtered and evaporated down i.vac. The residue was dissolved in DMF and purified by preparative HPLC. The product fractions were combined and freeze-dried.
Yield: 140 mg (17% of th.)
ESI-MS: m/z=382 (M+H)$^+$
R$_f$(silica gel): 0.49 (eluant A)

Intermediate 5

6-(3-methyl-2,5-dioxo-1',3'-dihydrospiro[imidazolidin-4,2'-inden]-5'-ylamino)pyrimidine-4-carboxylic acid

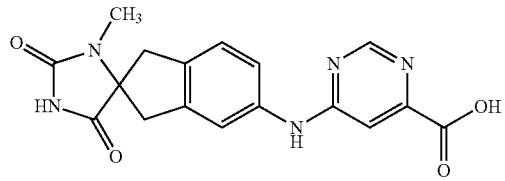

140 mg (0.37 mmol) ethyl 6-(3-methyl-2,5-dioxo-1',3'-dihydrospiro[imidazolidin-4,2'-inden]-5'-ylamino)pyrimidine-4-carboxylate, 5 mL ethanol and 1 mL (1.0 mmol) of a 1M NaOH solution were stirred for 2 h at RT. The reaction mixture was combined with 1 mL of a 1M hydrochloric acid solution and the ethanol was eliminated i.vac. The aqueous residue was cooled and the precipitated product was suction filtered, washed with water and dried.
Yield: 80 mg (62% of th.)
ESI-MS: m/z=354 (M+H)$^+$

Intermediate 6

(6-chloropyrimidin-4-yl)-(2,3-dihydroindol-1-yl)-methanone 0.50 g (2.83 mmol) 6-chloropyrimidine-4-carboxylic acid chloride in 20 mL dichloromethane were cooled with an ice/ethanol bath and combined with 0.30 mL (2.68 mmol) 2,3-dihydro-1H-indole. 2.7 mL (2.7 mmol) of a 1M sodium hydroxide solution were added dropwise. The reaction mixture was stirred for 2 h with cooling and for 1 h at RT. Then 50 mL of an aqueous saturated sodium hydrogen carbonate solution were added. After 10 min stirring the organic phases was separated off and washed with water and 1 M hydrochloric acid. The organic phases was dried on magnesium sulphate, filtered and evaporated down i.vac.

Yield: 570 mg (78% of th.)
ESI-MS: m/z=260/262 (M+H)⁺
R_f (silica gel): 0.59 (eluant B)

Intermediate 7

(5-Chloro-2,3-dihydro-indol-1-yl)-(6-chloro-pyrimidin-4-yl)-methanone

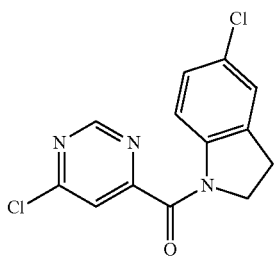

1.5 g (8.48 mmol) 6-chloropyrimidine-4-carboxylic acid chloride in 50 mL dichloromethane were cooled with an ice/ethanol bath and combined with 1.2 g (7.81 mmol) 5-chloro-2,3-dihydro-1H-indole. 7.9 mL (7.9 mmol) of a 1M sodium hydroxide solution were added dropwise. The reaction mixture was stirred for 2 h with cooling and for 1 h at RT. The man 50 mL of an aqueous saturated sodium hydrogen carbonate solution were added. After 10 min stirring the organic phase was separated off and washed with water and 1 M hydrochloric acid. The organic phases was dried on magnesium sulphate, filtered and evaporated down i.vac.
Yield: 2.0 g (80% of th.)
ESI-MS: m/z=294/296/298 (M+H)⁺
R_f (silica gel): 0.65 (eluant B)

Intermediate 8

6-Chloro-N-phenyl-N-(2,2,2-trifluoroethyl)pyrimidine-4-carboxamide

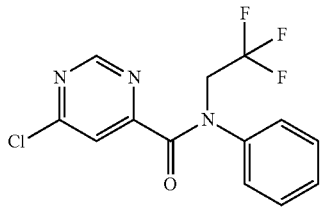

Step 1: N-(2,2,2-Trifluoroethyl)aniline

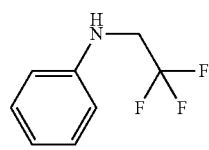

2.5 g (10.7 mmol) 2,2,2-trifluoroethyl trifluoromethanesulphonate were added to 2.0 g (21.5 mmol) aniline in 50 mL xylene and the mixture was refluxed for 2 days. After cooling, the mixture was filtered, washed with DIPE and the filtrate was evaporated down i.vac. The residue was purified by flash chromatography. The product fractions were combined and evaporated down i.vac.
Yield: 220 mg (6% of th.)
R_f (silica gel): 0.85 (eluant B)

Step 2: 6-Chloro-N-phenyl-N-(2,2,2-trifluoroethyl)pyrimidine-4-carboxamide

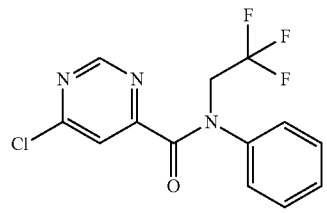

200 mg (1.14 mmol) N-(2,2,2-trifluoroethyl)aniline and 1.14 mL (1.14 mmol) of a 1M sodium hydroxide solution were added dropwise to 212 mg (1.2 mmol) 6-chloropyrimidine-4-carboxylic acid chloride in 20 mL dichloromethane while cooling with a bath of ice and ethanol. The mixture was first stirred for 2 h with cooling and then stirred for 1 h at RT. 50 mL of a saturated sodium hydrogen carbonate solution were added and the mixture was stirred for 10 min. The organic phase was separated off, washed with water and 1M hydrochloric acid, dried on sodium sulphate, filtered and concentrated by rotary evaporation i.vac.
Yield: 280 mg (74% of th.)
ESI-MS: m/z=316/318 [m+H]⁺
R_f (silica gel): 0.83 (eluant B)

Intermediate 9

N-benzyl-6-chloro-N-(2,2,2-trifluoroethyl)pyrimidine-4-carboxamide

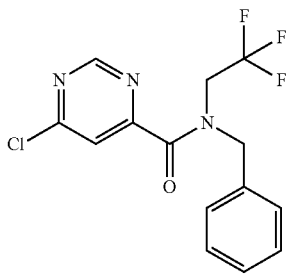

Step 1: benzyl-(2,2,2-trifluoroethyl)-amine

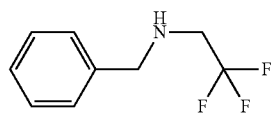

2.2 g (9.4 mmol) 2,2,2-trifluoroethyltrifluoromethanesulphonate were added to 2.0 g (18.7 mmol) benzylamine in 50 mL xylene and the reaction mixture was refluxed overnight. After cooling the precipitate formed was suction filtered, washed with DIPE and the filtrate was evaporated down using the rotary evaporator. The residue was purified by flash chromatography. The product fractions were combined and evaporated down i.vac.

Yield: 2.3 g (65% of th.)

ESI-MS: m/z=190.0 [m+H]$^+$

Step 2: N-benzyl-6-chloro-N-(2,2,2-trifluoroethyl) pyrimidine-4-carboxamide

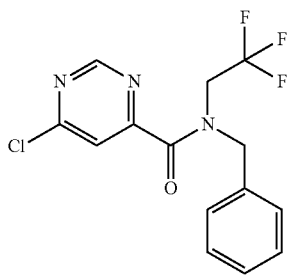

1.04 g (5.5 mmol) benzyl-(2,2,2-trifluoroethyl)-amine and 5.5 mL (5.5 mmol) of a 1M sodium hydroxide solution were added dropwise to 1.0 g (5.65 mmol) 6-chloropyrimidine-4-carboxylic acid chloride in 20 mL dichloromethane while cooling with a bath of ice and ethanol. The mixture was first stirred for 2 h with cooling and then for 1 h at RT. 50 mL of a saturated sodium hydrogen carbonate solution were added and the mixture was stirred for 10 min. The organic phase was separated off, washed with water and 1M hydrochloric acid, dried on sodium sulphate, filtered and evaporated down i.vac.

Yield: 1.2 g (64% of th.)

ESI-MS: m/z=330/332 [M+H]$^+$

R$_t$ (HPLC-MS): 1.56 min (Method C)

Intermediate 10

6-Chloro-N-phenethyl-N-(2,2,2-trifluoroethyl)pyrimidine-4-carboxamide

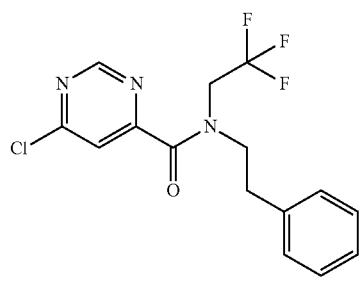

Step 1: phenethyl-(2,2,2-trifluoroethyl)-amine

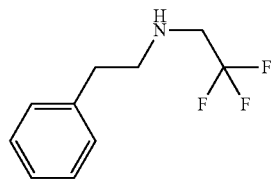

1.9 g (8.3 mmol) 2,2,2-trifluoroethyltrifluoromethanesulphonate were added to 2.0 g (16.5 mmol) phenethylamine in 50 mL xylene and the reaction mixture was refluxed overnight. After cooling the precipitate formed was suction filtered, washed with DIPE and the filtrate washed evaporated down i.vac. The residue was purified by flash chromatography. The product fractions were combined and evaporated down i.vac.

Yield: 0.8 g (24% of th.)

ESI-MS: m/z=204 [M+H]$^+$

R$_t$ (HPLC-MS): 1.61 min (Method C)

Step 2: 6-Chloro-N-phenethyl-N-(2,2,2-trifluoroethyl)pyrimidine-4-carboxamide

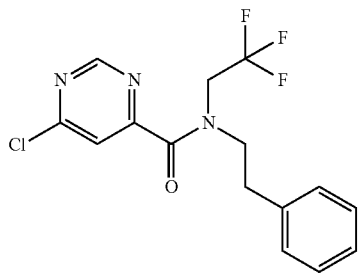

0.80 g (3.94 mmol) phenethyl-(2,2,2-trifluoroethyl)-amine and 3.9 mL (3.9 mmol) of a 1M sodium hydroxide solution were added dropwise to 0.77 g (4.33 mmol) 6-chloropyrimidine-4-carboxylic acid chloride in 20 mL dichloromethane while cooling with a bath of ice and ethanol. The mixture was first stirred for 2 h with cooling and then for 1 h at RT. 50 mL of a saturated sodium hydrogen carbonate solution were added and the mixture was stirred for 10 min. The organic phase was separated off, washed with water and 1M hydrochloric acid, dried on sodium sulphate, filtered and concentrated by rotary evaporation i.vac.

Yield: 1.0 g (67% of th.)

ESI-MS: m/z=344/346 [M+H]$^+$

R$_t$ (HPLC-MS): 1.58 min (Method C)

Intermediate 11

6-(2'-oxo-1',2',3-tetrahydrospiro[indene-2,3'-pyrrolo[2,3-b]pyridin]-5-ylamino)pyrimidine-4-carboxylic acid-hydrochloride

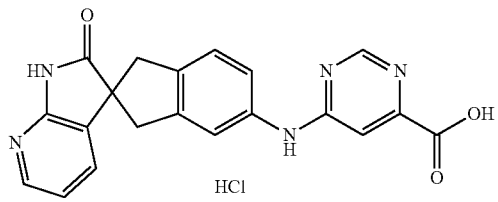

Step 1: ethyl 6-(2'-oxo-1,1',2',3-tetrahydrospiro[indene-2,3'-pyrrolo[2,3-b]pyridin]-5-ylamino)pyrimidine-4-carboxylate

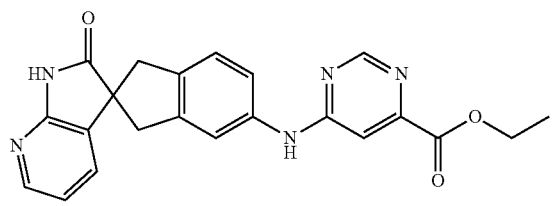

0.10 g (0.55 mmol) ethyl 6-chloropyrimidine-4-carboxylate and 13 µL (50 µmol) 4M HCl were added to 0.16 g (0.60 mmol) 5-amino-1,3-dihydrospiro[indene-2,3'-pyrrolo[2,3-b]pyridin]-2'(1'H)-one in 1.0 mL 2-propanol. The reaction mixture was refluxed for 2 h, then cooled to RT and the resulting solid was filtered off and dried.

Yield: 165 mg (54% of theory)
ESI-MS: m/z=402 (M+H)⁺

Step 2: 6-(2'-oxo-1,1',2',3-tetrahydrospiro[indene-2,3'-pyrrolo[2,3-b]pyridin]-5-yl-amino)pyrimidine-4-carboxylic acid-hydrochloride

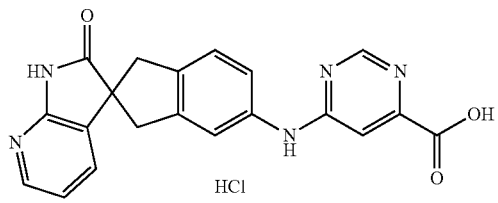

5.0 mL (5.0 mmol) of a 1M aqueous lithium hydroxide solution were added to 1.80 g (4.48 mmol) ethyl 6-(2'-oxo-1,1',2',3-tetrahydrospiro[indene-2,3'-pyrrolo[2,3-b]pyridin]-5-ylamino)pyrimidine-4-carboxylate in 5.0 mL ethanol and the mixture was stirred overnight at RT. The reaction mixture was acidified with 1.3 mL of a 4M aqueous HCl solution and the precipitate formed was suction filtered and dried.

Yield: 1.5 g (83% of theory)
ESI-MS: m/z=372 [M−H]⁻
R$_t$ (HPLC-MS): 1.85 min (method E)

Intermediate 12

4-(2'-oxo-1,1',2',3-tetrahydrospiro[indene-2,3'-pyrrolo[2,3-b]pyridin]-5-ylamino)-pyridine-2-carboxylic acid

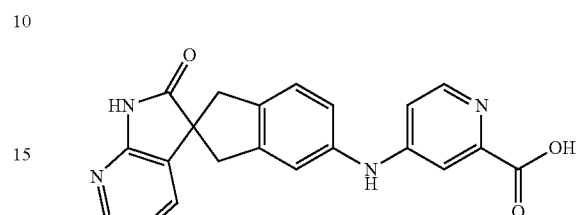

0.17 g (0.79 mmol) methyl 4-bromo-pyridine-2-carboxylate and 17 µL (70 µmol) of a 4M aqueous hydrochloric acid solution were added to 0.20 g (0.78 mmol) 5-amino-1,3-dihydrospiro[indene-2,3'-pyrrolo[2,3-b]pyridin]-2'(1'H)-one in 5.0 mL of 2-propanol. The reaction mixture was refluxed for 2 h, then cooled to RT and evaporated down. The residue was taken up in THF and mixed with 0.50 mL (2.0 mmol) of a 4M aqueous NaOH solution and stirred overnight at RT. The reaction mixture was diluted with water, combined with 0.5 mL conc. HCl and the solvent was eliminated. The precipitated product was suction filtered and dried.

Yield: 0.23 g (80% of theory)
ESI-MS: m/z=373 [M+H]⁺
R$_t$ (HPLC-MS): 0.96 min (method C)

Intermediate 13

4-(2'-oxo-1,1',2',3-tetrahydrospiro[indene-2,3'-pyrrolo[2,3-b]pyridin]-5-ylamino)-pyridine-3-carboxylic acid

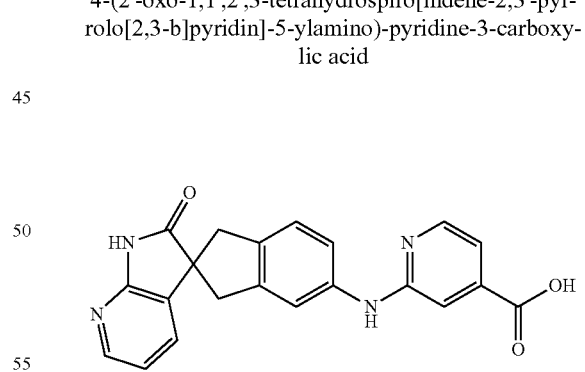

0.13 g (0.92 mmol) of 2-fluoropyridine-3-carboxylic acid and 20 µL (0.08 mmol) of a 4M aqueous HCl solution were added to 0.20 g (0.78 mmol) 5-amino-1,3-dihydrospiro[indene-2,3'-pyrrolo[2,3-b]pyridin]-2'(1'H)-one in 5.0 mL of 2-propanol. The reaction mixture was refluxed for 2 h, then cooled to RT and the resulting solid was filtered off and dried.

Yield: 110 mg (38% of theory)
ESI-MS: m/z=373 [m+H]⁺
R$_t$ (HPLC-MS): 1.01 min (method C)

Intermediate 14

4,4-dimethyl-4,5,6,7-tetrahydro-thieno[2,3-c]pyridine

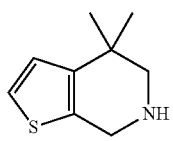

Step 1:
methylene-(2-methyl-2-thiophene-3-yl-propyl)-amine

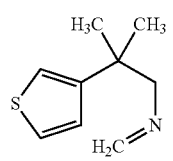

5.8 g (37 mmol) 2-methyl-2-thiophene-3-yl-propylamine and 3.6 mL (44 mmol) formaldehyde were stirred overnight together with 2.0 g molecular sieve (4 Å powder) at RT. The reaction mixture was filtered and the filtrate was concentrated to dryness by rotary evaporation.

Yield: 6.0 g (97% d. Th)

ESI-MS: m/z=168 (M+H)$^+$

Step 2: 4,4-dimethyl-4,5,6,7-tetrahydro-thieno[2,3-c]pyridine

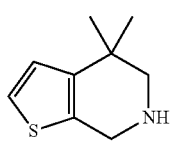

6.0 g (36 mmol) methylene-(2-methyl-2-thiophene-3-yl-propyl)-amine, 11 mL (45 mmol) 4M HCl and 12 mL (0.14 mol) conc. HCl were stirred at RT over the weekend. The reaction mixture was made alkaline with a 4M sodium hydroxide solution. The precipitate formed was suction filtered, washed with water and dried. The substance was purified on Alox. The product-containing fractions were combined and concentrated to dryness by rotary evaporation.

Yield: 0.74 g (12% d. Th)

R$_t$ (HPLC-MS): 1.24 min (method K)

Intermediate 15

7,7-dimethyl-4,5,6,7-tetrahydro-1H-pyrazolo[4,3-c]pyridine dihydrochloride

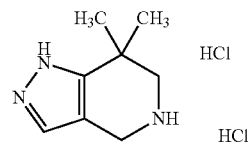

5 mL trifluoroacetic acid were added at 0° C. to 1.6 g (6.1 mmol) tert.butyl 7,7-dimethyl-1,4,6,7-tetrahydro-pyrazolo[4,3-c]pyridine-5-carboxylate in 15 mL dichloromethane and stirred for 2 h at RT. The reaction mixture was evaporated down. The residue was taken up in ethanol and mixed with 12 mL (15 mmol) 1.25 M ethanolic HCl and then evaporated down. The residue was triturated with ethanol and the solid was separated off by suction filtering and dried.

Yield: 1.2 g (92% of theory)

ESI-MS: m/z=152 [M+H]$^+$

Intermediate 16

(6-chloro-pyrimidin-4-yl)-(3-ethyl-6-fluoro-2,3-dihydro-indol-1-yl)-methanone

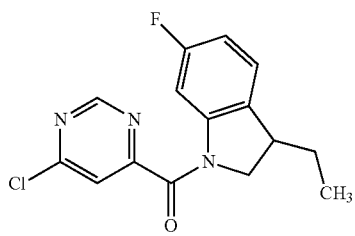

Step 1: 2-but-1-ynyl-5-fluoro-phenylamine

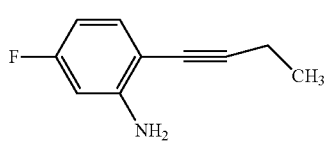

160 mL of THF were placed in the flask and degassed with argon. Then 10 g (45 mmol) 5-fluoro-2-iodo-aniline, 1.5 g (2.1 mmol) PdCl$_2$(PPh$_3$)$_2$ and 0.40 g (2.1 mmol) copper iodide were added and the flask was rinsed with argon. Then 18 mL (0.13 mol) triethylamine were added and 3.0 g (55 mmol) 1-butyne (in gaseous form) were passed through the solution. The reaction mixture was stirred for 3 h at RT, then diluted with diethyl ether, filtered through kieselguhr and evaporated down.

Yield: 6.90 g (quantitative)

Step 2: 2-ethyl-6-fluoro-1H-indole

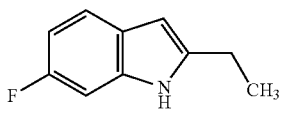

The reaction was carried out under an argon atmosphere. 21 g (0.13 mol) 2-but-1-ynyl-5-fluoro-phenylamine were added to 30 g (0.27 mol) potassium tert.butoxide in 120 mL N-methyl-2-pyrrolidinone and the mixture was stirred for 4 h at RT. The reaction mixture was mixed with water and extracted with diethyl ether. The organic phase was dried and evaporated down. The residue was purified on silica gel.

Yield: 16.25 g (78% of theory)
ESI-MS: m/z=164 [M+H]$^+$

Step 3: 2-ethyl-6-fluoro-2,3-dihydro-1H-indole

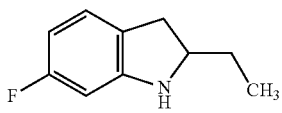

2.7 g (40 mmol) sodium cyanoborohydride were added to 1.6 g (10 mmol) 2-ethyl-6-fluoro-1H-indole in 20 mL conc. acetic acid and the mixture was stirred for 1 h at RT. The reaction mixture was evaporated down. The residue was mixed with 20 mL of a 4N HCl solution and stirred for 1 h at RT. Then 45 mL of a 4N sodium hydroxide solution was slowly added while cooling with ice and the mixture was extracted with ethyl acetate. The organic phase was dried on sodium sulphate and evaporated down.

Yield: 2.5 g (quantitative)
ESI-MS: m/z=166 [M+H]$^+$
R$_t$ (HPLC-MS): 1.32 min (method C)

Step 4: (6-chloro-pyrimidin-4-yl)-(2-ethyl-6-fluoro-2,3-dihydro-indol-1-yl)-methanone

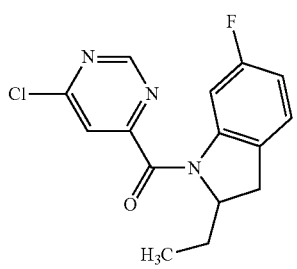

A mixture of 2.5 g (10 mmol) 2-ethyl-6-fluoro-2,3-dihydro-1H-indol in 25 mL dichloromethane was added at 0° C. to 1.8 g (10 mmol) 6-chloro-pyrimidine-4-carboxylic acid chloride in 25 mL dichloromethane and then 10 mL (10 mmol) of a 1M sodium hydroxide solution were added dropwise. The reaction mixture was stirred for 30 min at 0° C. and then for 1 h at RT. The organic phase was separated off and evaporated down. The residue was purified on silica gel.

Yield: 2.5 g (82% of theory)
ESI-MS: m/z=306 [m+H]$^+$
R$_t$ (HPLC-MS): 1.66 min (method C)

Intermediate 17

(6-chloro-pyrimidin-4-yl)-(2-propyl-2,3-dihydro-indol-1-yl)-methanone

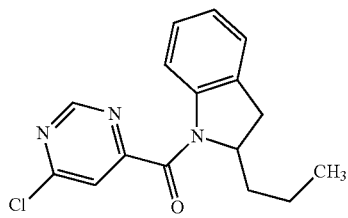

Step 1: 2-pent-1-ynyl-phenylamine

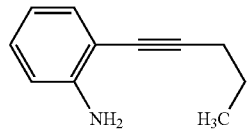

20 mL THF were placed in the flask and degassed with argon. Then 2.3 g (10 mmol) 2-iodo-aniline, 0.72 g (1.0 mmol) PdCl$_2$(PPh$_3$)$_2$ and 0.20 g (1.0 mmol) copper iodide were added and the flask was rinsed with argon. Then 4.2 mL (30 mmol) triethylamine and 1.5 mL (15 mmol) 1-pentyne were added. The reaction mixture was stirred for 3 h at RT, diluted with diethyl ether, filtered through kieselguhr and evaporated down.

Yield: 2.7 g (quantitative)

Step 2: 2-propyl-1H-indole

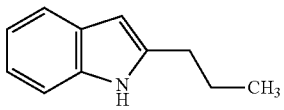

The reaction was carried out under an argon atmosphere. 2.7 g (10 mmol) 2-pent-1-ynyl-phenylamine were added to 2.3 g (20 mmol) potassium tert.butoxide in 50 mL of N-methyl-2-pyrrolidinone and the mixture was stirred overnight at RT. The reaction mixture was mixed with water and extracted with ethyl acetate. The organic phase was dried and evaporated down. The residue was purified on silica gel.

Yield: 1.2 g (75% of theory)
ESI-MS: m/z=160 [M+H]$^+$
R$_t$ (HPLC-MS): 1.60 min (method C)

Step 3: 2-propyl-2,3-dihydro-1H-indole

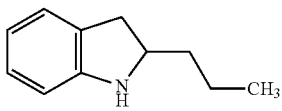

1.3 g (20 mmol) sodium cyanoborohydride were added to 0.75 g (4.7 mmol) 2-propyl-1H-indole in 10 mL conc. acetic acid and the mixture was stirred for 5 h at RT. The reaction mixture was evaporated down. The residue was mixed with 20 mL of a 4N HCl solution and stirred for 1 h at RT. Then 45 mL of a 4N sodium hydroxide solution was slowly added while cooling with ice and the mixture was extracted with ethyl acetate. The organic phase was dried on sodium sulphate and evaporated down.

Yield: 0.76 g (quantitative)
ESI-MS: m/z=162 [M+H]$^+$
R$_t$ (HPLC-MS): 1.50 min (method C)

Step 4: (6-chloro-pyrimidin-4-yl)-(2-propyl-2,3-dihydro-indol-1-yl)-methanone

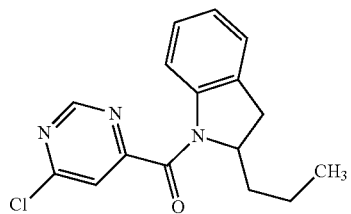

A mixture of 0.76 g (4.7 mmol) 2-propyl-2,3-dihydro-1H-indole in 15 mL dichloromethane was added to 0.88 g (5.0 mmol) 6-chloro-pyrimidine-4-carboxylic acid chloride in 15 mL dichloromethane at 0° C. and then 4.7 mL (4.7 mmol) of a 1M sodium hydroxide solution were added dropwise. The reaction mixture was stirred for 30 min at 0° C. and then for 1 h at RT. The organic phase was separated off and evaporated down. The residue was purified on silica gel.

Yield: 0.40 g (26% of theory)
ESI-MS: m/z=302 [M+H]$^+$
R$_t$ (HPLC-MS): 1.71 min (method C)

Intermediate 18

Spiro[piperidine-4,4'-pyrido[2,3-d][1,3]oxazin]-2'(1'H)-one hydrochloride

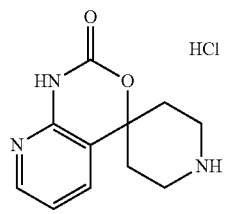

tert-butyl (6-chloro-pyridin-2-yl)-carbamate

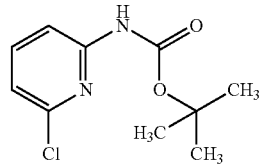

Under a nitrogen atmosphere a solution of 32.7 g (0.15 mol) BOC anhydride in 100 mL THF was added dropwise at RT to 17.4 g (0.14 mol) 6-chloro-pyridin-2-ylamine and 300 mL (0.30 mol) of a 1 molar sodium hexamethyldisilazide solution in THF in 200 mL THF. The reaction mixture was stirred overnight at RT and then evaporated down. The residue was stirred between EtOAc and 1N aqueous hydrochloric acid solution. The organic phase was separated off and the aqueous phase was again extracted with EtOAc. The combined organic phases were washed with 300 mL saturated sodium hydrogen carbonate solution, dried and evaporated down. The residue was recrystallised from EtOH, the solid was suction filtered and dried.

Yield: 29.2 g (95% of theoretical)
ESI-MS: m/z=228 (M+)
R$_t$(HPLC): 1.70 min (method C)

Step 2: benzyl 7'-chloro-2'-oxo-1',2'-dihydrospiro[piperidine-4,4'-pyrido[2,3d][1,3]-oxazin]-1-carboxylate

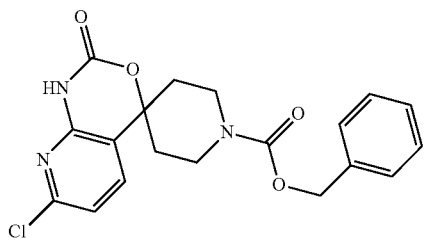

Under a nitrogen atmosphere 26 mL (1734 mmol) N,N,N,N-tetramethylenethylenediamine in 180 mL THF were cooled to −20° C. and 70 mL (175 mmol) of a 2.5 molar butyllithium solution were added within 10 min. After 30 minutes' stirring the reaction mixture was cooled to −78° C. and at this temperature 17.8 g (78.0 mmol) tert-butyl (6-chloro-pyridin-2-yl)-carbamate in 120 mL THF were added dropwise within 20 min. The reaction mixture was stirred for 2.5 h at −78° C. and then 27.2 g (116.7 mmol) benzyl 4-oxo-piperidine-1-carboxylate in 60 mL THF were added within 10 min. After another hour's stirring at −78° C. the reaction mixture was first of all heated to RT and then stirred for 18 h at 40° C. Then the reaction mixture was decomposed by the dropwise addition of 150 mL saturated sodium hydrogen carbonate solution. Then the reaction mixture was extracted several times with DCM. The combined organic phases were washed with water, dried and evaporated down. The residue was triturated with PE/EtOAc 1/1, the precipitate formed was suction filtered, washed with PE/ETOAc 1/1 and dried.

Yield: 16.4 g (54% of theoretical)
ESI-MS: m/z=388 (M+H)$^+$
R$_t$(HPLC): 1.57 min (method C)

Step 3: spiro[piperidine-4,4'-pyrido[2,3-d][1,3]ox-azin]-2'(1'H)-one hydrochloride

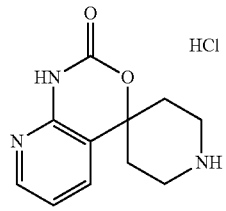

16.4 g (42.4 mmol) benzyl 7'-chloro-2'-oxo-1'.2'-dihydrospiro[piperidine-4,4'-pyrido[2,3d][1,3]oxazine]-1-carboxylate and 2.00 g palladium(Pd/C 10%) in 500 mL EtOH were hydrogenated in a hydrogen atmosphere for 6 h at RT. Then another 1.0 g palladium (Pd/C 10%) were added the mixture was hydrogenated for a further 3 h at RT in a hydrogen atmosphere. After filtration of the reaction mixture the solvent was eliminated in vacuo. The residue was triturated with EtOH, the precipitate formed was suction filtered, washed with EtOH and dried.

Yield: 5.40 g (50% of theoretical)
ESI-MS: m/z=220 (M+H)$^+$
$R_t$(HPLC): 0.90 min (method C)

Intermediate 19

(6-chloro-pyrimidin-4-yl)-(5-fluoro-2,3-dihydro-indol-1-yl)-methanone

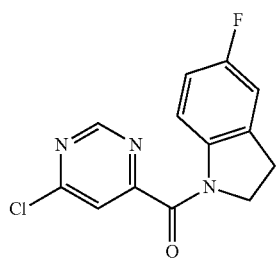

0.92 g (4.9 mmol) 6-chloro-pyrimidine-4-carboxylic acid chloride in 40 mL DCM were cooled in an ice/acetone bath and mixed with 0.67 g (4.9 mmol) 5-fluoro-2,3-dihydro-1H-indole. Another 5 mL (5.0 mmol) of a 1N aqueous sodium hydroxide solution were added dropwise and the mixture was stirred for 1 h with cooling. Then 50 mL of a saturated sodium hydrogen carbonate solution were added and the mixture was stirred for a further 10 min. The organic phase was separated off, extracted with 1N aqueous hydrochloric acid solution and with water, dried and evaporated down.

Yield: 0.81 mg (60% of theoretical)
ESI-MS: m/z=278 (M+H)$^+$
$R_t$(HPLC-MS): 1.50 min (method C)

Intermediate 20

2,3-dihydro-1H-indol-5-ol

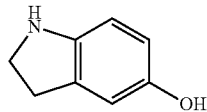

Under a nitrogen atmosphere 0.34 g sodium cyanoborohydride were added batchwise to 0.60 g (4.5 mmol) 5-hydroxyindole in 5.0 mL glacial acetic acid and the mixture was stirred for 60 min at RT. Then the reaction mixture was poured onto a 4N aqueous sodium hydroxide solution and extracted with EtOAc. The combined organic phases were washed several times with saturated sodium hydrogen carbonate solution, dried on sodium sulphate and evaporated down.

Yield: 265 mg (35% of theoretical)
ESI-MS: m/z=136 (M+H)$^+$
$R_t$ (HPLC-MS): 0.38 min (method C)

Intermediate 21

6-fluoro-2,3-dihydro-1H-indole

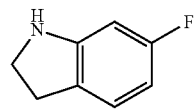

Under a nitrogen atmosphere 0.29 g (4.6 mmol) sodium cyanoborohydride were added batchwise to 0.54 g (4.0 mmol) 6-fluoroindole in 5.0 mL glacial acetic acid and the mixture was stirred for 30 min at RT. Then the reaction mixture was poured onto a 4N aqueous sodium hydroxide solution and extracted with EtOAc. The combined organic phases were washed several times with saturated sodium hydrogen carbonate solution, dried on sodium sulphate and evaporated down.

Yield: 0.56 g (97% of theoretical)
ESI-MS: m/z=138 (M+H)$^+$
$R_t$ (HPLC-MS): 0.74 min (method C)

Intermediate 22

(2-chloro-pyridin-4-yl)-(4,5-difluoro-2,3-dihydro-indol-1-yl)-methanone

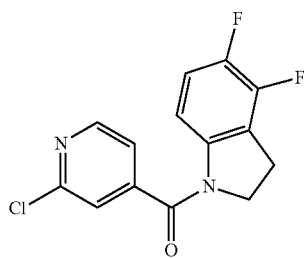

0.50 g (3.2 mmol) 2-chloroisonicotinic acid, 0.63 mg (3.3 mmol) 4,5-difluoroindoline-hydrochloride, 0.91 mL (6.5 mmol) TEA and 1.1 g (3.4 mmol) TBTU in 10 mL DMF were stirred overnight at RT. Then the reaction mixture was poured onto 200 mL of 15% potassium carbonate solution, the precipitate formed was suction filtered, washed with water and dried.

Yield: 0.90 g (96% of theory)
ESI-MS: m/z=295 (M+H)+
R$_t$ (HPLC-MS): 3.80 min (method E)

Intermediate 23

5,6-difluoro-2,3-dihydro-1H-indole

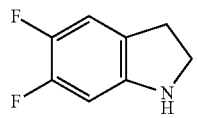

Under an argon atmosphere 0.30 g (1.8 mmol) 5,6-difluorooxindole were dissolved in 10 mL THF and 3.0 mL of a 1 molar borane solution in THF were added dropwise. Then the reaction mixture was heated to 70° C. for 2 h and then cooled. After mixing with 3 mL MeOH another 5 mL of a 4N aqueous hydrochloric acid solution were added and the mixture was refluxed for 1 h. The organic phase was evaporated down, the aqueous phase was washed with DCM and then made alkaline with a 4N aqueous sodium hydroxide solution and extracted several times with EtOAc. The combined organic phases were dried on sodium sulphate, filtered and evaporated down.

Yield: 160 mg (47% of theory)
ESI-MS: m/z=156 (M+H)+
R$_t$ (HPLC-MS): 0.73 min (method C)

Intermediate 24

3-methyl-2,3-dihydro-1H-indole

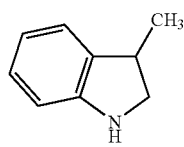

Under a nitrogen atmosphere 0.58 g (9.2 mmol) sodium cyanoborohydride were added batchwise to 1.0 g (7.6 mmol) 3-methylindole in 5.0 mL glacial acetic acid and the mixture was stirred for 60 min at RT. Then the reaction mixture was poured onto a 4N aqueous sodium hydroxide solution and extracted with EtOAc. The combined organic phases were washed several times with saturated sodium hydrogen carbonate solution, dried on sodium sulphate and evaporated down.

Yield: 1.2 g (83% of theoretical)
ESI-MS: m/z=134 (M+H)+
R$_t$ (HPLC-MS): 0.81 min (method C)

Intermediate 25

2,3-dihydro-1H-pyrrole[3,2-c]pyridine

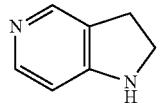

Step 1: (E)-3-(2-(dimethylamino)vinyl)-4-nitropyridine-1-oxide

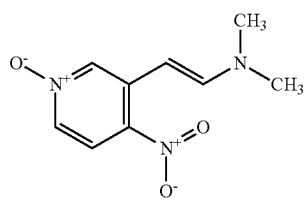

7.7 g (50 mmol) 3-methyl-4-nitropyridine-N-oxide and 8.0 mL (60 mmol) dimethylformamide dimethylacetal in 1.0 mL DMF were stirred at 120° C. for 4 h. Then the reaction mixture was concentrated by rotary evaporation, the residue was triturated with EtOH and precipitated from diethyl ether. The precipitate formed was suction filtered, washed with diethyl ether and dried.

Yield: 8.6 g (82% of theoretical)
ESI-MS: m/z=441 (2 M+Na)+
R$_f$: 0.4 (silica gel, EtOAc/EtOH 8:2)

Step 2: 1H-pyrrole[3,2-c]pyridine

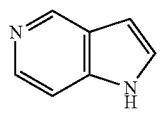

2.1 g (10 mmol) (E)-3-(2-(dimethylamino)vinyl)-4-nitropyridine-1-oxide in 25 mL EtOH were mixed with 3.2 g Raney nickel (50% in water) and hydrogenated in a 1 bar hydrogen atmosphere first of all for 3 h 15 min at RT and then for 2 h at 40° C. The catalyst was removed by suction filtering and the filtrate was purified with activated charcoal. Further purification was carried out by flash chromatography.

Yield: 0.90 g (76% of theoretical)
EI-MS: m/z=118 (M)+
R$_f$: 0.5 (silica gel, DCM/MeOH 2:3)

Step 3: 2,3-dihydro-1H-pyrrole[3,2-c]pyridine

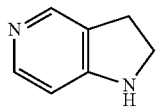

1.5 g (12.7 mmol) 1H-pyrrole[3,2-c]pyridine in 70 mL EtOH were combined with 0.75 g Raney nickel and hydrogenated for 3 days at 70° C. in a 3 bar hydrogen atmosphere. The catalyst was removed by suction filtering and the filtrate was evaporated down. The residue was purified by flash chromatography. The product-containing fractions were combined and evaporated down.

Yield: 0.62 g (41% of theoretical)
ESI-MS: m/z=121 (M+H)$^+$
$R_f$: 0.12 (silica gel, DCM/MeOH/NH$_4$OH 80:20:2)

Intermediate 26

(6-chloro-pyrimidin-4-yl)-(2-ethyl-2,3-dihydro-indol-1-yl)-methanone

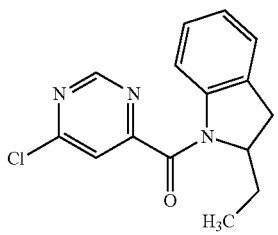

Step 1: 1-benzenesulphonyl-1H-indole

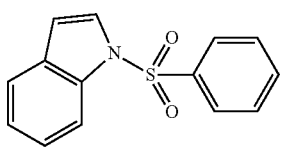

0.89 g (22.2 mmol) sodium hydride (60%) were added to 2.0 g (17.1 mmol) indole in 30 mL THF while cooling with an ice bath and the mixture was stirred for 15 min at this temperature. Then 2.2 mL (17.0 mmol) benzenesulphonic acid chloride were added and the mixture was stirred overnight at RT. The reaction mixture was combined with water and EtOAc and extracted several times with EtOAc. The combined organic phases were dried on sodium sulphate and evaporated down.

Yield: 4.6 g (quantitative)
ESI-MS: m/z=275 (M+H)$^+$

Step 2: 1-benzenesulphonyl-2-ethyl-1H-indole

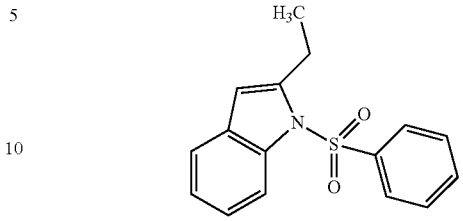

Under an argon atmosphere 6.7 mL (12 mmol) of a 1.8 molar lithium diisopropylamide solution in THF were slowly added dropwise to 2.8 g (11 mmol) 1-benzenesulphonyl-1H-indole in 25 mL of THF at −78° C. Then the cooling was removed, the reaction mixture was heated to RT and the mixture was stirred for a further hour at RT. The reaction mixture was cooled to −78° C. again and 1.0 mL (12 mmol) iodoethane were added. Then the reaction mixture was heated to RT again and stirred overnight. As the reaction was incomplete, the reaction mixture was again cooled to −78° C., mixed with 3.3 mL (6.0 mmol) of a 1.8 molar lithium diisopropylamide solution in THF and after the addition had ended it was heated to RT. Then the reaction mixture was poured onto ice water and extracted with EtOAc. The organic phase was dried on sodium sulphate and evaporated down. The residue was purified by flash chromatography. The product-containing fractions were combined, evaporated down and dried under HV.

Yield: 0.75 g (24% of theoretical)
$R_f$: 0.61 (silica gel, PE/EtOAc 3/1)

Step 3: 2-ethyl-1H-indole

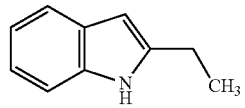

1.2 g (4.2 mmol) 1-benzenesulphonyl-2-ethyl-1H-indole in 10 mL EtOH were mixed with 5 mL of a (20 mmol) 4 N aqueous sodium hydroxide solution and refluxed for 8 h. Then the solvent was eliminated using the rotary evaporator and the residue was diluted with ice water. After acidifying with semi-concentrated aqueous hydrochloric acid the grease precipitated was extracted with ethyl acetate. The organic phase was dried on sodium sulphate, filtered off, evaporated down and dried.

Yield: 0.66 g (quantitative)
ESI-MS: m/z=146 (M+H)$^+$

Step 4: 2-ethyl-2,3-dihydro-1H-indole

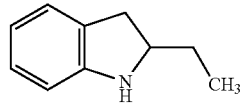

0.66 g (4.2 mmol) 2-ethyl-1H-indole in 10 mL acetic acid were mixed with 1.3 g (20 mmol) sodium cyanoborohydride and the mixture was stirred for one day at RT. The reaction mixture was evaporated down using the rotary evaporator, combined with 20 mL of 4N aqueous hydrochloric acid and stirred for 1 h at RT. While cooling with ice, 45 mL of a 4N aqueous sodium hydroxide solution were then added and the mixture was extracted with ethyl acetate. The organic phase was dried on sodium sulphate, filtered, evaporated down and the residue was dried in vacuo.

Yield: 0.80 g (quantitative)

(6-chloro-pyrimidin-4-yl)-(2-ethyl-2,3-dihydro-indol-1-yl)-methanone

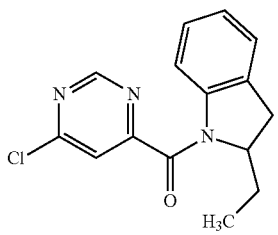

0.80 g (4.5 mmol) 6-chloropyrimidine-4-carboxylic acid chloride in 30 mL DCM were cooled in an ice/ethanol bath and mixed with 0.62 g (4.2 mmol) 2-ethyl-2,3-dihydro-1H-indole in DCM and 4.7 mL (4.7 mmol) of a 1 molar aqueous sodium hydroxide solution. Then the mixture was stirred for 30 min with cooling and for 1 h at RT. After the addition of 50 mL of a saturated sodium hydrogen carbonate solution the mixture was stirred for a further 10 min. The organic phase was separated off, washed with water and evaporated down. The residue was purified by flash chromatography. The product-containing fractions were combined, evaporated down and dried.

Yield: 0.25 g (19% of theoretical)

$R_f$: 0.54 (silica gel, PE/EtOAc 4/1)

Intermediate 27

6-chloro-2,3-dihydro-1H-indole

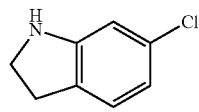

Under a nitrogen atmosphere 0.50 g (7.9 mmol) sodium cyanoborohydride were added batchwise to 1.0 g (6.6 mmol) 5-hydroxyindole in 5.0 mL glacial acetic acid and the mixture was stirred for 60 min at RT. Then the reaction mixture was poured onto a 4N aqueous sodium hydroxide solution and extracted with EtOAc. The combined organic phases were washed several times with saturated sodium hydrogen carbonate solution, dried on sodium sulphate and evaporated down.

Yield: 1.1 g (87% of theoretical)

$R_t$ (HPLC-MS): 1.24 min (method C)

Intermediate 28

2,3-dihydro-1H-indol-6-ole

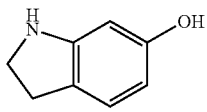

0.25 g (1.7 mmol) 6-methoxy-2,3-dihydro-1H-indole and 2.0 g (16.8 mmol) pyridine-hydrochloride were combined and heated to 350° C. for approx. 20 min. Then the reaction mixture was dissolved in acetonitrile/DMF and purified by preparative HPLC-MS. The product-containing fractions were combined and freeze-dried.

Yield: 50 mg (22% of theoretical)

$R_t$ (HPLC-MS): 0.94 min (method O)

Intermediate 29

(S)-2-(3,5-difluorophenyl)-5,5-dimethylpiperidine

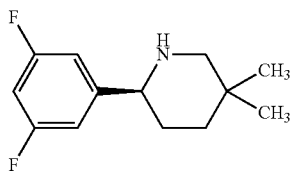

7.0 mL (7.0 mmol) of a 1 molar diisobutyl-aluminium hydride solution in toluene were added to 0.48 g (2.0 mmol) (S)-6-(3,5-difluorophenyl)-3,3-dimethylpiperidin-2-one in 10 mL THF while cooling with ice and the mixture was stirred for 20 h at RT. Then the reaction mixture was refluxed for 8 h. A 1 M diisobutylaluminium hdyride solution in toluene was added twice more and the mixture was refluxed for 8 h and 24 h, respectively. After hydrolysis of the reaction mixture the precipitate formed was suction filtered and washed with THF. The filtrate was evaporated down and the residue was purified by flash chromatography (aluminium oxide).

Yield: 0.40 g (53% of theoretical)

ESI-MS: m/z=226 (M+H)$^+$ and m/z=240 (M$_2$+H)$^+$ $R_t$ (HPLC-MS): 1.55 min (method C)

Intermediate 30

(2,3-dihydro-1H-indol-3-yl)-methanol

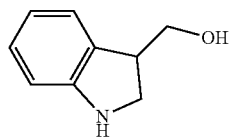

Step 1: ethyl 2,3-dihydro-1H-indol-3-carboxylate hydrochloride

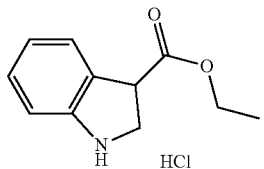

This compound was synthesised as described in WO 2007/054453.

Step 2: (2,3-dihydro-1H-indol-3-yl)-methanol

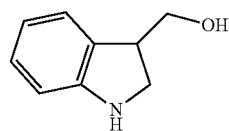

0.79 g (3.5 mmol) ethyl 2,3-dihydro-1H-indole-3-carboxylate were added batchwise at RT to 7.8 mL (7.8 mmol) of a 1 molar lithium aluminium hydride-THF solution in 40 mL THF and the mixture was refluxed for 1 h. Then the reaction mixture was decomposed with water, while cooling, the precipitate formed was filtered off and the filtrate was evaporated down.

Yield: 52 mg (95% of theoretical)
ESI-MS: m/z=150 (M+H)+
R$_t$ (HPLC-MS): 0.31 min (method P)

Intermediate 31

5,6,7,8-tetrahydro-4H-thiazol[4,5-d]azepine hydrochloride

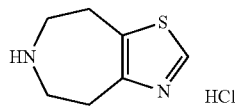

Step 1: ethyl 3-benzylamino-propionate

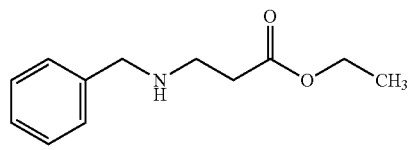

25 g (0.23 mol) benzylamine and 21 g (0.21 mol) ethyl acrylate in 125 mL EtOH were stirred for 15 h at RT. Then the solvent was evaporated down and the crude product was used in the next step without further purification.

Yield: 30 g (62% of theoretical)
ESI-MS: m/z=208 (M+H)+
R$_f$: 0.5 (silica gel, EtOAc/PE 50%)

Step 2: ethyl 4-[(benzyl-(2-ethoxycarbonyl-ethyl)-amino]-propanecarboxylate

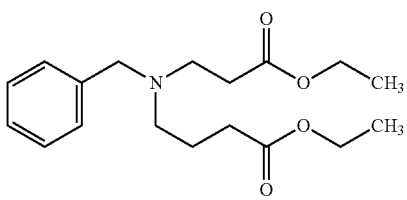

70.6 g (0.36 mol) ethyl 4-bromobutyrate were slowly added dropwise at RT to 50 g (0.24 mol) ethyl 3-benzylamino-propionate and 83 g (0.60 mol) potassium carbonate in 1.0 L acetonitrile. Then the reaction mixture was stirred for 12 h at 90° C. After cooling the reaction mixture was diluted with EtOAc and the organic phase was separated off. It was washed with water and saturated sodium chloride solution and then dried on sodium sulphate. After filtration the filtrate was evaporated down and the residue was purified by flash chromatography (on aluminium oxide).

Yield: 55.00 g (68% of theoretical)
R$_f$: 0.7 (silica gel, EtOAc/PE 2%)

Step 3: 1-benzyl-azepan-4-one

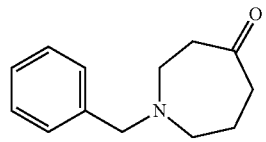

Under an argon atmosphere 1.0 L xylene were heated to 145° C. for 1 to 2 h using a Dean-Stark apparatus. Then the solvent was cooled to 65° C., mixed with 20.8 g (0.19 mol) potassium-tert-butoxide and heated to 145° C. for a further 1 to 2 h. Then 30 g (0.093 mol) ethyl 4-[benzyl-(2-ethoxycarbonyl-ethyl)-amino]-butyrate in xylene were added dropwise to the reaction mixture over a period of 1 h and the mixture was stirred at 145° C. for 2 to 3 h. After cooling to 0° C. the reaction mixture was combined with 0.45 L of a 6N aqueous hydrochloric acid solution, the aqueous phase was separated off and the mixture was refluxed for 2 h. Then it was cooled to 0° C. again, the reaction mixture was made alkaline with aqueous sodium hydroxide solution and extracted with EtOAc. The combined organic phases were dried on sodium sulphate, filtered and evaporated down. The residue was purified by flash chromatography (aluminium oxide).

Yield: 5.50 g (29% of theoretical)
ESI-MS: m/z=204 (M+H)+
R$_f$: 0.4 (silica gel, EtOAc/PE 30%)

Step 4: 1-benzyl-5-bromo-azepan-4-one hydrobromide

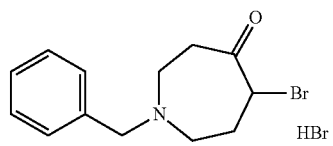

5.7 mL HBr in acetic acid (33%) were added dropwise at RT to 10 g (49 mmol) 1-benzyl-azepan-4-one in 28 mL acetic acid. Then another 9.5 g (60 mmol) bromine were added at RT and the mixture was stirred for 1.5 h at RT. After evaporation of the reaction mixture below 35° C. the residue was added to EtOAc and refluxed for approx. 1 h. The supernatant organic phase was decanted off from the precipitated solid, then mixed again with EtOAc and refluxed for approx. 1 h. The precipitated solid was filtered, washed with EtOAc and dried.

Yield: 6.0 g (34% of theoretical)
$R_f$: 0.6 (silica gel, EtOAc/PE 30%)

Step 5: 6-benzyl-5,6,7,8-tetrahydro-4H-thiazol[4,5-d]azepine hydrochloride

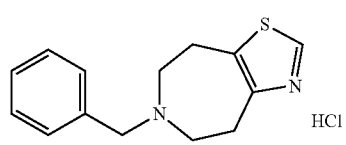

2.1 g (9.7 mmol) phosphorus pentasulphide and 1.9 g (41 mmol) formamide in dioxane were stirred for a total of 2.5 h at 100° C. After cooling to RT, 10 g (28 mmol) 1-benzyl-5-bromo-azepan-4-one hydrobromide were added and the mixture was stirred for 5 h at 100° C. Then the solvent was evaporated down, the residue was added to saturated sodium bicarbonate solution and extracted with EtOAc. The combined organic phases were washed with water, aqueous sodium bicarbonate solution and saturated sodium chloride solution. Then the organic phase was dried on sodium sulphate, filtered and evaporated down. The residue was purified by flash chromatography. The product-containing fractions were combined and evaporated down. The free base was combined with methanolic hydrochloric acid solution. The precipitate formed was filtered off.

Yield: 3.50 g (45% of theoretical)
ESI-MS: m/z=245 (M+H)$^+$
$R_f$: 0.5 (silica gel, MeOH/chloroform 10%)

Step 6: ethyl 4,5,7,8-tetrahydro-thiazol[4,5-d]azepine-6-carboxylate

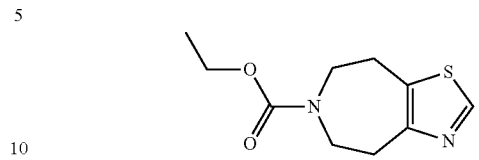

1.4 g (9.8 mmol) 1-chloroethylchloroformate were added dropwise at −20° C. to 2.0 g (8.2 mmol) 6-benzyl-5,6,7,8-tetrahydro-4H-thiazol[4,5-d]azepine in 100 mL DCM and the mixture was stirred for 30 min. Then the organic solvent was evaporated down and the residue was reacted further without any further purification.

Yield: 1.5 g (81% of theoretical)
$R_f$: 0.6 (silica gel, EtOAc/PE 20%)

Step 7: 5,6,7,8-tetrahydro-4H-thiazol[4,5-d]azepine hydrochloride

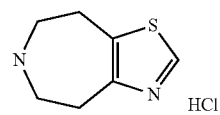

1.5 g (6.6 mmol) ethyl 4,5,7,8-tetrahydro-thiazol[4,5-d]azepine-6-carboxylate in 50 mL MeOH were refluxed for 3 h. After evaporation of the organic solvent the residue was purified by flash chromatography. The product-containing fractions were combined and evaporated down. The free base was combined with 5.0 mL (12.5 mmol) of a 2.5 molar methanolic hydrochloric acid solution and the excess solvent was evaporated down.

Yield: 0.70 g (55% of theoretical)
ESI-MS: m/z=155 (M+H)$^+$
$R_f$: 0.2 (silica gel, MeOH/chloroform 20%)

Intermediate 32

1,4,5,6,7,8-hexahydro-imidazo[4,5-d]azepine

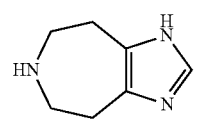

Step 1: 6-benzyl-1,4,5,6,7,8-hexahydro-imidazo[4,5-d]azepine

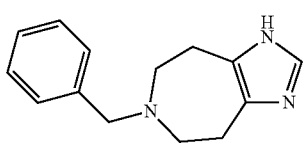

10 g (28 mmol) 1-benzyl-5-bromo-azepan-4-one hydrobromide, 11 g (83 mmol) potassium carbonate and 6.7 g (83 mmol) formamidine hydrochloride in 0.10 L MeOH were refluxed for 5 h. After cooling to RT the solvent was evaporated down and the residue was dissolved in DCM. The organic phase was washed with water, dried on sodium sulphate, filtered and evaporated down. The residue was purified by flash chromatography.

Yield: 1.5 g (24% of theoretical)
ESI-MS: m/z=228 (M+H)$^+$
$R_f$: 0.2 (silica gel, MeOH/DCM/NH$_3$ 2:8:0.1)

Step 2: 1,4,5,6,7,8-hexahydro-imidazo[4,5-d]azepine

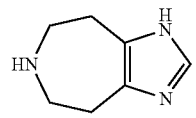

1.0 g (4.4 mmol) 6-benzyl-1,4,5,6,7,8-hexahydro-imidazo[4,5-d]azepine in EtOH were combined with 1.0 g palladium on charcoal (10%) and the mixture was hydrogenated for 15 h in a 75 psi hydrogen atmosphere. The catalyst was removed by suction filtering and the filtrate was evaporated down. The residue was washed with acetonitrile and then dried.

Yield: 0.35 g (58% of theoretical)
ESI-MS: m/z=138 (M+H)$^+$
$R_f$: 0.1 (silica gel, MeOH/DCM/NH$_3$ 2:8:0.1)

Intermediate 33 but-3-ynyl-methyl-amine

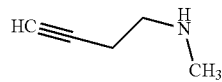

9.0 mL (51 mmol) 3-butyn-p-toluenesulphonate in 24 mL (0.31 mol) of a 40% aqueous methylamine solution were heated for 10 min in the microwave. The reaction mixture was extracted with water/potassium carbonate solution and DCM. The organic phase was dried and evaporated down.

Yield: 2.70 g (64% of theoretical)

Preparation of the End Compounds

Example 1

5-(6-(indoline-1-carbonyl)pyrimidin-4-ylamino)-1,3-dihydrospiro[indene-2,3'-pyrrolo[2,3-b]pyridin]-2'(1'H)-one 100 mg (0.40 mmol) 5-amino-1,3-dihydrospiro[indene-2,3'-pyrrolo[2,3-b]pyridin]-2'(1'H)-one were added to 100 mg (0.39 mmol) (6-chloro-pyrimidin-4-yl)-(2,3-dihydro-indol-1-yl)-methanone and 100 μL (0.58 mmol) DIPEA in 10 mL DMF. The reaction mixture was stirred over the weekend at 100° C. The reaction mixture was concentrated by rotary evaporation using the rotary evaporator. The residue was mixed with water and the product precipitated was suction filtered. The precipitate was dissolved in DMF and purified by preparative HPLC. The product fractions were combined and lyophilised.

Yield: 2.0 mg (1% of th.)
ESI-MS: m/z=475 (M+H)$^+$
$R_f$ (silica gel): 0.46 (eluant A)

General working method 1 (GMW1) for reacting (6-chloro-pyrimidin-4-yl)-(2,3-dihydro-indol-1-yl)-methanone with amine derivatives:

0.41 mmol of an amine derivative were added to 100 mg (0.39 mmol) of (6-chloro-pyrimidin-4-yl)-(2,3-dihydro-indol-1-yl)-methanone and in the case of AA1 [A] 100 μL (0.58 mmol) DIPEA and in the case of AA1 [B] 150 μL (0.87 mmol) DIPEA in 10 mL DMF. The reaction mixture was stirred for 2 h at RT. The reaction mixture was evaporated down using the rotary evaporator and the residue was mixed with 20 mL water and stirred for 30 min at RT. The product precipitated was suction filtered, stirred with diisopropylether and isopropanol, suction filtered again and dried.

| Example Method | Structure | Amine derivative [amount of amine derivative] Yield | Analytical data |
|---|---|---|---|
| Example 2: GWM1 [A] | 1-(6-(indoline-1-carbonyl)pyrimidin-4-yl)-1'H-spiro[piperidin-4,4'-quinazolin]-2'(3'H)-one | 1'H-spiro[piperidine-4,4'-quinazolin]-2'(3'H)-one 90 mg (0.41 mmol) 150 mg (88% of theory) | ESI-MS: m/z = 441 [M + H]$^+$ $R_f$: 0.54 eluant A |

| Example Method | Structure | Amine derivative [amount of amine derivative] Yield | Analytical data |
|---|---|---|---|
| Example 3: GWM1 [B] | 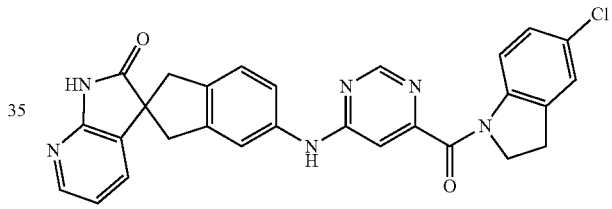<br><br>1'-(6-(indoline-1-carbonyl)pyrimidin-4-yl)spiro[benzo[d][1,3]-oxazine-4,4'-piperidin]-2(1H)-one | spiro[benzo[d]-[1,3]oxazine-4,4'-piperidin]-2(1H)-one hydrochloride 105.0 mg (0.41 mmol) 50 mg (29% of theory) | ESI-MS: m/z = 442 [M + H]+ $R_f$: 0.52 eluant A |

Example 4

1-(6-(indoline-1-carbonyl)pyrimidin-4-yl)spiro[piperidine-4,3'-pyrrolo[2,3-b]pyridin]-2'(1'H)-one

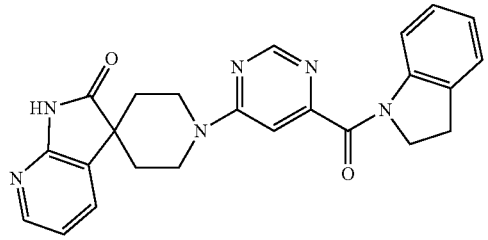

43 mg (0.21 mmol) spiro[piperidine-4,3'-pyrrolo[2,3-b]pyridin]-2'(1'H)-one were added to 50 mg (0.19 mmol) (6-chloro-pyrimidin-4-yl)-(2,3-dihydro-indol-1-yl)-methanone and 52 μL (0.58 mmol) DIPEA in 5 mL DMF. The reaction mixture was stirred for 2 h at RT. The reaction mixture was evaporated down using the rotary evaporator and the residue was mixed with 20 mL water and stirred for 30 min at RT. The product precipitated was suction filtered, stirred with diisopropylether and isopropanol, suction filtered and dried.

Yield: 38 mg (46% of th.)
ESI-MS: m/z=427 (M+H)+
$R_t$ (HPLC-MS): 3.3 min (Method H)

Example 5

5-(6-(5-Chlorindoline-1-carbonyl)pyrimidin-4-ylamino)-1,3-dihydrospiro[indene-2,3'-pyrrolo[2,3-b]pyridin]-2'(1'H)-one 90 mg (0.36 mmol) 5-amino-1,3-dihydrospiro[indene-2,3'-pyrrolo[2,3-b]pyridin]-2'(1'H)-one were added to 100 mg (0.34 mmol) (5-chloro-2,3-dihydro-indol-1-yl)-(6-chloro-pyrimidin-4-yl)-methanone and 100 μL (0.58 mmol) DIPEA in 10 mL DMF. The reaction mixture was stirred over the weekend at 100° C. The reaction mixture was evaporated down using the rotary evaporator and the residue was mixed with water. The product precipitated was suction filtered and dissolved in DMF. Purification was carried out using preparative HPLC. The product fractions were combined and lyophilised.

Yield: 2.0 mg (1% of th.)
ESI-MS: m/z=509/511 (M+H)+
$R_f$ (silica gel): 0.50 (eluant A)

General working method 2 (GWM2) for reacting 6-chloro-N-(2,2,2-trifluoroethyl)pyrimidine-4-carboxamide derivatives with 5-amino-1,3-dihydrospiro[indene-2,3'-pyrrolo[2,3-b]-pyridin]-2'(1'H)-one:

5.1 mg (0.032 mmol) benzenesulphonic acid were added to 50 mg of the 6-chloro-N-(2,2,2-trifluoroethyl)pyrimidine-4-carboxamide derivative and 45.2 mg of 5-amino-1,3-dihydrospiro[indene-2,3'-pyrrolo[2,3-b]pyridin]-2'(1'H)-one in 5 mL of 2-pentanol. The reaction mixture was refluxed overnight. The reaction mixture was evaporated down using the rotary evaporator and the residue was taken up in DMF. Purification was carried out using preparative HPLC. The product fractions were combined and lyophilised.

| Example Method | Structure | Carboxamide [amount of carboxamide derivative] yield | Analytical data |
|---|---|---|---|
| Example 6: GWM2 | 6-(2'-oxo-1,1',2',3-tetrahydro-spiro[indene-2,3'-pyrrolo[2,3-b]-pyridin]-5-ylamino)-N-phenyl-N-(2,2,2-trifluoroethyl)pyrimidine-4-carboxamide | 6-chloro-N-phenyl-N-(2,2,2-trifluoroethyl)-pyrimidine-4-carboxamide 50 mg (0.16 mmol) 13 mg (16% of theory) | ESI-MS: m/z = 531 [M + H]$^+$ R$_t$: 1.34 min (method C) |
| Example 7: GWM2 | N-benzyl-6-(2'-oxo-1,1',2',3-tetrahydrospiro[indene-2,3'-pyrrolo[2,3-b]pyridin]-5-ylamino)-N-(2,2,2-trifluoroethyl)pyrimidine-4-carboxamide | N-benzyl-6-chloro-N-(2,2,2-trifluoroethyl)-pyrimidine-4-carboxamide 50 mg (0.15 mmol) 7 mg (9% of theory) | ESI-MS: m/z = 545 [M + H]$^+$ R$_t$: 3.81 min (method E) |
| Example 8: GWM2 | 6-(2'-oxo-1,1',2',3-tetrahydro-spiro[indene-2,3'-pyrrolo[2,3-b]-pyridin]-5-ylamino)-N-phenethyl-N-(2,2,2-trifluoroethyl)pyrimidine-4-carboxamide | 6-chloro-N-phenethyl-N-(2,2,2-trifluoroethyl)-pyrimidine-4-carboxamide 50 mg (0.15 mmol) 41 mg (51% of theory) | ESI-MS: m/z = 559 [M + H]$^+$ R$_t$: 3.92 min (method K) |

Example 9

5'-(6-(indoline-1-carbonyl)pyrimidin-4-ylamino)-3-methyl-1',3'-dihydrospiro[imidazolidin-4,2'-inden]-2,5-dione

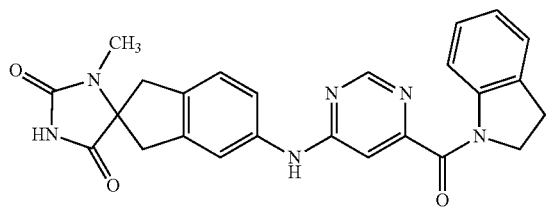

80.0 mg (0.23 mmol) 6-(3-methyl-2,5-dioxo-1',3'-dihydrospiro[imidazolidin-4,2'-inden]-5'-ylamino)pyrimidine-4-carboxylic acid, 30 μL (0.27 mmol) 2,3-dihydro-1H-indole, 70 μL (0.50 mmol) triethylamine and 80.0 mg (0.25 mmol) TBTU in 1.5 mL DMF were stirred for 4 h at RT. The reaction mixture was filtered through a syringe filter and purified by preparative HPLC. The product fractions were combined, concentrated by rotary evaporation and dried.

Yield: 35 mg (34% of th.)
ESI-MS: m/z=455 (M+H)$^+$
$R_f$ (silica gel): 0.30 (eluant A)

Example 10

5-(6-(2-ethyl-6-fluorindoline-1-carbonyl)pyrimidin-4-ylamino)-1,3-dihydrospiro[indene-2,3'-pyrrolo[2,3-b]pyridin]-2'(1'H)-one

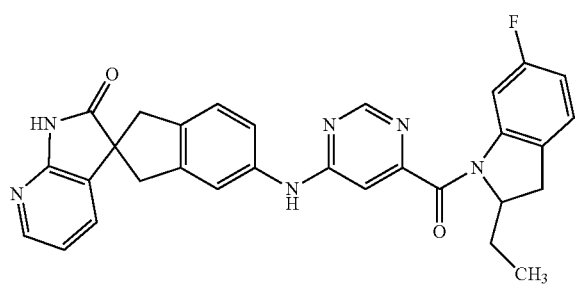

63 μL (0.25 mmol) 4M aqueous hydrochloric acid were added to 516 mg (2.00 mmol) (6-chloro-pyrimidin-4-yl)-(2-ethyl-6-fluoro-2,3-dihydro-indol-1-yl)-methanone and 611 mg (2.00 mmol) 5-amino-1,3-dihydrospiro[indene-2,3'-pyrrolo[2,3-b]pyridin]-2'(1'H)-one in 10 mL of 2-pentanol. The reaction mixture was refluxed for 6 h. The reaction mixture was evaporated down using the rotary evaporator and the residue was taken up in DMF. The purification was carried out by preparative HPLC. The product fractions were combined and lyophilised.

Yield: 650 mg (62% of theory)
ESI-MS: m/z=521 [m+H]$^+$
$R_t$ (HPLC-MS): 1.60 min (method C)

Example 11

5-(6-(2-propylindoline-1-carbonyl)pyrimidin-4-ylamino)-1,3-dihydrospiro[indene-2,3'-pyrrolo[2,3-b]pyridin]-2'(1'H)-one

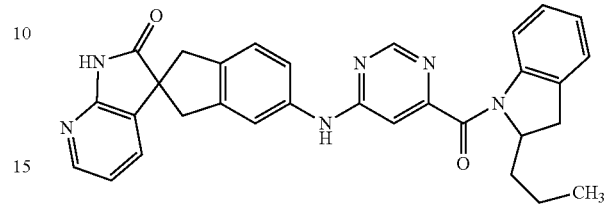

12.5 μL (50 μmol) 4M aqueous hydrochloric acid were added to 103 mg (0.40 mmol) (6-chloro-pyrimidin-4-yl)-(2-propyl-2,3-dihydro-indol-1-yl)-methanone and 108 mg (0.36 mmol) 5-amino-1,3-dihydrospiro[indene-2,3'-pyrrolo[2,3-b]pyridin]-2'(1'H)-one in 2 mL 2-pentanol. The reaction mixture was refluxed for 2 h. The reaction mixture was evaporated down using the rotary evaporator and the residue was taken up in DMF. The purification was carried out by preparative HPLC. The product fractions were combined and lyophilised.

Yield: 90 mg (43% of theory)
ESI-MS: m/z=517 [M+H]$^+$
$R_t$ (HPLC-MS): 1.55 min (method C)

Example 12

5-(6-(4,4-dimethyl-4,5,6,7-tetrahydrothieno[2,3-c]pyridine-6-carbonyl)pyrimidin-4-ylamino)-1,3-dihydrospiro[indene-2,3'-pyrrolo[2,3-b]pyridin]-2'(1'H)-one

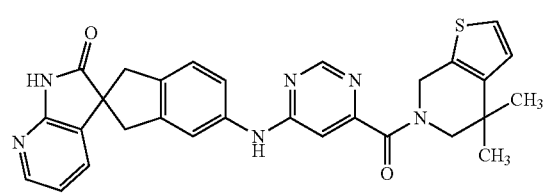

86 mg (0.21 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 40 mg (0.24 mmol) 4,4-dimethyl-4,5,6,7-tetrahydro-thieno[2,3-c]pyridine, 68 μL (0.48 mmol) triethylamine and 77 mg (0.24 mmol) TBTU in 1.0 mL DMF were stirred for 4 h at RT. The reaction mixture was purified by preparative HPLC. The product fractions were combined, evaporated down, suction filtered and then washed with water. The product was dried.

Yield: 39 mg (35% of theory)
ESI-MS: m/z=523 [m+H]$^+$
$R_t$ (HPLC-MS): 3.49 min (method E)

General working method 3 (GWM3) for reacting 6-(2'-oxo-1,1',2',3-tetrahydrospiro[indene-2,3'-pyrrolo[2,3-b]pyridin]-5-ylamino)pyrimidine-4-carboxylic acid hydrochloride with amine derivatives:

1.1 equivalents (0.24 mmol) of the amine derivative, 2 to 5 equivalents triethylamine and 1.1 equivalents (0.24 mmol) TBTU were added to 86 mg (0.21 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride in 1 mL DMF and the mixture was stirred for 4 h at RT. The purification was carried out by preparative HPLC. The product fractions were combined and lyophilised. The following compounds were able to be synthesised analogously to this working method:

| Example Method | Structure | Amine derivative [amount of amine derivative] Yield | Analytical data |
| --- | --- | --- | --- |
| Example 13: GWM3 | 5-(6-(5-fluoroindoline-1-carbonyl)-pyrimidin-4-ylamino)-1,3-dihydro-spiro[indene-2,3'-pyrrolo[2,3-b]pyridin]-2'(1'H)-one | 5-fluoro-2,3-dihydro-1H-indol 33 mg (0.24 mmol) 12 mg (12% of theory) | ESI-MS: m/z = 493 [M + H]⁺ R$_t$: 3.46 min (method E) |
| Example 14: GWM3 | 5-(6-(4,4-dimethyl-1,2,3,4-tetra-hydroisoquinoline-2-carbonyl)pyrimidin-4-ylamino)-1,3-dihydrospiro[indene-2,3'-pyrrolo[2,3-b]pyridin]-2'(1'H)-one | 4,4-dimethyl-1,2,3,4-tetrahydro-isoquinoline-hydrochloride 47 mg (0.24 mmol) 11 mg (10% of theory) | ESI-MS: m/z = 517 [M + H]⁺ R$_t$: 3.51 min (method E) |
| Example 15: GWM3 | 5-(6-(4,5-difluoroindoline-1-carbonyl)pyrimidin-4-ylamino)-1,3-dihydrospiro[indene-2,3'-pyrrolo[2,3-b]pyridin]-2'(1'H)-one | 4,5-difluoro-2,3-dihydro-1H-indole hydrochloride 45.8 mg (0.24 mmol) 55 mg (51% of theory) | ESI-MS: m/z = 511 [M + H]⁺ R$_t$: 3.68 min (method E) |
| Example 16 GWM3 | 5-(6-(2-oxo-1,2,5,6,7,8-hexahydro-1,6-naphthyridine-6-carbonyl)pyrimidin-4-ylamino)-1,3-dihydrospiro[indene-2,3'-pyrrolo[2,3-b]pyridin]-2'(1'H)-one | 5,6,7,8-tetrahydro-1H-[1,6] naphthyridin-2-one 40 mg (0.27 mmol) 25 mg (24% of theory) | ESI-MS: m/z = 506 [M + H]⁺ R$_t$: 2.12 min (method E) |

-continued

| Example Method | Structure | Amine derivative [amount of amine derivative] Yield | Analytical data |
|---|---|---|---|
| Example 17: GWM3 | N-(1H-indazol-4-yl)-6-(2'-oxo-1,1',2',3-tetrahydrospiro[indene-2,3'-pyrrolo[2,3-b]pyridin]-5-ylamino)pyrimidine-4-carboxamide | 1H-indazol-4-ylamine 32 mg (0.24 mmol) 10 mg (8% of theory) | ESI-MS: m/z = 489 [M + H]⁺ $R_t$: 1.24 min (method C) |
| Example 18: GWM3 | 5-(6-(7,7-dimethyl-4,5,6,7-tetrahydro-1H-pyrazolo[4,3-c]pyridine-5-carbonyl)pyrimidin-4-ylamino)-1,3-dihydrospiro[indene-2,3'-pyrrolo[2,3-b]pyridin]-2'(1'H)-one | 7,7-dimethyl-4,5,6,7-tetrahydro-1H-pyrazolo[4,3-c]-pyridine dihydrochloride 54 mg (0.24 mmol) 6 mg (6% of theory) | ESI-MS: m/z = 507 [M + H]⁺ $R_t$: 2.43 min (method E) |
| Example 19: GWM3 method was carried out in 2 mL DMF | 5-(6-(1,2,3,4-tetrahydropyrrolo[1,2-a]pyrazine-2-carbonyl)pyrimidin-4-ylamino)-1,3-dihydrospiro[indene-2,3'-pyrrolo[2,3-b]pyridin]-2'(1'H)-one | 1,2,3,4-tetrahydro-pyrrolo[1,2-a]-pyrazine 37 mg (0.24 mmol) 59 mg (59% d.Th | ESI-MS: m/z = 478 [M + H]⁺ $R_t$: 1.29 min (method C) |

General working method 4 (GWM4) for reacting 2-(2'-oxo-1,1',2',3-tetrahydrospiro[indene-2,3'-pyrrolo[2,3-b]pyridin]-5-ylamino)isonicotinic acid with amine derivatives:

1.1 equivalents (0.30 mmol) of the amine derivative, 1.3 to 5 equivalents triethylamine and 1 equivalent (0.28 mmol) TBTU were added to 0.10 g (0.27 mmol) 2-(2'-oxo-1,1',2',3-tetrahydrospiro[indene-2,3'-pyrrolo[2,3-b]pyridin]-5-ylamino)isonicotinic acid in 3.0 mL DMF and the mixture was stirred for 4 h at RT. The purification was carried out by preparative HPLC. The product fractions were combined and lyophilised. The following compounds were able to be synthesised analogously to this working method:

| Example Method | Structure | Amine derivative [amount of amine derivative] Yield | Analytical data |
|---|---|---|---|
| Example 20: GWM4 | 5-(4-(indoline-1-carbonyl)pyridin-2-ylamino)-1,3-dihydrospiro[indene-2,3'-pyrrolo[2,3-b]pyridin]-2'(1'H)-one | 2,3-dihydro-1H-indole 34 μL (0.30 mmol) 50 mg (39% of theory) | ESI-MS: m/z = 474 [M + H]⁺ R$_t$: 1.27 min (method C) |
| Example 21: GWM4 | 5-(4-(4-fluoroindoline-1-carbonyl)pyridin-2-ylamino)-1,3-dihydrospiro[indene-2,3'-pyrrolo[2,3-b]pyridin]-2'(1'H)-one | 4-fluoro-2,3-dihydro-1H-indole 40 mg (0.29 mmol) 50 mg (38% of theory) | ESI-MS: m/z = 492 [M + H]⁺ R$_t$: 1.31 min (method C) |
| Example 22: GWM4 | 5-(4-(5-fluoroindoline-1-carbonyl)pyridin-2-ylamino)-1,3-dihydrospiro[indene-2,3'-pyrrolo[2,3-b]pyridin]-2'(1'H)-one | 5-fluoro-2,3-dihydro-1H-indole 40 mg (0.29 mmol) 45 mg (34% of theory) | ESI-MS: m/z = 492 [M + H]⁺ R$_t$: 1.28 min (method C) |
| Exmple 23: GWM4 | 5-(4-(4,5-difluoroindoline-1-carbonyl)pyridin-2-ylamino)-1,3-dihydrospiro[indene-2,3'-pyrrolo[2,3-b]pyridin]-2'(1'H)-one | 4,5-difluoro-2,3-dihydro-1H-indole hydrochloride 55 mg (0.29 mmol) 50 mg (37% of theory) | ESI-MS: m/z = 510 [M + H]⁺ R$_t$: 1.35 min (method C) |

| Example Method | Structure | Amine derivative [amount of amine derivative] Yield | Analytical data |
|---|---|---|---|
| Example 24: GWM4 | 5-(4-(3-methylindoline-1-carbonyl)pyridin-2-ylamino)-1,3-dihydrospiro[indene-2,3'-pyrrolo[2,3-b]pyridin]-2'(1'H)-one | 3-methyl-2,3-dihydro-1H-indole 40 mg (0.30 mmol) 45 mg (34% of theory) | ESI-MS: m/z = 488 [M + H]⁺ R$_t$: 1.33 min (method C) |
| Example 25: GWM4 | 5-(4-(5-hydroxyindoline-1-carbonyl)pyridin-2-ylamino)-1,3-dihydrospiro[indene-2,3'-pyrrolo[2,3-b]pyridin]-2'(1'H)-one | 2,3-dihydro-1H-indol-5-ol 50 μL (0.36 mmol) 65 mg (49% of theory) | ESI-MS: m/z = 490 [M + H]⁺ R$_t$: 1.15 min (method C) |
| Example 26: GWM4 (this method was carried out with 0.17 mmol educt in 1.8 mL DMF) | 1-(2-(2'-oxo-1,1',2',3-tetrahydrospiro[indene-2,3'-pyrrolo[2,3-b]pyridin]-5-ylamino)isonicotinoyl)-1,2,2a,3-tetrahydropyrrolo[4,3,2-de]quinolin-4(5H)-one | 1,2,2a,5-tetrahydro-3H-pyrrolo[4,3,2-de]quinolin-4-one 30 mg (0.17 mmol) 30 mg (33% of theory) | ESI-MS: m/z = 529 [M + H]⁺ R$_t$: 2.87 min (method E) |

General working method 5 (GWM5) for reacting 4-(2'-oxo-1,1',2',3-tetrahydrospiro[indene-2,3'-pyrrolo[2,3-b]pyridin]-5-ylamino)picolinic acid with amine derivatives:

1.1 equivalents (0.30 mmol) of the amine derivative, 1.3 to 5 equivalents triethylamine and 1 equivalent (0.28 mmol) TBTU were added to 0.10 mg (0.27 mmol) 4-(2'-oxo-1,1',2', 3-tetrahydrospiro[indene-2,3'-pyrrolo[2,3-b]pyridin]-5-ylamino)picolinic acid in 3.0 mL DMF and the mixture was stirred for 4 h at RT. The purification was carried out by preparative HPLC. The product fractions were combined and lyophilised. The following compounds were able to be synthesised analogously to this working method:

| Example Method | Structure | Amine derivative [amount of amine derivative] Yield | Analytical data |
|---|---|---|---|
| Example 27: GWM5 | 5-(2-indoline-1-carbonyl)pyridin-4-ylamino)-1,3-dihydrospiro-[indene-2,3'-pyrrolo[2,3-b]pyridin]-2'(1'H)-one | 2,3-dihydro-1H-indole 34 µL (0.30 mmol) 80 mg (63% of theory) | ESI-MS: m/z = 474 [M + H]$^+$ R$_t$: 1.10 min (method C) |
| Example 28: GWM5 | 5-(2-(4-fluoroindoline-1-carbonyl)pyridin-4-ylamino)-1,3-dihydrospiro[indene-2,3'-pyrrolo[2,3-b]pyridin]-2'(1'H)-one | 4-fluoro-2,3-dihydro-1H-indole 40 mg (0.29 mmol) 65 mg (49% of theory) | ESI-MS: m/z = 492 [M + H]$^+$ R$_t$: 1.14 min (method C) |
| Example 29: GWM5 | 5-(4-(5-fluoroindoline-1-carbonyl)pyridin-2-ylamino)-1,3-dihydrospiro[indene-2,3'-pyrrolo[2,3-b]pyridin]-2'(1'H)-one | 5-fluoro-2,3-dihydro-1H-indole 40 mg (0.29 mmol) 55 mg (42% of theory) | ESI-MS: m/z = 492 [M + H]$^+$ R$_t$: 1.13 min (method C) |
| Example 30: GWM5 | 5-(2-(4,5-difluoroindoline-1-carbonyl)pyridin-4-ylamino)-1,3-dihydrospiro[indene-2,3' pyrrolo[2,3-b]pyridin]-2'(1'H)-one- | 4,5-difluoro-2,3-dihydro-1H-indole hydrochloride 55 mg (0.29 mmol) 30 mg (22% of theory) | ESI-MS: m/z = 510 [M + H]$^+$ R$_t$: 1.17 min (method C) |

| Example Method | Structure | Amine derivative [amount of amine derivative] Yield | Analytical data |
|---|---|---|---|
| Example 31: GWM5 | 5-(2-(3-methylindoline-1-carobnyl)pyridin-4-ylamino)-1,3-dihydrospiro[indene-2,3'-pyrrolo[2,3-b]pyridin]-2'(1'H)-one | 3-methyl-2,3-dihydro-1H-indole 40 mg (0.30 mmol) 55 mg (42% of theory) | ESI-MS: m/z = 488 [M + H]$^+$ R$_t$: 1.15 min (method C) |
| Example 32: GWM5 | 5-(2-(5-hydroxyindoline-1-carobnyl)pyridin-4-ylamino)-1,3-dihydrospiro[indene-2,3'-pyrrolo[2,3-b]pyridin]-2'(1'H)-one | 2,3-dihydro-1H-indol-5-ol 40 mg (0.30 mmol) 65 mg (49% of theory) | ESI-MS: m/z = 490 [M + H]$^+$ R$_t$: 1.08 min (method C) |
| Example 33: GWM5 (method was carried out with 0.17 mmol educt in 1.8 mL DMF) | 1-(4-(2'-oxo-1,1',2',3'-tetrahydro-spiro[indene-2,3'-pyrrolo[2,3-b]-pyridin]-5-ylamino)picolinoyl)-1,2,2a,3-tetrahydropyrrolo[4,3,2-de]quinoline-4(5H)-one | 1,2,2a,5-tetrahydro-3H-pyrrolo[4,3,2-de]quinolin-4-one 30 mg (0.17 mmol) 34 mg (38% of theory) | ESI-MS: m/z = 529 [M + H]$^+$ R$_t$: 2.65 min (method E) |

Example 34

5-(6-(3,3-dimethylpiperidine-1-carbonyl)pyrimidin-4-ylamino)-1,3-dihydrospiro[indene-2,3'-pyrrolo[2,3-b]pyridin]-2'(1'H)-one

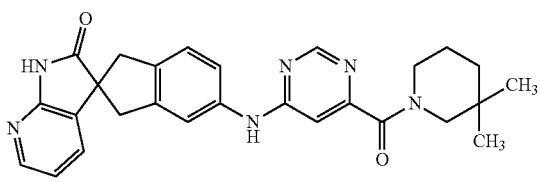

82 mg (0.20 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 32 mg (0.27 mmol) 3,3-dimethyl-piperidine, 80 µL (0.57 mmol) triethylamine and 70 mg (0.22 mmol) TBTU in 0.80 mL DMF were stirred overnight at RT. The purification was carried out by preparative HPLC-MS. The product-containing fractions were combined and lyophilised.

Yield: 21 mg (22% of theory)
ESI-MS: m/z=469 [m+H]$^+$
$R_t$ (HPLC-MS): 1.30 min (method C)

Example 35

N-(dicyclopropylmethyl)-N-methyl-6-(2'-oxo-1,1',2',3-tetrahydrospiro[indene-2,3'-pyrrolo-[2,3-b]pyridin]-5-ylamino)pyrimidine-4-carboxamide

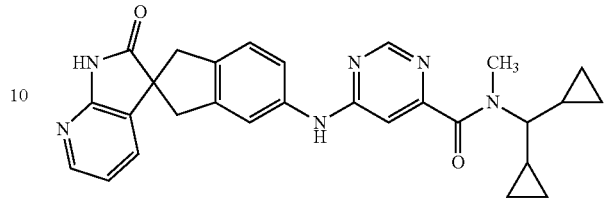

82 mg (0.20 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 35 mg (0.27 mmol) dicyclopropylmethyl-methyl-amine, 80 µL (0.57 mmol) triethylamine and 70 mg (0.22 mmol) TBTU in 0.8 mL DMF were stirred overnight at RT. The purification was carried out by preparative HPLC-MS. The product-containing fractions were combined and lyophilised.

Yield: 25 mg (26% of theory)
ESI-MS: m/z=481 [m+H]$^+$
$R_t$ (HPLC-MS): 1.33 min (method C)

General working method 6 (GWM6) for reacting 6-(2'-oxo-1,1',2',3-tetrahydrospiro[indene-2,3'-pyrrolo[2,3-b]pyridin]-5-ylamino)pyrimidine-4-carboxylic acid hydrochloride with amine derivatives:

1.2 equivalents (12 µmol) of the amine derivative, 3.4 equivalents DIPEA (34 µmol) and 1.20 equivalents (12 µmol) TBTU were added to 4.1 mg (10 µmol) 6-(2'-oxo-1,1',2',3-tetrahydrospiro[indene-2,3'-pyrrolo[2,3-b]pyridin]-5-ylamino)pyrimidine-4-carboxylic acid hydrochloride in 0.32 mL DMF and the mixture was shaken overnight at RT. The reaction mixture was evaporated down at 60° C. in a vacuum centrifuge. The following compounds were able to be synthesised analogously to this working method:

| Example Method | Structure | Amine derivative [amount of amine derivative] | Analytical data |
|---|---|---|---|
| Example 36: GWM6 | 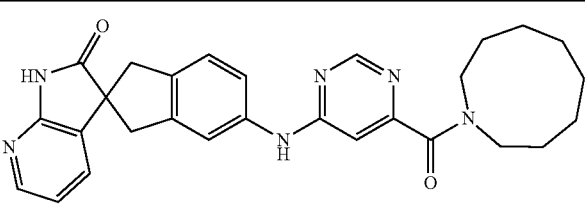<br>5-(6-(azonan-1-carbonyl)pyrimidin-4-ylamino)-1,3-dihydrospiro-[indene-2,3'-pyrrolo[2,3-b]pyridin]-2'(1'H)-one | azacyclonan 1.53 mg (12 µmol) | ESI-MS: m/z = 483 [M + H]$^+$<br>$R_t$: 1.66 min (method Q) |

| Example Method | Structure | Amine derivative [amount of amine derivative] | Analytical data |
|---|---|---|---|
| Example 37: GWM6 | N-cyclopropyl-N-methyl-6-(2'-oxo-1,1',2',3-tetrahydrospiro-[indene-2,3'-pyrrolo[2,3-b]pyriidn]-5-ylamino)pyrimidine-4-carboxamide | N-cyclopropyl-ethylamine 0.85 mg (12 μmol) | ESI-MS: m/z = 427 [M + H]$^+$ R$_t$: 1.42 min (method Q) |
| Example 38: GWM6 | 5-(6-(azepan-1-carbonyl)pyrimi-din-4-ylamino)-1,3-dihydrospiro-[indene-2,3'-pyrrolo[2,3-b]pyridin]-2'(1'H)-one | homopiperidine 1.19 mg (12 μmol) | ESI-MS: m/z = 455 [M + H]$^+$ R$_t$: 1.53 min (method Q) |

Example 39

1-(6-(5-fluoroindoline-1-carbonyl)pyrimidin-4-yl)spiro[piperidine-4,4'-pyrido[2,3-d][1,3]oxazin]-2'(1'H)-one

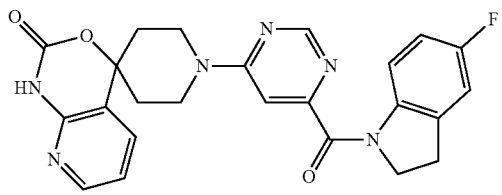

0.10 g (0.36 mmol) (6-chloro-pyrimidin-4-yl)-(5-fluoro-2,3-dihydro-indol-1-yl)-methanone were added to 92 mg (0.36 mmol) spiro[piperidine-4,4'-pyrido[2,3-d][1,3]oxazin]-2'(1'H)-one-hydrochloride and 146 μL (0.84 mmol) DIPEA in 1.8 mL DMF. The reaction mixture was stirred overnight at RT. Then the reaction mixture was purified by preparative HPLC-MS. The product fractions were combined and lyophilised.

Yield: 120 mg (72% of theory)
ESI-MS: m/z=461 (M+H)$^+$
R$_t$ (HPLC-MS): 2.90 min (method E)

Example 40

5-(6-(5-hydroxyindoline-1-carbonyl)pyrimidin-4-ylamino)-1,3-dihydrospiro[indene-2,3'-pyrrolo[2,3-b]pyridin]-2'(1'H)-one

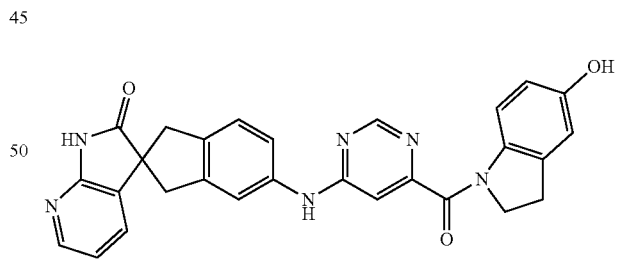

0.15 g (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 mg (0.37 mmol) 2,3-dihydro-1H-indol-5-ol, 150 μL (0.87 mmol) DIPEA and 0.13 g (0.41 mmol) TBTU in 1.8 mL DMF were stirred overnight at RT. The purification was carried out by preparative HPLC-MS. The product-containing fractions were combined and lyophilised.

Yield: 44 mg (23% of theory)
ESI-MS: m/z=491 (M+H)$^+$
R$_t$ (HPLC-MS): 1.33 min (method C)

Example 41

(R)-5-(6-(5-fluoroindoline-1-carbonyl)pyrimidin-4-ylamino)-1,3-dihydrospiro[indene-2,3'-pyrrolo[2,3-b]pyridin]-2'(1'H)-one

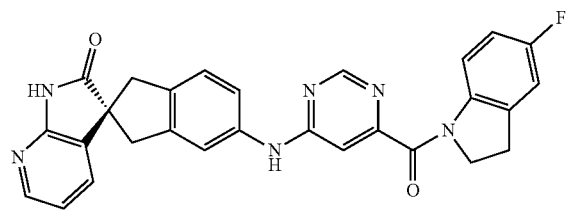

0.10 g (0.40 mmol) (R)-5-amino-1,3-dihydrospiro[indene-2,3'-pyrrolo[2,3-b]pyridin]-2'(1'H)-one, 0.11 g (0.40 mmol) (6-chloro-pyrimidin-4-yl)-(5-fluoro-2,3-dihydro-indol-1-yl)-methanone and 13 µL of a 4 molar aqueous hydrochloric acid solution were added to 2.0 mL 2-propanol and the mixture was refluxed for 4 h. Then the reaction mixture was diluted with diethyl ether, suction filtered and washed with diethyl ether. The precipitate was dissolved in DMF and purified by preparative HPLC-MS. The product-containing fractions were combined and the organic solvent was evaporated down. The residue was made alkaline with a 1N aqueous sodium hydroxide solution, the precipitate formed was suction filtered, washed with water and dried under HV.

Yield: 35 mg (18% of theory)
ESI-MS: m/z=493 (M+H)$^+$
R$_t$ (HPLC-MS): 1.38 min (method C)

Example 42

5-(6-(6-fluoroindoline-1-carbonyl)pyrimidin-4-ylamino)-1,3-dihydrospiro[indene-2,3'-pyrrolo[2,3-b]pyridin]-2'(1'H)-one

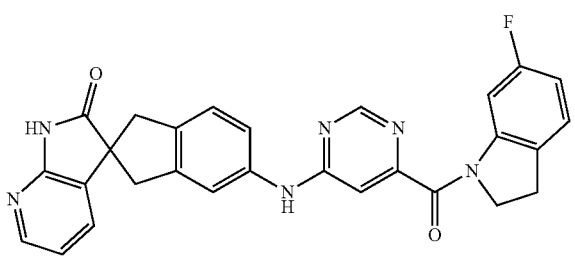

0.10 g (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 35 mg (0.26 mmol) 6-fluoro-2,3-dihydro-1H-indole, 0.10 mL (0.72 mmol) TEA and 90 mg (0.28 mmol) TBTU in 1.8 mL DMF were stirred for 1 h at RT. The purification was carried out by preparative HPLC-MS. The product-containing fractions were combined and lyophilised.

Yield: 55 mg (44% of theory)
ESI-MS: m/z=493 (M+H)$^+$
R$_t$ (HPLC-MS): 1.53 min (method C)

Example 43

5-(6-(2-methylindoline-1-carbonyl)pyrimidin-4-ylamino)-1,3-dihydrospiro[indene-2,3'-pyrrolo[2,3-b]pyridin]-2'(1'H)-ne

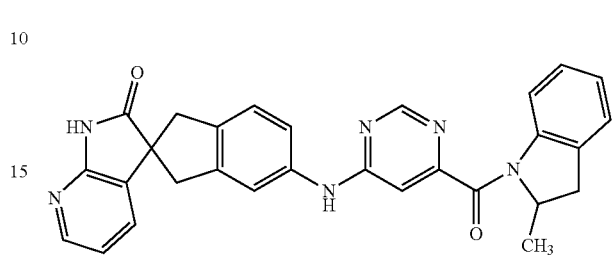

50 mg (0.12 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 16 µL (0.12 mmol) 2-methylindoline, 0.10 mL (0.72 mmol) TEA and 45 mg (0.14 mmol) TBTU in 1.8 mL DMF were stirred overnight at RT. The purification was carried out by preparative HPLC-MS. The product-containing fractions were combined and lyophilised.

Yield: 5.0 mg (8% of theory)
ESI-MS: m/z=489 (M+H)$^+$
R$_t$ (HPLC-MS): 1.59 min (method C)

Example 44

1-(4-(4,5-difluoroindoline-1-carbonyl)pyridin-2-yl)spiro[piperidine-4,4'-pyrido[2,3-d][1,3]-oxazin]-2'(1'H)-one

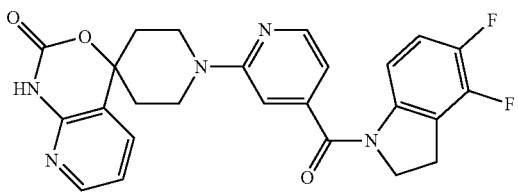

0.23 g (0.78 mmol) (2-chloro-pyridin-4-yl)-(4,5-difluoro-2,3-dihydro-indol-1-yl)-methanone were added to 0.20 g (0.78 mmol) spiro[piperidine-4,4'-pyrido[2,3-d][1,3]oxazin]-2'(1'H)-one-hydrochloride and 0.11 g (0.78 mmol) potassium carbonate in 3.0 mL NMP. The reaction mixture was first of all stirred for 10 h at 130° C., then cooled to RT and then stirred overnight at RT. The crude product was combined with water/acetonitrile and purified by preparative HPLC-MS. The product fractions were combined and evaporated down. The residue was triturated with diisopropylether, suction filtered and dried in the air.

Yield: 50 mg (13% of theory)
ESI-MS: m/z=478 (M+H)$^+$
R$_t$ (HPLC-MS): 3.00 min (method E)

Example 45

(S)-5-(6-(5-fluoroindoline-1-carbonyl)pyrimidin-4-ylamino)-1,3-dihydrospiro[indene-2,3'-pyrrolo[2,3-b]pyridin]-2'(1'H)-one

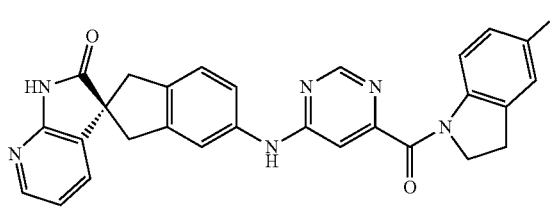

0.10 g (0.40 mmol) (S)-5-amino-1,3-dihydrospiro[indene-2,3'-pyrrolo[2,3-b]pyridin]-2'(1'H)-one, 0.11 g (0.40 mmol) (6-chloro-pyrimidin-4-yl)-(5-fluoro-2,3-dihydro-indol-1-yl)-methanone and 13 µL of a 4 molar aqueous hydrochloric acid solution were added to 2.0 mL of 2-propanol and the mixture was refluxed for 4 h. Then the reaction mixture was dissolved in DMF and purified by preparative HPLC-MS. The product-containing fractions were combined and the organic solvent was evaporated down. The residue was made alkaline with a 1N aqueous sodium hydroxide solution, the precipitate formed was suction filtered, washed with water and dried under HV.

Yield: 45 mg (23% of theory)

ESI-MS: m/z=493 (M+H)$^+$ $R_t$ (HPLC-MS): 1.41 min (method C)

Example 46

5-(6-(5,6-difluoroindoline-1-carbonyl)pyrimidin-4-ylamino)-1,3-dihydrospiro[indene-2,3'-pyrrolo[2,3-b]pyridin]-2'(1'H)-one

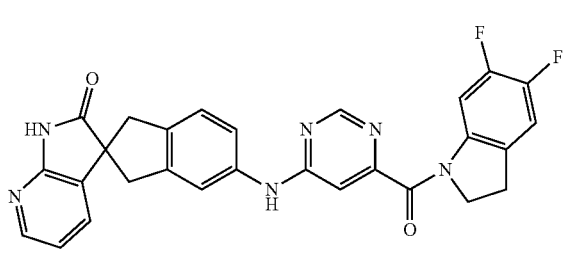

0.10 g (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 mg (0.26 mmol) 5,6-difluoro-2,3-di-hydro-1H-indole, 0.10 mL (0.72 mmol) TEA and 80 mg (0.25 mmol) TBTU in 1.8 mL DMF were stirred overnight at RT. The purification was carried out by preparative HPLC-MS. The product-containing fractions were combined and lyophilised.

Yield: 45 mg (36% of theory)

ESI-MS: m/z=511 (M+H)$^+$ $R_t$ (HPLC-MS): 1.61 min (method C)

Example 47

5-(6-(3-methylindoline-1-carbonyl)pyrimidin-4-ylamino)-1,3-dihydrospiro[indene-2,3'-pyrrolo[2,3-b]pyridin]-2'(1'H)-one

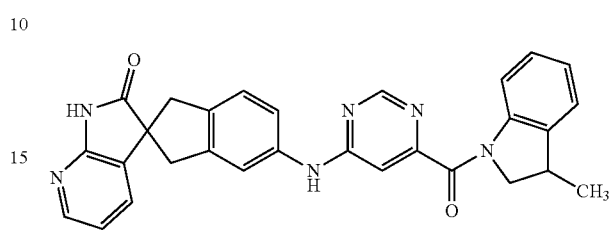

0.15 g (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 61 mg (0.37 mmol) 3-methyl-2,3-di-hydro-1H-indole, 150 µL (0.87 mmol) DIPEA and 0.13 g (0.41 mmol) TBTU in 1.8 mL DMF were stirred for 1 h at RT. The purification was carried out by preparative HPLC-MS. The product-containing fractions were combined and lyophilised.

Yield: 100 mg (56% of theory)

ESI-MS: m/z=489 (M+H)$^+$ $R_t$ (HPLC-MS): 1.58 min (method C)

Example 48

5-(6-(2,3-dihydro-1H-pyrrolo[3,2-c]pyridin-1-carbonyl)pyrimidin-4-ylamino)-1,3-dihydro-spiro[indene-2,3'-pyrrolo[2,3-b]pyridin]-2'(1'H)-one

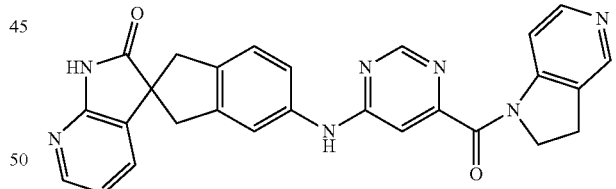

0.15 g (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 45 mg (0.38 mmol) 2,3-dihydro-1H-pyrrolo[3,2-c]pyridine, 0.15 mL (0.87 mmol) DIPEA and 0.13 g (0.41 mmol) TBTU in 1.8 mL DMF were stirred overnight at RT. Then the reaction mixture was mixed with water, the precipitate formed was suction filtered and dissolved in DMF/NMP. The purification was carried out by preparative HPLC-MS. The product-containing fractions were combined and lyophilised. A second purification was carried out by preparative HPLC-MS.

Yield: 9 mg (5% of theory)

ESI-MS: m/z=476 (M+H)$^+$

Example 49

5-(6-(2-ethylindoline-1-carbonyl)pyrimidin-4-ylamino)-1,3-dihydrospiro[indene-2,3'-pyrrolo[2,3-b]pyridin]-2'(1'H)-one

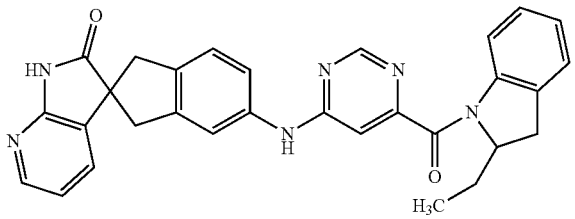

103 mg (0.40 mmol) 5-amino-1,3-dihydrospiro[indene-2,3'-pyrrolo[2,3-b]pyridin]-2'(1'H)-one, 113 mg (0.40 mmol) (6-chloro-pyrimidin-4-yl)-(2-ethyl-2,3-dihydro-indol-1-yl)-methanone and 13 µL of a 4 molar aqueous hydrochloric acid solution were added to 2.0 mL of 2-propanol and the mixture was refluxed for 2 h. Then the reaction mixture was evaporated down and purified by preparative HPLC-MS. The product-containing fractions were combined and the organic solvent was evaporated down. The residue was made alkaline with a 1N aqueous sodium hydroxide solution, the precipitate formed was suction filtered, washed with water and dried under HV.

Yield: 40 mg (20% of theory)
ESI-MS: m/z=503 (M+H)+
$R_t$ (HPLC-MS): 1.56 min (method C)

Example 50

5-(6-(6-Chloroindoline-1-carbonyl)pyrimidin-4-ylamino)-1,3-dihydrospiro[indene-2,3'-pyrrolo[2,3-b]pyridin]-2'(1'H)-one

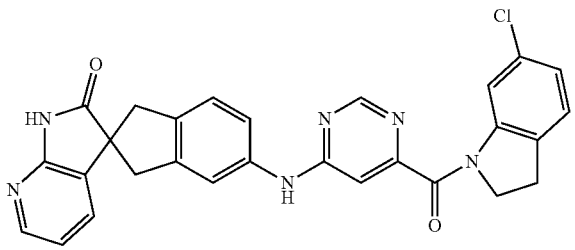

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 63 mg (0.37 mmol) 6-chloro-2,3-dihydro-1H-indole, 0.15 mL (0.87 mmol) DIPEA and 130.00 mg (0.41 mmol) TBTU in 1.8 mL DMF were stirred for 1 h at RT. The reaction mixture was purified by preparative HPLC-MS. The product-containing fractions were combined and suction filtered. The precipitate was dried under HV.

Yield: 70 mg (38% of theory)
ESI-MS: m/z=509 (M+H)+
$R_t$ (HPLC-MS): 1.64 min (method C)

Example 51

N-ethyl-6-(2'-oxo-1,1',2',3-tetrahydrospiro[indene-2,3'-pyrrolo[2,3-b]pyridin]-5-ylamino)-N-phenylpyrimidine-4-carboxamide

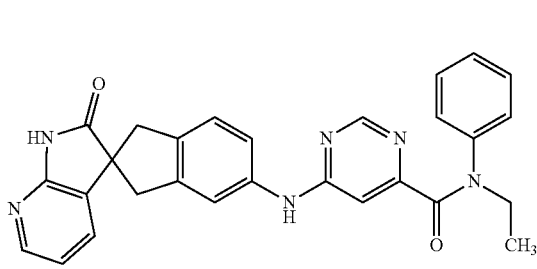

100 mg (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 34 µL (0.24 mmol) N-ethylaniline, 0.10 mL (0.72 mmol) TEA and 85 mg (0.27 mmol) TBTU in 1.8 mL DMF were stirred overnight at RT. The purification was carried out by preparative HPLC-MS. The product-containing fractions were combined and lyophilised.

Yield: 38 mg (33% of theory)
ESI-MS: m/z=477 (M+H)+
$R_t$ (HPLC-MS): 1.43 min (method C)

Example 52

5-(6-(1,2,3,4-tetrahydroquinolin-1-carbonyl)pyrimidin-4-ylamino)-1,3-dihydrospiro[indene-2,3'-pyrrolo[2,3-b]pyridin]-2'(1'H)-one

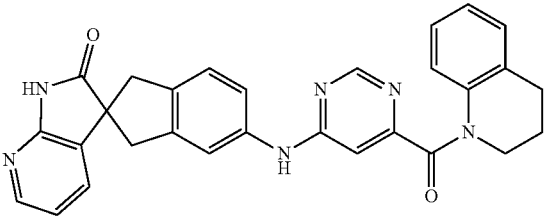

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 µL (0.40 mmol) 1,2,3,4-tetrahydroquinoline, 0.15 mL (0.87 mmol) DIPEA and 130 mg (0.41 mmol) TBTU in 1.8 mL DMF were stirred overnight at RT. The purification was carried out by preparative HPLC-MS. The product-containing fractions were combined and lyophilised.

Yield: 40 mg (20% of theory)
ESI-MS: m/z=489 (M+H)+
$R_t$ (HPLC-MS): 1.43 min (method C)

Example 53

5-(6-(6-hydroxyindoline-1-carbonyl)pyrimidin-4-ylamino)-1,3-dihydrospiro[indene-2,3'-pyrrolo[2,3-b]pyridin]-2'(1'H)-one

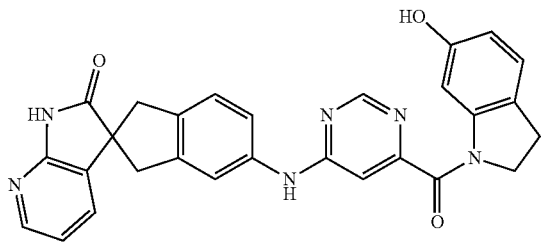

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 mg (0.37 mmol) 2,3-dihydro-1H-indol-6-ol, 0.15 mL (0.87 mmol) DIPEA and 130 mg (0.41 mmol) TBTU in 1.8 mL DMF were stirred overnight at RT. The purification was carried out by preparative HPLC-MS. The product-containing fractions were combined and lyophilised.

Yield: 75 mg (42% of theory)

ESI-MS: m/z=491 (M+H)$^+$

R$_t$ (HPLC-MS): 1.36 min (method C)

Example 54

N-benzyl-N-ethyl-6-(2'-oxo-1,1',2',3-tetrahydrospiro[indene-2,3'-pyrrolo[2,3-b]pyridin]-5-yl-amino)pyrimidine-4-carboxamide

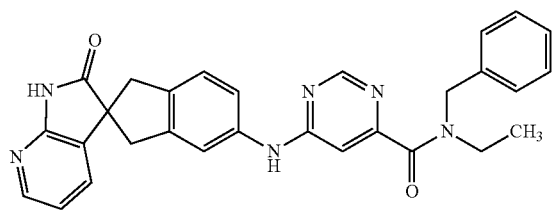

100 mg (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 µL (0.33 mmol) benzylethyl-amine, 0.10 mL (0.72 mmol) TEA and 85 mg (0.27 mmol) TBTU in 1.8 mL DMF were stirred overnight at RT. The purification was carried out by preparative HPLC-MS. The product-containing fractions were combined and lyophilised.

Yield: 40 mg (32% of theory)

ESI-MS: m/z=491 (M+H)$^+$

R$_t$ (HPLC-MS): 1.48 min (method C)

Example 55

5-(4-(2-methylindoline-1-carbonyl)pyridin-2-ylamino)-1,3-dihydrospiro[indene-2,3'-pyrrolo-[2,3-b]pyridin]-2'(1'H)-one

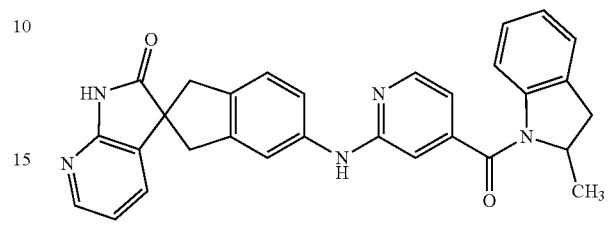

150 mg (0.40 mmol) 2-(2'-oxo-1,1',2',3-tetrahydrospiro[indene-2,3'-pyrrolo[2,3-b]pyridin]-5-ylamino)isonicotinic acid, 55 µL (0.42 mmol) 2-methylindoline, 0.15 mL (0.87 mmol) DIPEA and 130 mg (0.41 mmol) TBTU in 1.8 mL DMF were stirred overnight at RT. The purification was carried out by preparative HPLC-MS. The product-containing fractions were combined and lyophilised.

Yield: 40 mg (20% of theory)

ESI-MS: m/z=488 (M+H)$^+$

R$_t$ (HPLC-MS): 1.52 min (method C)

Example 56

5-(6-((S)-2-(3,5-difluorophenyl)-5,5-dimethylpiperidine-1-carbonyl)pyrimidin-4-ylamino)-1,3-dihydrospiro[indene-2,3'-pyrrolo[2,3-b]pyridin]-2'(1'H)-one

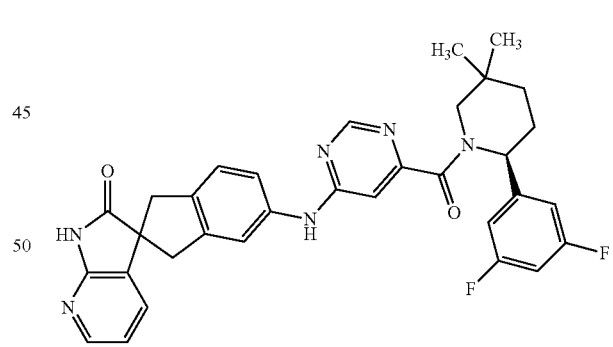

64 mg (0.17 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 70 mg (0.16 mmol) (S)-2-(3,5-difluorophenyl)-5,5-dimethylpiperidine, 40 µL (0.23 mmol) DIPEA and 65 mg (0.17 mmol) HATU in 0.80 mL DMF were stirred overnight at RT. The purification was carried out by preparative HPLC-MS. The product-containing fractions were combined and lyophilised.

Yield: 38 mg (42% of theory)

ESI-MS: m/z=581 (M+H)$^+$

R$_t$ (HPLC-MS): 4.16 min (method E)

Example 57

5-(2-(2-ethyl-6-fluorindoline-1-carbonyl)pyridin-4-ylamino)-1,3-dihydrospiro[indene-2,3'-pyrrolo[2,3-b]pyridin]-2'(1'H)-one

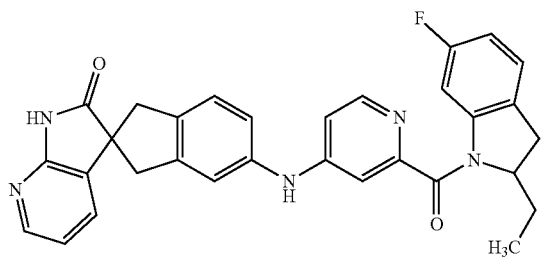

186 mg (0.50 mmol) 4-(2'-oxo-1,1',2',3-tetrahydrospiro[indene-2,3'-pyrrolo[2,3-b]pyridin]-5-ylamino)picolinic acid, 220 mg (0.60 mmol) 2-ethyl-6-fluoro-2,3-dihydro-1H-indole, 0.26 mL (1.5 mmol) DIPEA and 0.18 g (0.55 mmol) TBTU in 5.0 mL DMF were stirred overnight at RT. The purification was carried out by preparative HPLC-MS. The product-containing fractions were combined and the organic solvent was evaporated down. The aqueous residue was made alkaline with 1N aqueous sodium hydroxide solution, the precipitate formed was suction filtered, washed with water and dried under HV.

Yield: 45 mg (17% of theory)
ESI-MS: m/z=520 (M+H)$^+$
R$_t$ (HPLC-MS): 1.39 min (method C)

Example 58

5-(6-(2-(hydroxymethyl)indoline-1-carbonyl)pyrimidin-4-ylamino)-1,3-dihydrospiro[indene-2,3'-pyrrolo[2,3-b]pyridin]-2'(1'H)-one

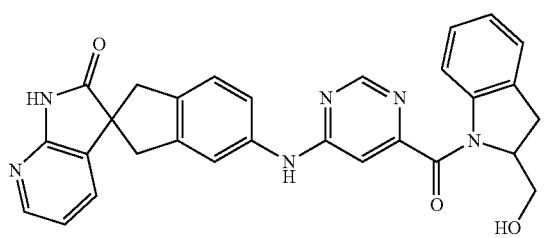

100 mg (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 45 mg (0.30 mmol) (2,3-dihydro-1H-indol-2-yl)-methanol, 0.10 mL (0.71 mmol) TEA and 88 mg (0.27 mmol) TBTU in 1.0 mL DMF were stirred overnight at RT. The purification was carried out by preparative HPLC-MS. The product-containing fractions were combined and the solvent was evaporated down by about half. The precipitate formed was suction filtered and dried.

Yield: 39 mg (32% of theory)
ESI-MS: m/z=505 (M+H)$^+$
R$_t$ (HPLC-MS): 2.90 min (method E)

Example 59

5-(6-(3-(hydroxymethyl)indoline-1-carbonyl)pyrimidin-4-ylamino)-1,3-dihydrospiro[indene-2,3'-pyrrolo[2,3-b]pyridin]-2'(1'H)-one

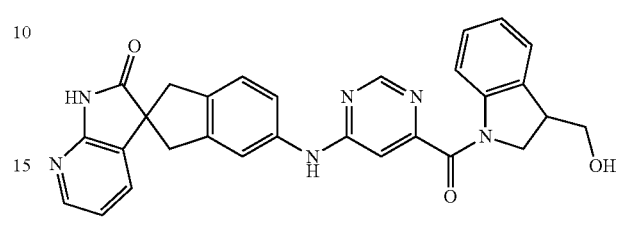

100 mg (0.24 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 45 mg (0.30 mmol) (2,3-dihydro-1H-indol-3-yl)-methanol, 0.10 mL (0.71 mmol) TEA and 88 mg (0.27 mmol) TBTU in 1.0 mL DMF were stirred overnight at RT. The purification was carried out by preparative HPLC-MS. The product-containing fractions were combined and the solvent was evaporated down by about half. The precipitate formed was suction filtered and dried.

Yield: 58 mg (45% of theory)
ESI-MS: m/z=505 (M+H)$^+$

Example 60

5-(6-(2,3-dihydro-1H-pyrrolo[2,3-b]pyridin-1-carbonyl)pyrimidin-4-ylamino)-1,3-dihydro-spiro[indene-2,3'-pyrrolo[2,3-b]pyridin]-2'(1'H)-one

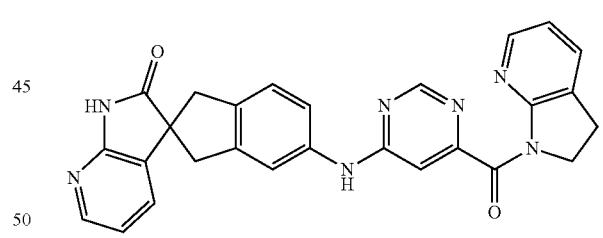

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 50 mg (0.42 mmol) 2,3-dihydro-1H-pyrrolo[2,3-b]pyridine, 0.15 mL (0.87 mmol) DIPEA and 130 mg (0.41 mmol) TBTU in 1.8 mL DMF were stirred overnight at RT. The purification was carried out by preparative HPLC-MS. The product-containing fractions were combined and lyophilised. Then the substance was dissolved in DMF and purified again by preparative HPLC-MS. The product-containing fractions were combined and lyophilised.

Yield: 12 mg (6% of theory)
ESI-MS: m/z=476 (M+H)$^+$
R$_t$ (HPLC-MS): 1.28 min (method C)

Example 61

5-(6-(6-nitroindoline-1-carbonyl)pyrimidin-4-ylamino)-1,3-dihydrospiro[indene-2,3'-pyrrolo-[2,3-b]pyridin]-2'(1'H)-one

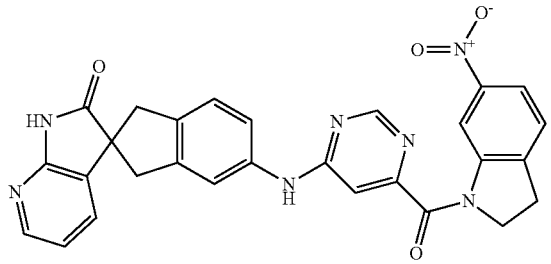

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid-hydrochloride, 60 mg (0.37 mmol) 4-nitroindole, 0.15 mL (0.87 mmol) DIPEA and 130 mg (0.41 mmol) TBTU in 1.8 mL DMF were stirred overnight at RT. Then the reaction mixture was diluted with water/MeOH, the precipitate formed was suction filtered and washed with plenty of water. The precipitate was dried.

Yield: 165 mg (74% of theory)
ESI-MS: m/z=520 (M+H)$^+$
R$_t$ (HPLC-MS): 1.56 min (method C)

Example 62

5-(6-(6-methylindoline-1-carbonyl)pyrimidin-4-ylamino)-1,3-dihydrospiro[indene-2,3'-pyrrolo[2,3-b]pyridin]-2'(1'H)-one

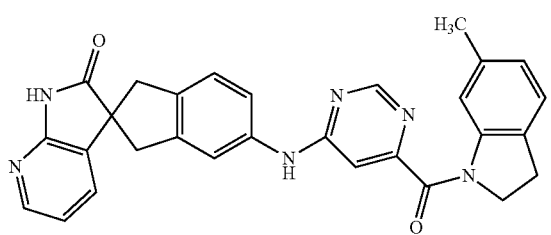

150 mg (0.37 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 62 mg (0.4 mmol) 6-methyl-2,3-dihydro-1H-indole-hydrochloride, 0.15 mL (0.87 mmol) DIPEA and 130 mg (0.41 mmol) TBTU in 1.8 mL DMF were stirred overnight at RT. The purification was carried out by preparative HPLC-MS. The product-containing fractions were combined and the organic solvent was evaporated down. The precipitate formed was suction filtered and dried under HV.

Yield: 45 mg (25% of theory)
ESI-MS: m/z=489 (M+H)$^+$
R$_t$ (HPLC-MS): 1.57 min (method C)

Example 63

5-(6-(6-methoxyindoline-1-carbonyl)pyrimidin-4-ylamino)-1,3-dihydrospiro[indene-2,3'-pyrrolo[2,3-b]pyridin]-2'(1'H)-one

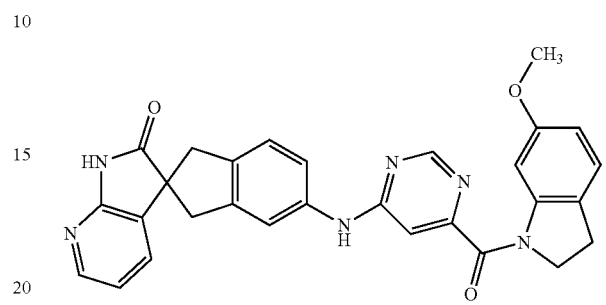

83 mg (0.20 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 30 mg (0.20 mmol) 6-methoxy-2,3-dihydro-1-H-indole, 51 µL (0.36 mmol) TEA and 70 mg (0.22 mmol) TBTU in 1.5 mL DMF were stirred for 1 h at RT. The purification was carried out by preparative HPLC-MS. The product-containing fractions were combined and lyophilised.

Yield: 53 mg (52% of theory)
ESI-MS: m/z=505 (M+H)$^+$
R$_t$ (HPLC-MS): 1.52 min (method C)

Example 64

5-(6-(5,6,7,8-tetrahydro-4H-thiazolo[5,4-d]azepine-6-carbonyl)pyrimidin-4-ylamino)-1,3-di-hydrospiro[indene-2,3'-pyrrolo[2,3-b]pyridin]-2'(1'H)-one

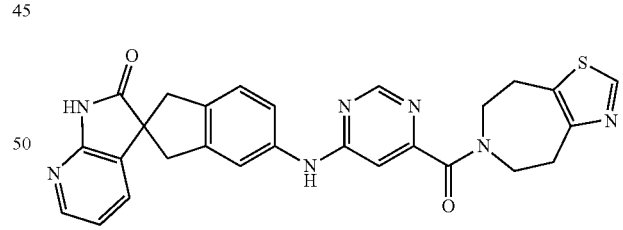

86 mg (0.21 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 37 mg (0.24 mmol) 5,6,7,8-tetrahydro-4H-thiazolo[4,5-d]azepine, 0.13 mL (0.72 mmol) DIPEA and 77 mg (0.24 mmol) TBTU in 1.0 mL DMF were stirred overnight at RT. The purification was carried out by preparative HPLC-MS. The product-containing fractions were combined and lyophilised.

Yield: 16 mg (15% of theory)
ESI-MS: m/z=510 (M+H)$^+$
R$_t$ (HPLC-MS): 1.25 min (method C)

Example 65

5-(6-(1,4,5,6,7,8-hexahydroimidazo[4,5-d]azepine-6-carbonyl)pyrimidin-4-ylamino)-1,3-di-hydrospiro[indene-2,3'-pyrrolo[2,3-b]pyridin]-2'(1'H)-one

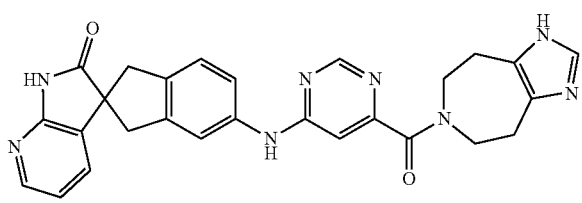

86 mg (0.21 mmol) 6-(2'-oxo-1,1',2',3-tetrahydrospiro[indene-2,3'-pyrrolo[2,3-b]pyridin]-5-ylamino)pyrimidine-4-carboxylic acid hydrochloride, 33 mg (0.24 mmol) 1,4,5,6,7,8-hexahydroimidazo[4,5-d]azepine, 0.13 mL (0.72 mmol) DIPEA and 77 mg (0.24 mmol) TBTU in 1.0 mL DMF were stirred overnight at RT. The purification was carried out by preparative HPLC-MS. The product-containing fractions were combined and lyophilised. Then the substance was purified again by preparative HPLC-MS.

Yield: 21 mg (19% of theory)
ESI-MS: m/z=493 (M+H)$^+$
$R_t$ (HPLC-MS): 1.08 min (method C)

General working method 7 (GWM7) for reacting 6-(2'-oxo-1,1',2',3-tetrahydrospiro[indene-2,3'-pyrrolo[2,3-b]pyridin]-5-ylamino)pyrimidine-4-carboxylic acid hydrochloride with amine derivatives:

1.2 equivalents (12 μmol) of the amine derivative, 3.4 equivalents DIPEA (34 μmol) and 1.2 equivalents (12 μmol) HATU were added to 4.10 mg (10 μmol) 6-(2'-oxo-1,1',2',3-tetrahydrospiro[indene-2,3'-pyrrolo[2,3-b]pyridin]-5-ylamino)pyrimidine-4-carboxylic acid hydrochloride in 0.32 mL DMF and the mixture was shaken overnight at 80° C. The reaction mixture was evaporated down in the vacuum centrifuge at 60° C. The following compounds were able to be synthesised analogously to this working method:

| Example Method | Structure | Amine derivative [amount of amine derivative] | Analytical data |
|---|---|---|---|
| Example 66: GWM7 | 5-(6-(2,5-dihydro-1H-pyrrol-1-carbonyl)pyrimidin-4-ylamino)-1,3-dihydrospiro[indene-2,3'-pyrrolo[2,3-b]pyridin]-2'(1'H)-one | 2,5-dihydropyrrole 0.83 mg (12 μmol) | ESI-MS: m/z = 425 [M + H]$^+$ $R_t$: 1.45 min (method Q) |
| Example 67: GWM7 | N-(but-3-ynyl)-N-methyl-6-(2'-oxo-1,1',2',3-tetrahydrospiro-[indene-2,3'-pyrrolo[2,3-b]pyridin]-5-ylamino)pyrimidine-4-carboxamide | but-3-ynyl-methyl-amine 1.00 mg (12 μmol) | ESI-MS: m/z = 439 [M + H]$^+$ $R_t$: 1.46 min (method Q) |

-continued

| Example Method | Structure | Amine derivative [amount of amine derivative] | Analytical data |
|---|---|---|---|
| Example 68: GWM7 | 5-(6-(decahydroquinoline-1-carbonyl)pyrimidin-4-ylamino)-1,3-dihydrospiro[indene-2,3′-pyrrolo[2,3-b]pyridin]-2′(1′H)-one | decahydroquinoline 1.67 mg (12 µmol) | ESI-MS: m/z = 495 [M + H]⁺ R$_t$: 1.68 min (method Q) |
| Example 69: GWM7 | 5-(6-(2-methylpiperidine-1-carbonyl)pyrimidin-4-ylamino)-1,3-dihydrospiro[indene-2,3′-pyrrolo[2,3-b]pyridin]-2′(1′H)-one | 2-methylpiperidine 1.19 mg (12 µmol) | ESI-MS: m/z = 455 [M + H]⁺ R$_t$: 1.53 min (method Q) |
| Example 70: GWM7 | 5-(6-(piperidine-1-carbonyl)pyrimidin-4-ylamino)-1,3-dihydrospiro[indene-2,3′-pyrrolo[2,3-b]pyridin]-2′(1′H)-one | piperidine 1.02 mg (12 µmol) | ESI-MS: m/z = 441 [M + H]⁺ R$_t$: 1.47 min (method Q) |
| Example 71: GWM7 | 5-(6-pyrrolidin-1-carbonyl)pyrimidin-4-ylamino)-1,3-dihydrospiro[indene-2,3′-pyrrool[2,3-b]pyridin]-2′(1′H)-one | pyrrolidine 0.85 mg (12 µmol) | ESI-MS: m/z = 427 [M + H]⁺ R$_t$: 1.42 min (method Q) |

| Example Method | Structure | Amine derivative [amount of amine derivative] | Analytical data |
|---|---|---|---|
| Example 72: GWM7 | N-methyl-6-(2'-oxo-1,1',2',3-tetrahydrospiro[indene-2,3'-pyrrolo[2,3-b]pyridin]-5-ylamino)-N-phenylpyrimidine-4-carboxamide | N-methylaniline 1.29 mg (12 μmol) | ESI-MS: m/z = 232 [M + 2H]$^{++}$ R$_t$: 1.53 min (method Q) |
| Example 73: GWM7 | 5-(6-(3-oxo-1,4-diazepan-1-carbonyl)pyrimidin-4-ylamino)-1,3-dihydrospiro[indene-2,3'-pyrrolo[2,3-b]pyridin]-2'(1'H)-one | 5-homopiperazinone 1.37 mg (12 μmol) | ESI-MS: m/z = 470 [M + H]$^+$ R$_t$: 1.33 min (method Q) |
| Example 74: GWM7 | 5-(6-(decahydroisoquinoline-2-carbonyl)pyrimidin-4-ylamino)-1,3-dihydrospiro[indene-2,3'-pyrrolo[2,3-b]pyridin]-2'(1'H)-one | decahydro-isoquinoline 1.67 mg (12 μmol) | ESI-MS: m/z = 248 [M + 2H]$^{++}$ R$_t$: 1.72 min (method Q) |

The following Examples describe the preparation of pharmaceutical formulations that contain as active substance any desired compound of general formula I:

Example I

Capsules for Powder Inhalation Containing 1 mg of Active Ingredient

Composition:
1 Capsule for Powder Inhalation Contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:
1 Puff Contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:

The active ingredient and benzalkonium chloride are dissolved in water and transferred into Respimat® cartridges.

Example III

Inhalable Solution for Nebulisers Containing 1 mg of Active Ingredient

Composition:
1 Vial Contains:

| | |
|---|---|
| active ingredient | 0.1 g |
| sodium chloride | 0.18 g |
| benzalkonium chloride | 0.002 g |
| purified water ad | 20.0 ml |

Method of Preparation:

The active ingredient, sodium chloride and benzalkonium chloride are dissolved in water.

Example IV

Propellant Gas-Operated Metered Dose Aerosol Containing 1 mg of Active Ingredient Composition:
1 Puff Contains:

| | |
|---|---|
| active ingredient | 1.0 mg |
| lecithin | 0.1% |
| propellant gas ad | 50.0 µl |

Method of Preparation:

The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:

The active ingredient and the excipients are dissolved in water and transferred into a suitable container.

Example VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:

Glycofurol and glucose are dissolved in water for injections (Wfl); human serum albumin is added; active ingredient is dissolved with heating; made up to specified volume with Wfl; transferred into ampoules under nitrogen gas.

Example VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 10 ml |

Preparation:

Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

Example IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| | |
|---|---|
| active substance | 50 mg |
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance Per 1 ml

Composition:

| | |
|---|---|
| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

The invention claimed is:

1. A compound of the formula I

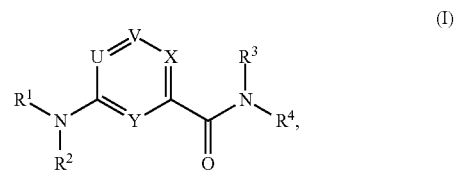

wherein $R^1$ denotes a group of the formula IIa or IIb

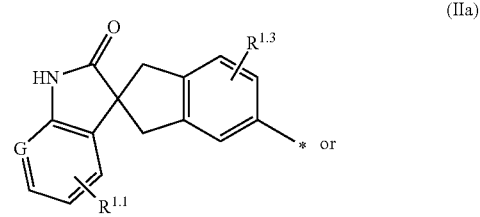

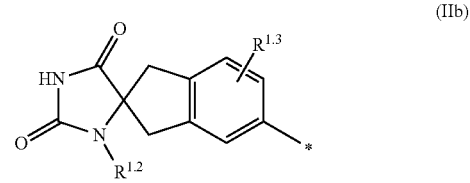

and $R^2$ denotes H or $C_{1-3}$-alkyl, or $R^1$ and $R^2$ together with the nitrogen atom to which they are bound denote a group of the formula IIIa or IIIb

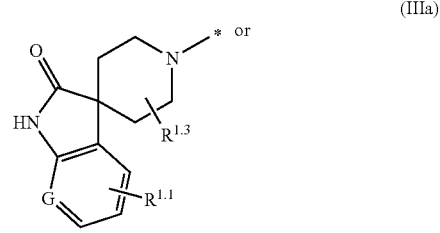

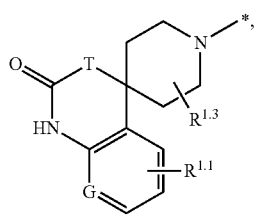

(IIIb)

G denotes C-$R^{1.1}$ or N,
T denotes N-$R^{1.2}$ or O,
$R^{1.1}$ independently of one another denote
  (a) H,
  (b) halogen, $C_{1-3}$-alkyl, —OH, —CN, $C_{1-3}$-alkyl-O—, —C(O)—O—$C_{1-3}$-alkyl, $C_{2-4}$-alkenyl, —$C_{2-4}$-alkynyl, $C_{1-3}$-alkyl-S—, cyclopropyl, —NH$_2$, —COOH, —NH—C(O)—O—$C_{1-3}$-alkyl, —NH—C(O)—$C_{1-3}$-alkyl,
  (c) a $C_{1-3}$-alkyl group or $C_{1-3}$-alkyl-O— group, wherein each methylene group is substituted by up to two fluorine atoms and each methyl group is substituted by up to three fluorine atoms,
$R^{1.2}$ independently of one another denote
  (a) H or
  (b) $C_{1-3}$-alkyl,
$R^{1.3}$ denotes
  (a) H,
  (b) F, —CN, $C_{1-3}$-alkyl, —CO$_2$—$R^{1.3.1}$ or
  (c) a $C_{1-3}$-alkyl group, wherein each methylene group may be substituted by up to two fluorine atoms and each methyl group may be substituted by up to three fluorine atoms,
$R^{1.3.1}$ denotes
  (a) H, or
  (b) $C_{1-6}$-alkyl,
$R^3$ denotes
  (a) H,
  (b) $C_{1-6}$-alkylene-$R^{3.1}$,
  (c) a $C_{3-6}$-cycloalkyl group substituted by one or two groups $R^{3.2}$,
  (d) a $C_{5-7}$-cycloalkenyl group substituted by one or two groups $R^{3.2}$,
  (e) an aryl group substituted by one or two groups $R^{3.2}$,
  (f) a heterocyclyl group substituted by one or two groups $R^{3.2}$,
  (g) a $C_{5-7}$-cycloalkyl group, which may be fused to an aryl or heteroaryl group and is additionally substituted by one or two groups $R^{3.2}$,
  (h) a heteroaryl group substituted by one or two groups $R^{3.2}$,
  (i) a $C_{1-3}$-alkyl group, wherein each methylene group is substituted by up to two fluorine atoms and each methyl group is substituted by up to three fluorine atoms, or
  (j) a dicyclopropylmethyl group,
$R^{3.1}$ denotes
  (a) H,
  (b) an aryl group substituted by the groups $R^{3.1.1}$ and $R^{3.1.2}$,
  (c) a heteroaryl group substituted by the groups $R^{3.1.1}$ and $R^{3.1.2}$, or
  (d) a $C_{2-4}$-alkynyl group,
$R^{3.1.1}$ denotes
  (a) H,
  (b) halogen, $C_{1-3}$-alkyl, —OH, —CN, —O—$C_{1-3}$-alkyl, —O—C(O)—$C_{1-3}$-alkyl, —NR$^{3.1.1.1}$R$^{3.1.1.2}$, —S(O)$_m$—$C_{1-3}$-alkyl, —NR$^{3.1.1.1}$—C(O)—$C_{1-3}$-alkyl, —C(O)—NR$^{3.1.1.1}$R$^{3.1.1.2}$, —C(O)—O—R$^{3.1.1.3}$, —NR$^{3.1.1.1}$—C(O)—O—$C_{1-3}$-alkyl, —O—C(O)—NR$^{3.1.1.1}$R$^{3.1.1.2}$, or
  (c) a $C_{1-3}$-alkyl or —O—$C_{1-3}$-alkyl group, wherein each methylene group is substituted by up to two fluorine atoms and each methyl group is substituted by up to three fluorine atoms,
$R^{3.1.1.1}$ denotes H, or $C_{1-3}$-alkyl and
$R^{3.1.1.2}$ denotes H, or $C_{1-3}$-alkyl, or
$R^{3.1.1.1}$ and $R^{3.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —OCF$_3$, $C_{1-3}$-alkyl and CF$_3$,
$R^{3.1.1.3}$ denotes H, or $C_{1-3}$-alkyl,
$R^{3.1.2}$ denotes
  (a) H,
  (b) halogen, $C_{1-3}$-alkyl, —OH, —CN, —O—$C_{1-3}$-alkyl, or
  (c) a $C_{1-3}$-alkyl- or —O—$C_{1-3}$-alkyl group, wherein each methylene group is substituted by up to two fluorine atoms and each methyl group is substituted by up to three fluorine atoms, or
$R^{3.2}$ independently of one another denote
  (a) H,
  (b) halogen, $C_{1-3}$-alkyl, —OH, —CN, —O—$C_{1-3}$-alkyl, —O—C(O)—$C_{1-3}$-alkyl, —NR$^{3.2.1}$R$^{3.2.2}$, —S(O)$_m$—$C_{1-3}$-alkyl, —NR$^{3.2.1}$—C(O)—$C_{1-3}$-alkyl, —C(O)—NR$^{3.2.1}$R$^{3.2.2}$, —C(O)—O—R$^{3.2.3}$, —NR$^{3.2.1}$—C(O)—O—$C_{1-3}$-alkyl, —O—C(O)—NR$^{3.2.1}$R$^{3.2.2}$, or
  (c) a $C_{1-3}$-alkyl- or —O—$C_{1-3}$-alkyl group, wherein each methylene group is substituted by up to two fluorine atoms and each methyl group is substituted by up to three fluorine atoms,
$R^{3.2.1}$ denotes H, or $C_{1-3}$-alkyl and
$R^{3.2.2}$ denotes H, or $C_{1-3}$-alkyl, or
$R^{3.2.1}$ and $R^{3.2.2}$ together with the nitrogen atom to which they are bound, also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —OCF$_3$, $C_{1-3}$-alkyl and CF$_3$,
$R^{3.2.3}$ denotes H, or $C_{1-3}$-alkyl,
$R^4$ denotes
  (a) H,
  (b) $C_{1-6}$-alkylene—$R^{4.1}$,
  (c) a $C_{3-6}$-cycloalkyl group substituted by one or two groups $R^{4.2}$,
  (d) a $C_{5-7}$-cycloalkenyl group substituted by one or two groups $R^{4.2}$,
  (e) an aryl group substituted by one or two groups $R^{4.2}$,
  (f) a heterocyclyl group substituted by one or two groups $R^{4.2}$,
  (g) a $C_{5-7}$-cycloalkyl group, which may be fused to an aryl or heteroaryl group and is additionally substituted by one or two groups $R^{4.2}$,
  (h) a heteroaryl group substituted by one or two groups $R^{4.2}$, (i) a $C_{1-3}$-alkyl group, wherein each methylene group is substituted by up to two fluorine atoms and each methyl group is substituted by up to three fluorine atoms, or (j) a dicyclopropylmethyl group, $R^{4.1}$ denotes (a) H, (b) an aryl group substituted by the groups $R^{4.1.1}$ and $R^{4.1.2}$, (c) a heteroaryl group substituted by the groups $R^{4.1.1}$ and $R^{4.1.2}$, or (d) a $C_{2-4}$-alkynyl group, $R^{4.1.1}$ denotes (a) H, (b) halogen, $C_{1-3}$-alkyl, —OH, —CN, —O—$C_{1-3}$-alkyl, —O—C(O)—$C_{1-3}$-alkyl, —$NR^{4.1.1.1}R^{4.1.1.2}$, —$S(O)_m$—$C_{1-3}$-alkyl, —$NR^{4.1.1.1}$—C(O)—$C_{1-3}$-alkyl, —C(O)—$NR^{4.1.1.1}R^{4.1.1.2}$, —C(O)—O—$R^{4.1.1.3}$, —$NR^{4.1.1.1}$—C(O)—O—$C_{1-3}$-alkyl, —O—C(O)—$NR^{4.1.1.1}R^{4.1.1.2}$, or (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.1}$ denotes H, or $C_{1-3}$-alkyl and $R^{4.1.1.2}$ denotes H, or $C_{1-3}$-alkyl, or $R^{4.1.1.1}$ and $R^{4.1.1.2}$ together with the nitrogen atom to which they are bound also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —OCF$_3$, $C_{1-3}$-alkyl and CF$_3$, $R^{4.1.1.3}$ denotes H, or $C_{1-3}$-alkyl, $R^{4.1.2}$ denotes (a) H, (b) halogen, $C_{1-3}$-alkyl, —OH, —CN, —O—$C_{1-3}$-alkyl, or (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ independently of one another denote (a) H, (b) halogen, $C_{1-3}$-alkyl, —OH, —CN, —O—$C_{1-3}$-alkyl, —O—C(O)—$C_{1-3}$-alkyl, —$NR^{4.2.1}R^{4.2.2}$, —$S(O)_m$—$C_{1-3}$-alkyl, —$NR^{4.2.1}$—C(O)—$C_{1-3}$-alkyl, —C(O)—$NR^{4.2.1}R^{4.2.2}$, —C(O)—O—$R^{4.2.3}$, —$NR^{4.2.1}$—C(O)—O—$C_{1-3}$-alkyl, —O—C(O)—$NR^{4.2.1}R^{4.2.2}$, or (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.2.1}$ denotes H, or $C_{1-3}$-alkyl and $R^{4.2.2}$ denotes H, or $C_{1-3}$-alkyl, or $R^{4.2.1}$ and $R^{4.2.2}$ together with the nitrogen atom to which they are bound, also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —OCF$_3$, $C_{1-3}$-alkyl and CF$_3$, $R^{4.2.3}$ denotes H, or $C_{1-3}$-alkyl, or $R^3$ and $R^4$ together with the nitrogen atom to which they are bound denote:

(a) a saturated 5-, 6-, 7- or 9-membered heterocyclic group, which is substituted at a carbon atom by a group $R^{4.3}$ or by two groups $R^{4.3}$ and $R^{4.4}$, (b) a saturated 5-, 6- or 7-membered heterocyclic group, which is substituted at two adjacent carbon atoms by in each case a group $R^{4.3}$ and $R^{4.4}$, (c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, wherein the fused-on cycloalkyl or heterocyclyl group is substituted by 1, 2 or 3 groups $R^{4.5}$, (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$, (e) a monounsaturated 5-, 6- or 7-membered heterocyclic group, which is substituted at a carbon atom by a group $R^{4.3}$ or by two groups $R^{4.3}$ and $R^{4.4}$ and additionally is fused to a 5- or 6-membered heteroaryl group, wherein the fused-on heteroaryl group is substituted by 1, 2 or 3 groups $R^{4.5}$, or (f) a heteroaryl group, which is substituted at 1, 2 or 3 carbon atoms by in each case a group $R^{4.5}$, $R^{4.3}$ independently of one another denote (a) H, $C_{1-3}$-alkyl, HO—$C_{1-3}$-alkylene-, $C_{2-6}$-alkynyl, aryl, —$C_{1-3}$-alkylene-$R^{4.3.1}$, $C_{1-3}$-alkyl-O—C(O)—, HO—C(O)—, F, —O—$C_{1-3}$-alkyl, —OH, —CN, or (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3.1}$ denotes H, $C_{1-3}$-alkyl-O—C(O)—, —NH$_2$, ($C_{1-4}$-alkyl)—NH—, ($C_{1-4}$-alkyl)$_2$N—, $C_{3-6}$-cycloalkyl-, heterocyclyl, heteroaryl, or aryl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound, also denote a $C_{3-6}$-cycloalkyl, $C_{5-6}$-cycloalkenyl or heterocyclyl group, $R^{4.5}$ independently of one another denote (a) H, (b) halogen, $C_{1-3}$-alkyl, —OH, —O—$C_{1-3}$-alkyl, —$S(O)_m$—$C_{1-3}$-alkyl, —$NR^{4.5.2}R^{4.5.3}$, —CN, —NO$_2$, —C(O)—O—$R^{4.5.1}$, —C(O)—$NR^{4.5.2}R^{4.5.3}$, (c) a $C_{1-3}$-alkyl or —O—$C_{1-3}$-alkyl group, wherein each methylene group is substituted by up to two fluorine atoms and each methyl group is substituted by up to three fluorine atoms, or (d) aryl, heteroaryl, $R^{4.5.1}$ denotes H, or $C_{1-3}$-alkyl, $R^{4.5.2}$ denotes H, or $C_{1-3}$-alkyl, $R^{4.5.3}$ denotes H, or $C_{1-3}$-alkyl, or $R^{4.5.2}$ and $R^{4.5.3}$ together with the nitrogen atom to which they are bound also denote a group which is selected from morpholinyl, thiomorpholinyl, piperidinyl, piperidonyl, piperazinyl, pyrrolidinyl and azetidinyl, wherein the group may additionally be substituted by one or two substituents selected from F, —OH, —O—$C_{1-3}$-alkyl, —OCF$_3$, $C_{1-3}$-alkyl and CF$_3$, and,
the ring

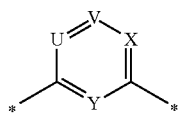

denotes a group of the formula

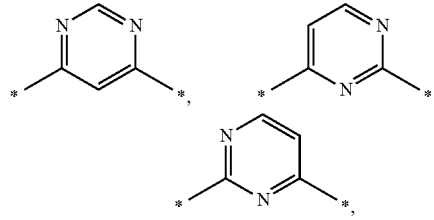

or a tautomer or salt thereof.

2. A compound of the formula I according to claim 1, wherein $R^1$ denotes

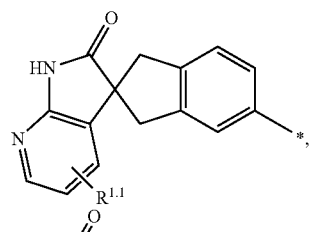

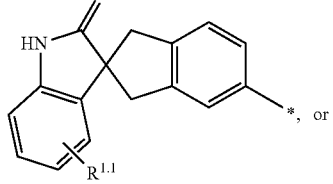

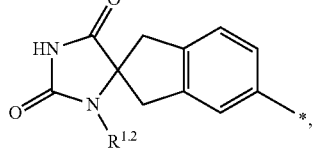

$R^{1.1}$ denotes
  (a) H,
  (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S—, —NH$_2$, or
  (c) a $C_{1-3}$-alkyl group or $C_{1-3}$-alkyl-O— group, wherein each methylene group is substituted by up to two fluorine atoms and each methyl group is substituted by up to three fluorine atoms, and $R^{1.2}$ denotes H or CH$_3$ and $R^2$ denotes H or $C_{1-3}$-alkyl, or a tautomer or salt thereof.

3. A compound of the formula I according to claim 1, wherein $R^1$ and $R^2$ together with the nitrogen atom to which they are attached denote

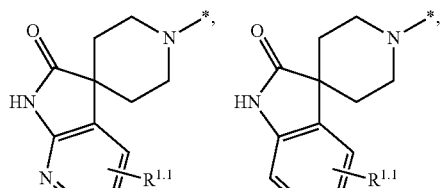

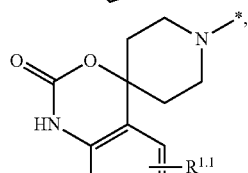

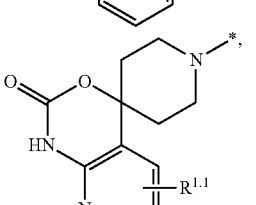

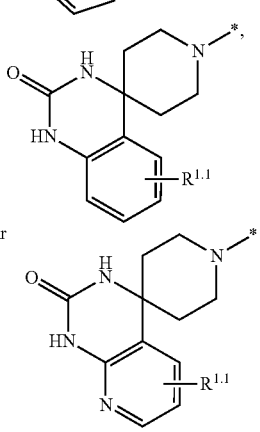

and $R^{1.1}$ denotes
  (a) H,
  (b) halogen, $C_{1-3}$-alkyl, —OH, —CN, —O—$C_{1-3}$-alkyl, —C(O)—O—$C_{1-3}$-alkyl, $C_{2-4}$-alkenyl, $C_{2-4}$-alkynyl, $C_{1-3}$-alkyl-S—, —NH$_2$, or
  (c) a $C_{1-3}$-alkyl group or $C_{1-3}$-alkyl-O— group wherein each methylene group is substituted by up to two fluorine atoms and each methyl group is substituted by up to three fluorine atoms, or a tautomer or salt thereof.

4. A compound of the formula I according to claim 1, wherein $R^1$ denotes

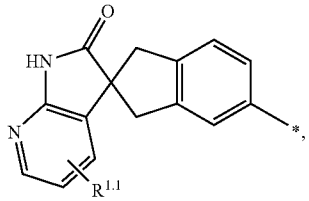

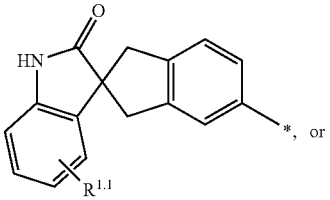

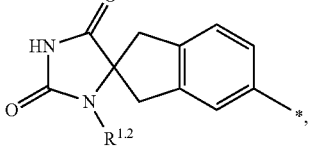

$R^{1.1}$ denotes
 (a) F, CH$_3$, —OH, —O—CH$_3$ or
 (b) CF$_3$ and
$R^2$ denotes H or C$_{1-3}$-alkyl,
or a tautomer or salt thereof.

5. A compound of the formula I according to claim 1, wherein
$R^1$ and $R^2$ together with the nitrogen atom to which they are attached denote

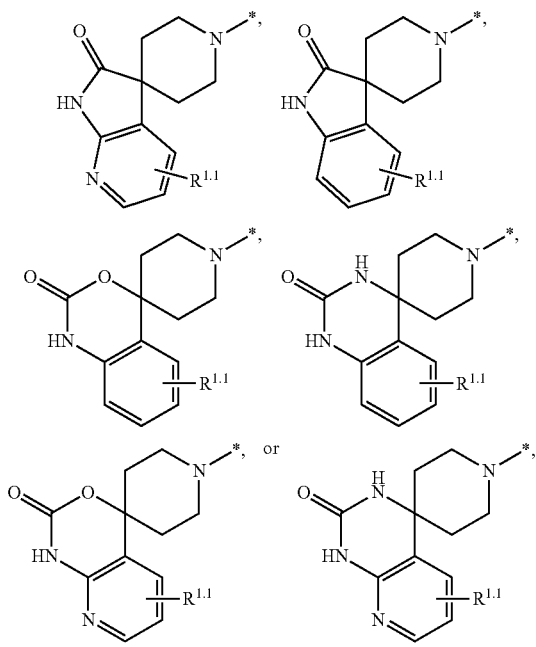

and
$R^{1.1}$ denotes
 (a) F, CH$_3$, —OH, —O—CH$_3$ or
 (b) CF$_3$,
or a tautomer or salt thereof.

6. A compound of the formula I according to claim 1, wherein
$R^1$ denotes

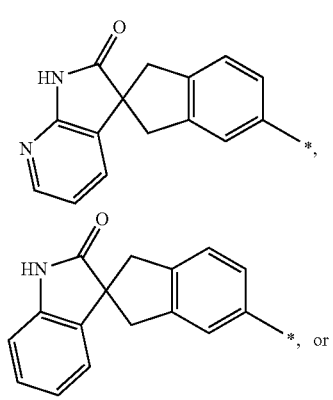

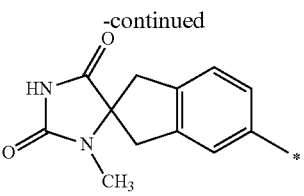

and
$R^2$ denotes H,
or a tautomer or salt thereof.

7. A compound of the formula I according to claim 1, wherein
$R^1$ and $R^2$ together with the nitrogen atom to which they are attached denote

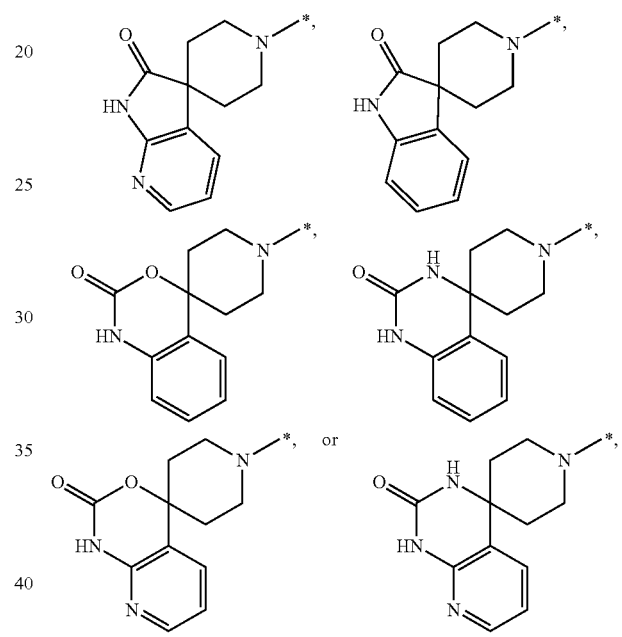

or a tautomer or salt thereof.

8. A compound of the formula I according to claim 1, wherein
$R^3$ denotes
 (a) H,
 (b) C$_{1-6}$-alkyl,
 (c) a C$_{3-6}$-cycloalkyl group substituted by one or two groups $R^{3.2}$, or
 (d) a C$_{1-3}$-alkyl group, wherein each methylene group is substituted by up to two fluorine atoms and each methyl group is substituted by up to three fluorine atoms,
$R^{3.2}$ independently of one another denote
 (a) H,
 (b) halogen, C$_{1-3}$-alkyl, —OH, —O—C$_{1-3}$-alkyl, or
 (c) a C$_{1-3}$-alkyl- or —O—C$_{1-3}$-alkyl group, wherein each methylene group is substituted by up to two fluorine atoms and each methyl group is substituted by up to three fluorine atoms,
$R^4$ denotes
 (a) H,
 (b) C$_{1-6}$-alkylene-$R^{4.1}$,
 (c) a C$_{3-6}$-cycloalkyl group substituted by one or two groups $R^{4.2}$, (d) a $C_{5-7}$-cycloalkenyl group substituted by one or two groups $R^{4.2}$, (e) an aryl group substituted by one or two groups $R^{4.2}$, (f) a $C_{5-7}$-cycloalkyl group which may be fused to an aryl group and is additionally substituted by one or two groups $R^{4.2}$, or (g) a heteroaryl group substituted by one or two groups $R^{4.2}$, $R^{4.1}$ denotes (a) H, (b) a phenyl group substituted by the groups $R^{4.1.1}$ and $R^{4.1.2}$, (c) a heteroaryl group substituted by the groups $R^{4.1.1}$ and $R^{4.1.2}$, or (d) a $C_{2-3}$-alkynyl group, $R^{4.1.1}$ denotes (a) H, (b) halogen, $C_{1-3}$-alkyl, —OH, —CN, —O—$C_{1-3}$-alkyl, —$NR^{4.1.1.1}R^{4.1.1.2}$, —S—$C_{1-3}$-alkyl, —$NR^{4.1.1.1}$—C(O)—$C_{1-3}$-alkyl, —C(O)—$NR^{4.1.1.1}R^{4.1.1.2}$, —C(O)—O—$R^{4.1.1.3}$, or (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.1}$ denotes H, or $C_{1-3}$-alkyl, $R^{4.1.1.2}$ denotes H, or $C_{1-3}$-alkyl, or $R^{4.1.1.1}$ and $R^{4.1.1.2}$ together with the nitrogen atom to which they are bound also denote a group selected from morpholinyl, thiomorpholinyl, piperidinyl, piperazinyl, pyrrolidinyl and azetidinyl, $R^{4.1.1.3}$ denotes H, or $C_{1-3}$-alkyl, $R^{4.1.2}$ denotes (a) H, (b) halogen, $C_{1-3}$-alkyl, —OH, —O—$C_{1-3}$-alkyl, or (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ independently of one another denote (a) H, (b) halogen, $C_{1-3}$-alkyl, —OH, —CN, —O—$C_{1-3}$-alkyl, —$NR^{4.2.1}R^{4.2.2}$, —S—$C_{1-3}$-alkyl, —$NR^{4.2.1}$—C(O)—$C_{1-3}$-alkyl, —C(O)—$NR^{4.2.1}R^{4.2.2}$, —C(O)—O—$R^{4.2.3}$, or (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.2.1}$ denotes H, or $C_{1-3}$-alkyl and $R^{4.2.2}$ denotes H, or $C_{1-3}$-alkyl, or $R^{4.2.1}$ and $R^{4.2.2}$ together with the nitrogen atom to which they are bound also denote a group which is selected from among morpholinyl, thiomorpholinyl, piperidinyl, piperidonyl, piperazinyl, pyrrolidinyl and azetidinyl, and which may additionally be substituted by one or two groups selected from among F, —OH, —O—$C_{1-3}$-alkyl, —$OCF_3$, $C_{1-3}$-alkyl and $CF_3$, $R^{4.2.3}$ denotes H, or $C_{1-3}$-alkyl, $R^3$ and $R^4$ together with the nitrogen atom to which they are bound denote:

(a) a saturated 5-, 6-, 7- or 9-membered heterocyclic group, which is substituted at a carbon atom by a group $R^{4.3}$ or by two groups $R^{4.3}$ and $R^{4.4}$, (b) a saturated 5-, 6- or 7-membered heterocyclic group, which is substituted at two adjacent carbon atoms by in each case a group $R^{4.3}$ and $R^{4.4}$, (c) a saturated 5-, 6- or 7-membered heterocyclic group which is substituted at a carbon atom by a group $R^{4.3}$ or by two groups $R^{4.3}$ and $R^{4.4}$ and is additionally fused to a 5-, 6- or 7-membered cycloalkyl- or heterocyclyl group, wherein the fused-on cycloalkyl or heterocyclyl group is substituted by 1, 2 or 3 groups $R^{4.5}$, (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$, (e) a monounsaturated 5-, 6- or 7-membered heterocyclic group, which is substituted at a carbon atom a group $R^{4.3}$ or by two groups $R^{4.3}$ and $R^{4.4}$ and is additionally fused to a 5- or 6-membered heteroaryl group, wherein the fused-on heteroaryl group is substituted by 1, 2 or 3 groups $R^{4.5}$, or (f) a heteroaryl group which is substituted by a group $R^{4.5}$ at 1, 2 or 3 carbon atoms, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O)—, —$NH_2$, ($C_{1-4}$-alkyl)—NH—, ($C_{1-4}$-alkyl)$_2$N—, or heterocyclyl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl, $C_{5-6}$-cycloalkenyl or heterocyclyl group, $R^{4.3}$ independently of one another denote (a) H, (b) halogen, $C_{1-3}$-alkyl, —OH, —O—$C_{1-3}$-alkyl, —$NH_2$, —CN, —C(O)—O—$R^{4.5.1}$, —C(O)—$NR^{4.5.2}R^{4.5.3}$, (c) a $C_{1-3}$-alkyl- or —O—$C_{1-3}$-alkyl group, wherein each methylene group is substituted by up to two fluorine atoms and each methyl group is substituted by up to three fluorine atoms, or (d) phenyl, $R^{4.5.1}$ denotes H, or $C_{1-3}$-alkyl, $R^{4.5.2}$ denotes H, or $C_{1-3}$-alkyl and $R^{4.5.3}$ denotes H, or $C_{1-3}$-alkyl, or a tautomer or salt thereof.

9. A compound of the formula I according to claim 1, wherein $R^3$ denotes (a) H, (b) $C_{1-6}$-alkyl, (c) a $C_{3-6}$-cycloalkyl substituted by one or two groups $R^{3.2}$, or (d) a $C_{1-3}$-alkyl group, wherein each methylene group is substituted by up to two fluorine atoms and each methyl group is substituted by up to three fluorine atoms, $R^{3.2}$ independently of one another denote (a) H, (b) halogen, $C_{1-3}$-alkyl, —OH, —O—$C_{1-3}$-alkyl, or (c) a $C_{1-3}$-alkyl- or —O—$C_{1-3}$-alkyl group, wherein each methylene group is substituted by up to two fluorine atoms and each methyl group is substituted by up to three fluorine atoms, $R^4$ denotes
- (a) H,
- (b) $C_{1-6}$-alkylene-$R^{4.1}$,
- (c) a $C_{3-6}$-cycloalkyl group substituted by one or two groups $R^{4.2}$,
- (d) a $C_{5-7}$-cycloalkenyl group substituted by one or two groups $R^{4.2}$,
- (e) an aryl group substituted by one or two groups $R^{4.2}$ or
- (f) a $C_{5-6}$-cycloalkyl group, which may be fused to a phenyl group and which is additionally substituted by one or two groups $R^{4.2}$, $R^{4.1}$ denotes
- (a) H or
- (b) a phenyl group substituted by the groups $R^{4.1.1}$ and $R^{4.1.2}$, $R^{4.1.1}$ denotes
- (a) H,
- (b) halogen, $C_{1-3}$-alkyl, —OH, —O—$C_{1-3}$-alkyl, —CN, —C(O)—O—$R^{4.1.1.3}$, or
- (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.3}$ denotes H, or $C_{1-3}$-alkyl, $R^{4.1.2}$ denotes
- (a) H,
- (b) halogen, $C_{1-3}$-alkyl, —OH, —O—$C_{1-3}$-alkyl, or
- (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ independently of one another denote
- (a) H,
- (b) halogen, $C_{1-3}$-alkyl, —OH, —O—$C_{1-3}$-alkyl, —CN, —O—C(O)—$C_{1-3}$-alkyl, or
- (c) a $C_{1-3}$-alkyl- or —O—$C_{1-3}$-alkyl group, wherein each methylene group is substituted by up to two fluorine atoms and each methyl group is substituted by up to three fluorine atoms, $R^3$ and $R^4$ together with the nitrogen atom to which they are bound denote:
- (a) a saturated 5- or 6-membered heterocyclic group, which is substituted at a carbon atom by a group $R^{4.3}$ or by two groups $R^{4.3}$ and $R^{4.4}$,
- (b) a saturated 5- or 6-membered heterocyclic group, which is substituted at two adjacent carbon atoms by a group $R^{4.3}$ and $R^{4.4}$ in each case,
- (c) a saturated 5-, 6- or 7-membered heterocyclic group, which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, wherein the fused-on cycloalkyl or heterocyclyl group is substituted by 1, 2 or 3 groups $R^{4.5}$,
- (d) a monounsaturated 5-, 6- or 7-membered heterocyclic group, which is substituted at a carbon atom by a group $R^{4.3}$ or by two groups $R^{4.3}$ and $R^{4.4}$ and is additionally fused to a phenyl group, wherein the fused-on phenyl group is substituted by 1, 2 or 3 groups $R^{4.5}$,
- (e) a monounsaturated 5-, 6- or 7-membered heterocyclic group, which is substituted at a carbon atom by a group $R^{4.3}$ or by two groups $R^{4.3}$ and $R^{4.4}$ and is additionally fused to a 5- or 6-membered heteroaryl group, wherein the fused-on heteroaryl group is substituted by 1, 2 or 3 groups $R^{4.5}$ and is selected from among

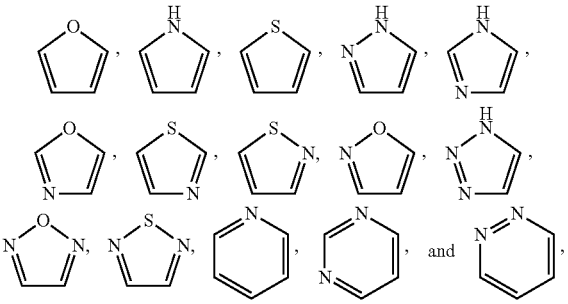

or
- (f) a heteroaryl group, which is substituted in each case by a group $R^{4.5}$ at 1, 2 or 3 carbon atoms, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O)—, —$NH_2$, ($C_{1-4}$-alkyl)—NH—, ($C_{1-4}$-alkyl)$_2$N—, morpholinyl, thiomorpholinyl, piperidinyl, pyrrolidinyl, or azetidinyl, $R^{4.4}$ denotes
- (a) H, $C_{1-3}$-alkyl, —OH, —O—$C_{1-3}$-alkyl, or
- (b) a $C_{1-3}$-alkyl- or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl or heterocyclyl group, and $R^{4.5}$ independently of one another denote
- (a) H,
- (b) halogen, $C_{1-3}$-alkyl, —OH, —O—$C_{1-3}$-alkyl, —$NH_2$, —CN,
- (c) a $C_{1-3}$-alkyl- or —O—$C_{1-3}$-alkyl group, wherein each methylene group is substituted by up to two fluorine atoms and each methyl group is substituted by up to three fluorine atoms, or
- (d) phenyl, or a tautomer or salt thereof.

10. A compound of the formula I according to claim 1, wherein $R^3$ denotes
- (a) H,
- (b) $C_{1-6}$-alkyl,
- (c) a $C_{3-6}$-cycloalkyl group substituted by one or two groups $R^{3.2}$ or
- (d) a $C_{1-3}$-alkyl group, wherein each methylene group is substituted by up to two fluorine atoms and each methyl group is substituted by up to three fluorine atoms, $R^{3.2}$ independently of one another denote
- (a) H,
- (b) halogen, $C_{1-3}$-alkyl, —OH, —O—$C_{1-3}$-alkyl, or
- (c) a $C_{1-3}$-alkyl- or —O—$C_{1-3}$-alkyl group, wherein each methylene group is substituted by up to two fluorine atoms and each methyl group is substituted by up to three fluorine atoms, $R^4$ denotes
- (a) H,
- (b) $C_{1-6}$-alkylene-$R^{4.1}$,
- (c) a $C_{3-6}$-cycloalkyl group substituted by one or two groups $R^{4.2}$,
- (d) a $C_{5-7}$-cycloalkenyl group substituted by one or two groups $R^{4.2}$, (e) a phenyl group substituted by one or two groups $R^{4.2}$ or (f) a $C_{5-6}$-cycloalkyl group, which may be fused to a phenyl group and is additionally substituted by one or two groups $R^{4.2}$, $R^{4.1}$ denotes (a) H or (b) a phenyl group substituted by the groups $R^{4.1.1}$ and $R^{4.1.2}$, $R^{4.1.1}$ denotes (a) H, (b) halogen, $C_{1-3}$-alkyl, —OH, —O—$C_{1-3}$-alkyl, —CN, —C(O)—O—$R^{4.1.1.3}$, or (c) a $C_{1-3}$-alkyl- or —O—$C_{1-3}$-alkyl group, wherein each methylene group is substituted by up to two fluorine atoms and each methyl group is substituted by up to three fluorine atoms, $R^{4.1.1.3}$ denotes H, or $C_{1-3}$-alkyl, $R^{4.1.2}$ denotes (a) H, (b) halogen, $C_{1-3}$-alkyl, —OH, —O—$C_{1-3}$-alkyl, or (c) a $C_{1-3}$-alkyl- or —O—$C_{1-3}$-alkyl group, wherein each methylene group is substituted by up to two fluorine atoms and each methyl group is substituted by up to three fluorine atoms, or $R^{4.2}$ denotes (a) H, (b) halogen, $C_{1-3}$-alkyl, —OH, —O—$C_{1-3}$-alkyl, —CN, or (c) a $C_{1-3}$-alkyl- or —O—$C_{1-3}$-alkyl group, wherein each methylene group is substituted by up to two fluorine atoms and each methyl group is substituted by up to three fluorine atoms, or $R^3$ and $R^4$ together with the nitrogen atom to which they are bound denote:

(a) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at a carbon atom by a group $R^{4.3}$ or by two groups $R^{4.3}$ and $R^{4.4}$, (b) a saturated 5- or 6-membered heterocyclic group, which is selected from among piperidinyl, piperidinonyl, morpholinyl, thiomorpholinyl, piperazinyl, pyrrolidinyl and pyrrolidinonyl, and which is substituted at two adjacent carbon atoms by a group $R^{4.3}$ and $R^{4.4}$ in each case, (c) a saturated 5-, 6- or 7-membered heterocyclic group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, and which is substituted at a carbon atom by a group $R^{4.3}$ or by two groups $R^{4.3}$ and $R^{4.4}$ and is additionally fused to a 5-, 6- or 7-membered cycloalkyl or heterocyclyl group, which is selected from among piperidinyl, piperidinonyl, morpholinyl, thiomorpholinyl, piperazinyl, pyrrolidinyl, pyrrolidinonyl, azepanyl, diazepanyl, diazepanonyl and oxazepanyl, wherein the fused-on cycloalkyl or heterocyclyl group is substituted by 1, 2 or 3 groups $R^{4.5}$, (d) a monounsaturated 5-, 6- or 7-membered heterocyclic group, which is selected from among

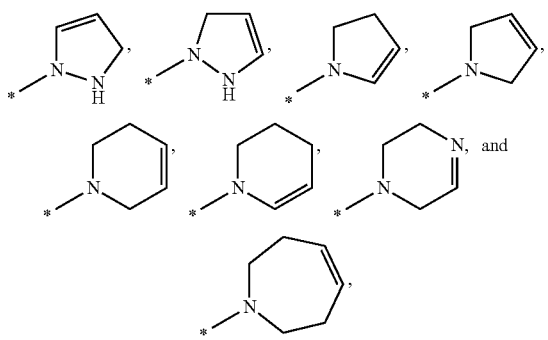

and which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, (e) a monounsaturated 5-, 6- or 7-membered heterocyclic group, which is selected from among

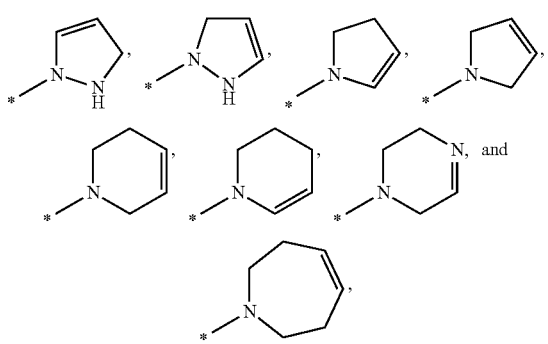

and which is substituted at a carbon atom by a group $R^{4.3}$ or by two groups $R^{4.3}$ and $R^{4.4}$ and is additionally fused to a 5- or 6-membered heteroaryl group, while the fused-on heteroaryl group is substituted by 1, 2 or 3 groups $R^{4.3}$ and is selected from among

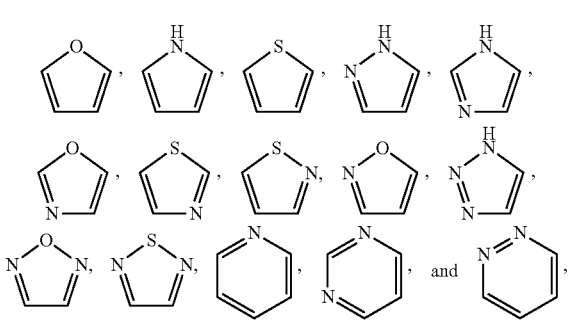

or (f) a heteroaryl group, which is selected from among indole, isoindole, azaindole, indazole and benzimidazole, and which is substituted by a group $R^{4.5}$ at 1, 2 or 3 carbon atoms, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O)—, —$NH_2$, ($C_{1-4}$-alkyl)—NH—, ($C_{1-4}$-alkyl)$_2$N—, morpholinyl, thiomorpholinyl, piperidinyl, pyrrolidinyl, or azetidinyl, $R^{4.4}$ denotes
(a) H, $C_{1-3}$-alkyl, —OH, —O—$C_{1-3}$-alkyl or
(b) a $C_{1-3}$-alkyl or —O—$C_{1-3}$-alkyl group, wherein each methylene group is substituted by up to two fluorine atoms and each methyl group is substituted by up to three fluorine atoms, $R^{4.3}$ and $R^{4.4}$ together with the carbon atoms to which they are bound also denote a $C_{3-6}$-cycloalkyl group or a heterocyclyl group which is selected from among azetidinyl, pyrrolidinyl, piperidinyl and azepanyl, and $R^{4.5}$ independently of one another denote
(a) H,
(b) halogen, $C_{1-3}$-alkyl, —OH, —O—$C_{1-3}$-alkyl, —$NH_2$, —CN,
(c) a $C_{1-3}$-alkyl or —O—$C_{1-3}$-alkyl group, wherein each methylene group is substituted by up to two fluorine atoms and each methyl group is substituted by up to three fluorine atoms, or
(d) phenyl, or a tautomer or salt thereof.

11. A compound of the formula I according to claim 1, wherein $R^3$ denotes
(a) H,
(b) $C_{1-3}$-alkyl or
(c) a $C_{1-3}$-alkyl group, wherein each methylene group is substituted by up to two fluorine atoms and each methyl group is substituted by up to three fluorine atoms, and $R^4$ denotes H, cyclopropyl or a group selected from

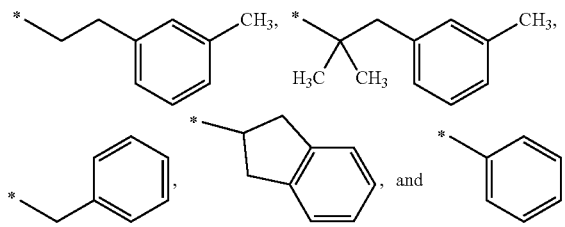

$R^3$ and $R^4$ together with the nitrogen atom to which they are attached denote a group selected from

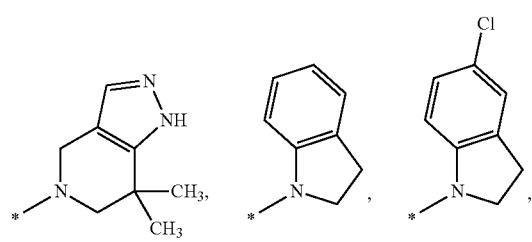

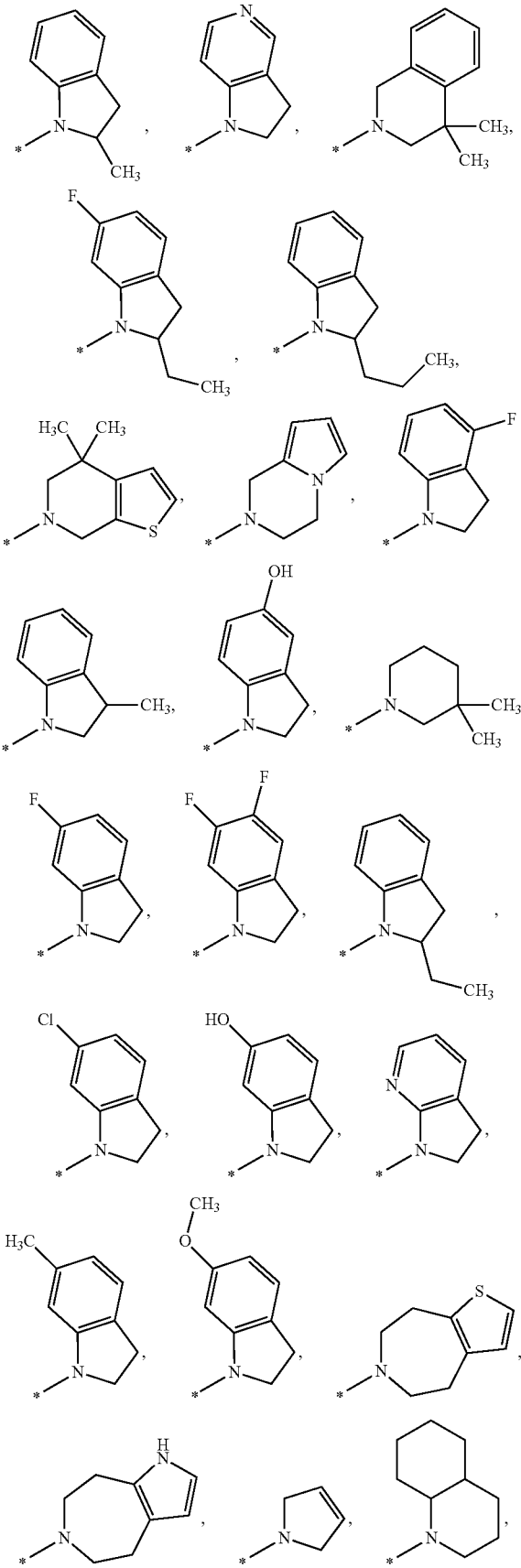

or a tautomer or salt thereof.

12. A compound of the formula I according to claim 1, wherein $R^3$ and $R^4$ together with the nitrogen atom to which they are attached denote a monounsaturated 5-membered heterocyclic group which is substituted at a carbon atom by a group $R^{4.3}$ or by two groups $R^{4.3}$ and $R^{4.4}$ and is additionally fused to a phenyl group, while the fused-on phenyl group is substituted by 1, 2 or 3 groups $R^{4.5}$, $R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O)—, —$NH_2$, ($C_{1-4}$-alkyl)—NH—, ($C_{1-4}$-alkyl)$_2$N—, morpholinyl, thiomorpholinyl, piperidinyl, pyrrolidinyl, or azetidinyl, $R^{4.4}$ denotes (a) H, $C_{1-3}$-alkyl, —OH, —O—$C_{1-3}$-alkyl or (b) a $C_{1-3}$-alkyl or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denote (a) H, (b) halogen, $C_{1-3}$-alkyl, —OH, —O—$C_{1-3}$-alkyl, —$NH_2$, —CN, (c) a $C_{1-3}$-alkyl- or —O—$C_{1-3}$-alkyl group wherein each methylene group is substituted by up to two fluorine atoms and each methyl group is substituted by up to three fluorine atoms, or (d) phenyl, or a tautomer or salt thereof.

13. A compound of the formula I according to claim 1, wherein $R^3$ and $R^4$ together with the nitrogen atom to which they are attached denote a group of the formula IVa or IVb (IVa)

(IVb)

$R^{4.3}$ denotes H, $C_{1-3}$-alkyl, phenyl, —$C_{1-3}$-alkylene-$R^{4.3.1}$, $C_{1-3}$-alkyl-O—C(O)—, HO—C(O)—, F, —O—$C_{1-3}$-alkyl, —OH, or —CN, $R^{4.3.1}$ denotes H, $C_{1-3}$-alkyl-O—C(O)—, —$NH_2$, ($C_{1-4}$-alkyl)—NH—, ($C_{1-4}$-alkyl)$_2$N—, morpholinyl, thiomorpholinyl, piperidinyl, pyrrolidinyl, or azetidinyl, $R^{4.4}$ denotes (a) H, $C_{1-3}$-alkyl, —OH, —O—$C_{1-3}$-alkyl or (b) a $C_{1-3}$-alkyl- or —O—$C_{1-3}$-alkyl group wherein each methylene group is substituted by up to two fluorine atoms and each methyl group is substituted by up to three fluorine atoms, or $R^{4.3}$ and $R^{4.4}$ together with the carbon atom to which they are attached also denote a $C_{3-6}$-cycloalkyl group or a heterocyclyl group which is selected from among azetidinyl, pyrrolidinyl, piperidinyl and azepanyl, and $R^{4.5}$ independently of one another denote (a) H, (b) halogen, $C_{1-3}$-alkyl, —OH, —O—$C_{1-3}$-alkyl, —$NH_2$, —CN, $NO_2$, (c) a $C_{1-3}$-alkyl or —O—$C_{1-3}$-alkyl group wherein each methylene group is substituted by up to two fluorine atoms and each methyl group is substituted by up to three fluorine atoms, or (d) phenyl, or a tautomer or salt thereof.

14. A compound of the formula I according to claim 1, wherein $R^3$ and $R^4$ together with the nitrogen atom to which they are attached denote a group selected from

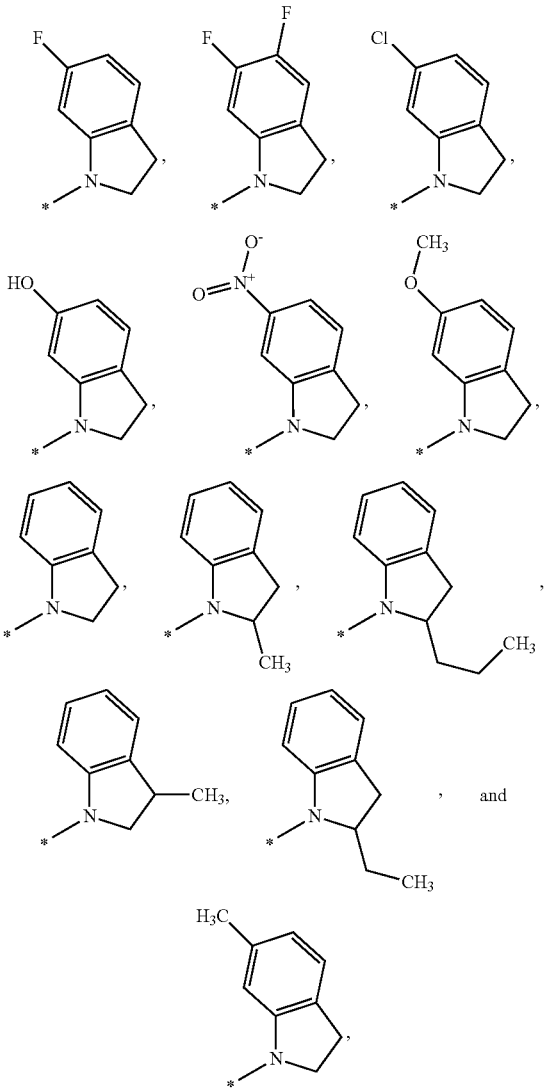

or a tautomer or salt thereof.

15. A compound of the formula I according to claim 1, wherein

R¹ denotes

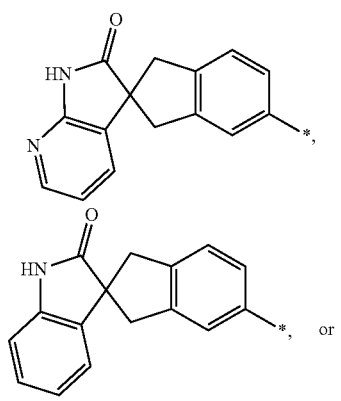

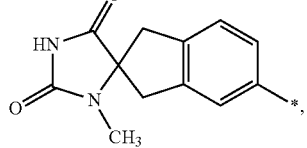

R² denotes H,

R³ denotes (a) H, (b) $C_{1-3}$-alkyl or (c) a $C_{1-3}$-alkyl group wherein each methylene group is substituted by up to two fluorine atoms and each methyl group is substituted by up to three fluorine atoms, and R⁴ denotes H, cyclopropyl or a group selected from

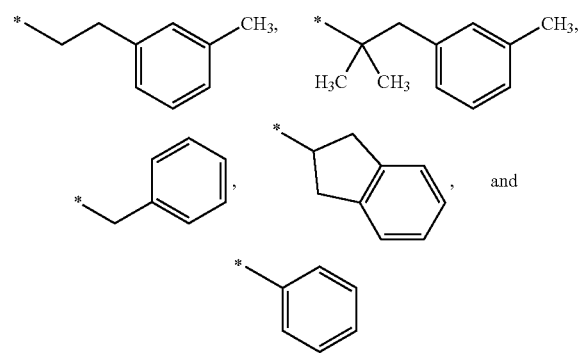

or

R³ and R⁴ together with the nitrogen atom to which they are attached denote a group selected from

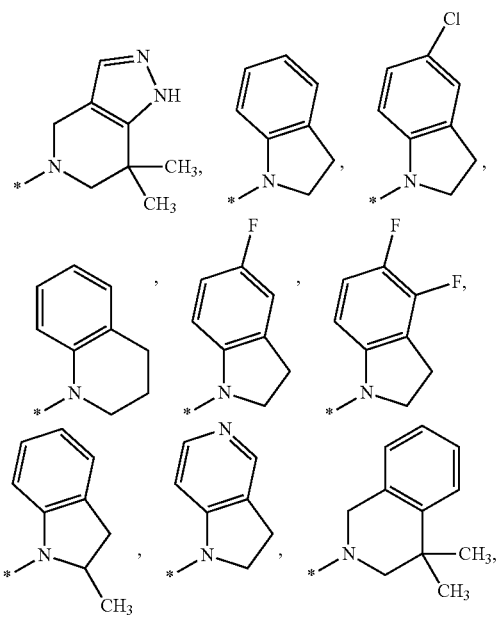

-continued
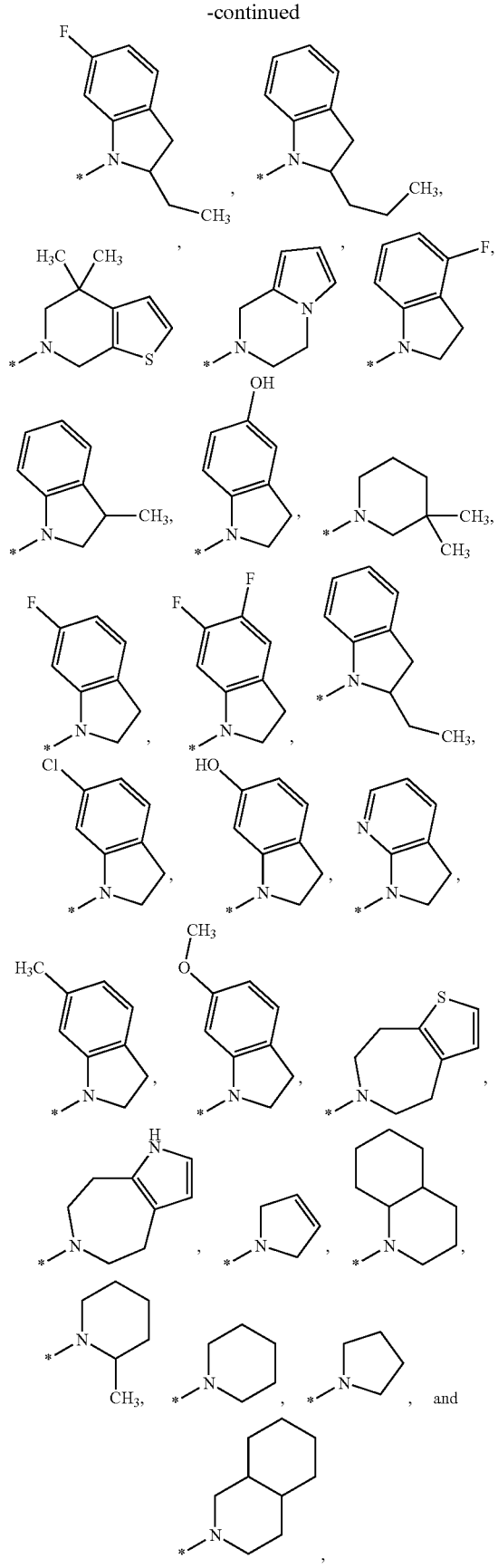
and the ring
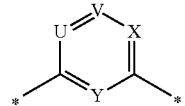
denotes a group selected from
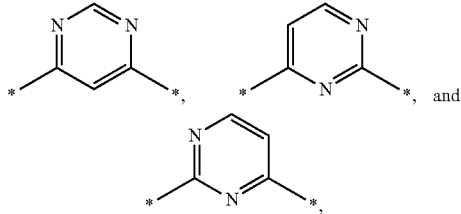
or a tautomer or salt thereof.
16. A compound of the formula I according to claim 1, wherein
R¹ and R² together with the nitrogen atom to which they are attached denote a group selected from
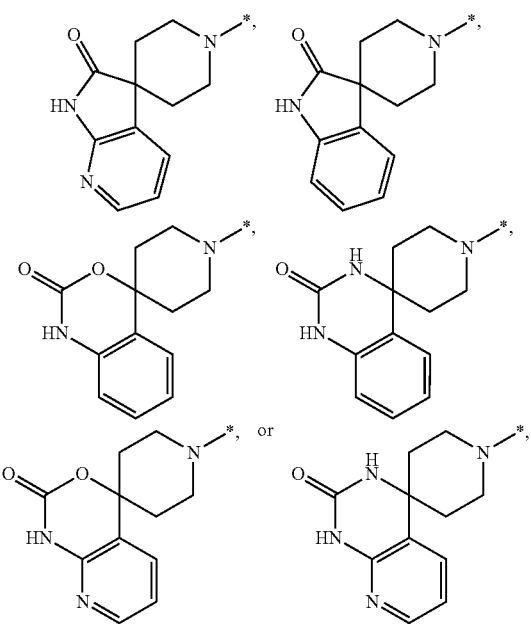
R³ and R⁴ together with the nitrogen atom to which they are attached denote a group selected from
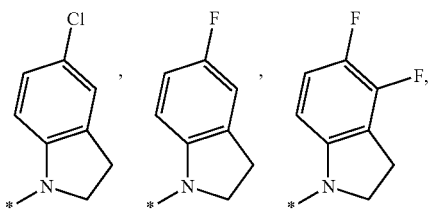

-continued
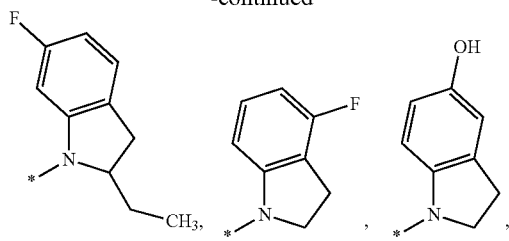
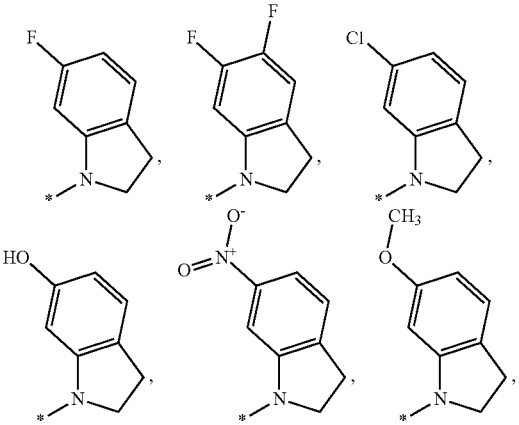
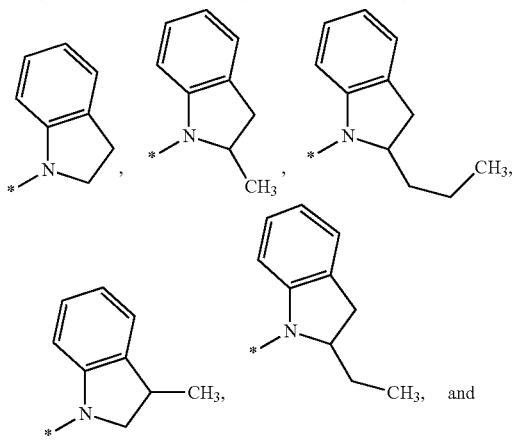, and
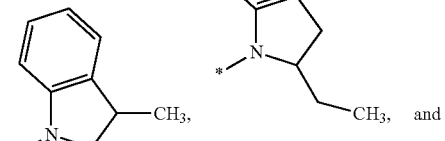
-continued
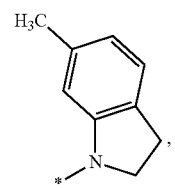
and the ring
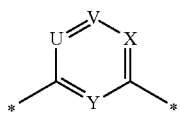
denote a group selected from
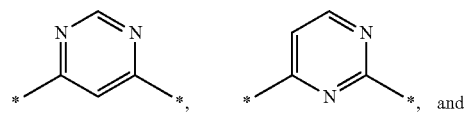
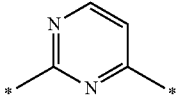
or a tautomer or salt thereof.
17. A compound of according to claim 1 selected from the group consisting of:
| No. | Structure |
|---|---|
| (1) | 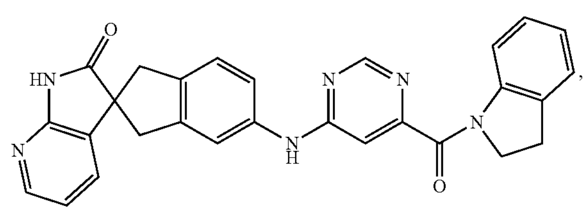 |
| (2) | 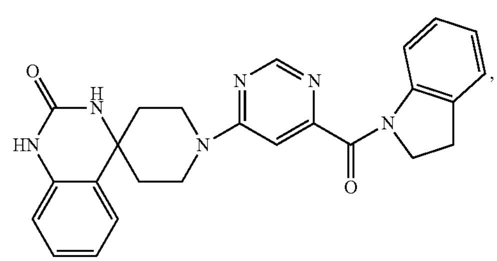 |

-continued
| No. | Structure |
|---|---|
| (3) | 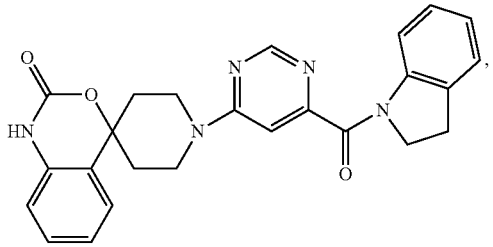 |
| (4) | 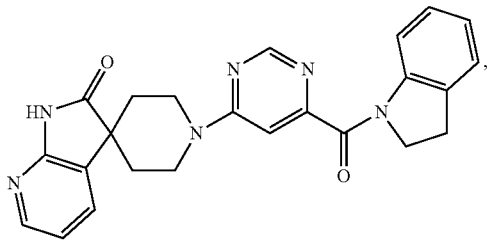 |
| (5) | 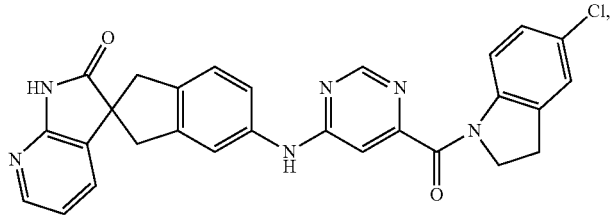 |
| (6) | 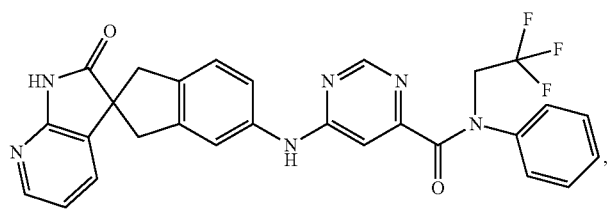 |
| (7) | 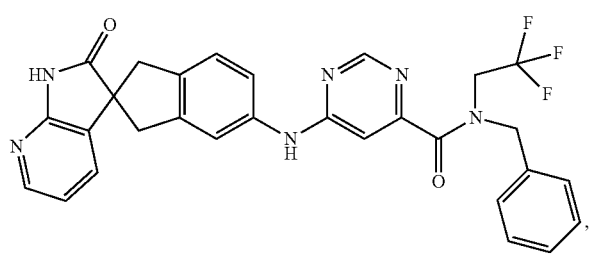 |
| (8) | 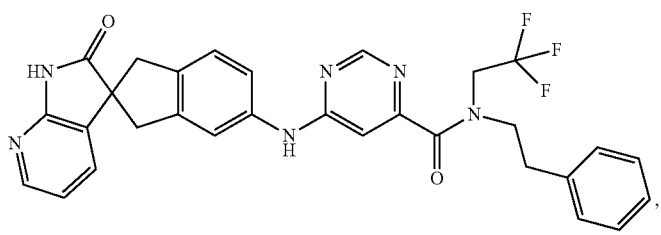 |

-continued
| No. | Structure |
|---|---|
| (9) | 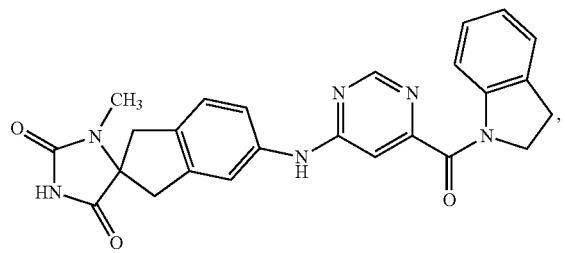 |
| (10) | 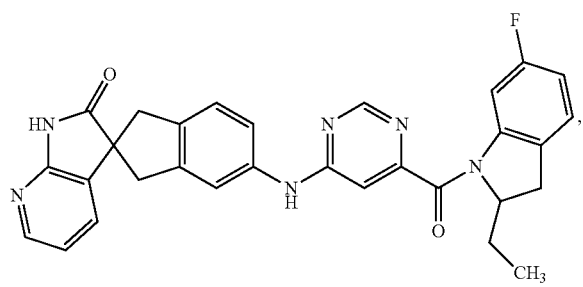 |
| (11) | 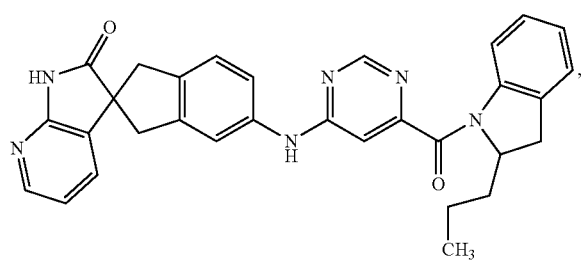 |
| (12) | 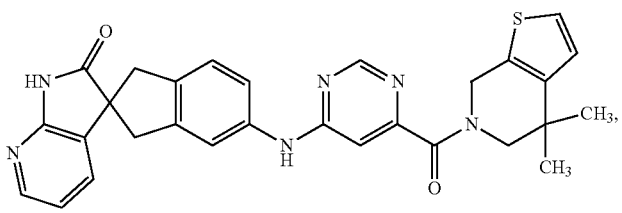 |
| (13) | 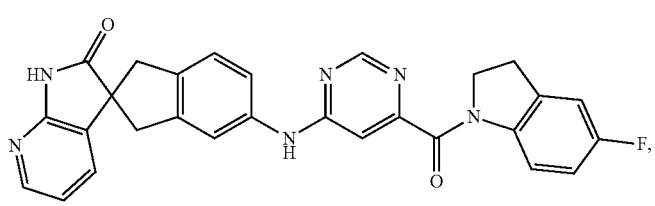 |
| (14) | 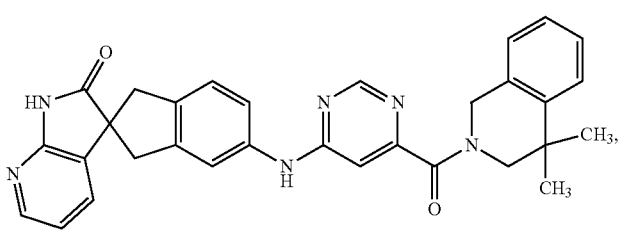 |

-continued

| No. | Structure |
|---|---|
| (15) | 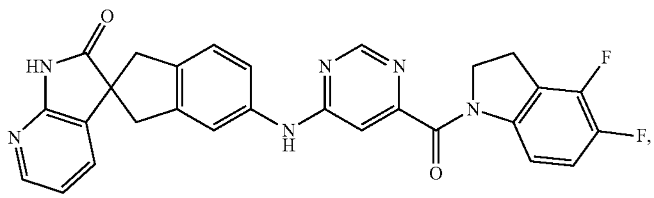 |
| (16) | 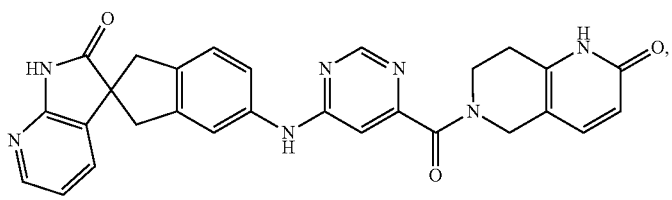 |
| (17) | 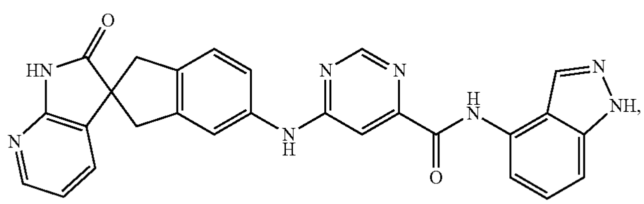 |
| (18) | 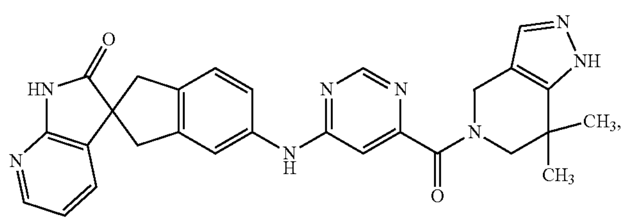 |
| (19) | 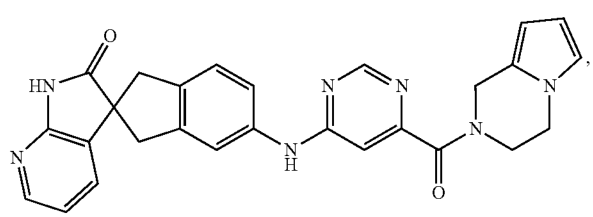 |
| (32) | 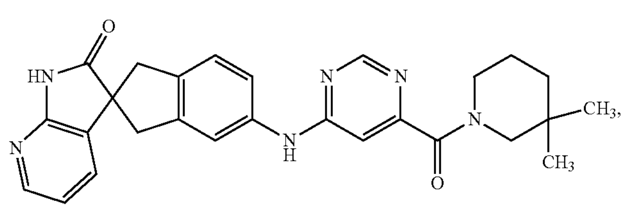 |
| (33) | 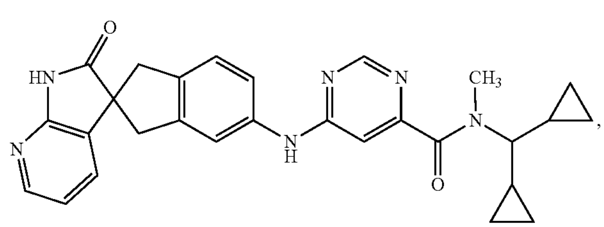 |

| No. | Structure |
|---|---|
| (34) | 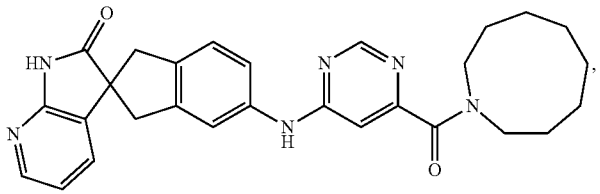 |
| (35) | 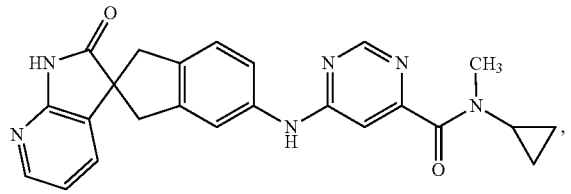 |
| (36) | 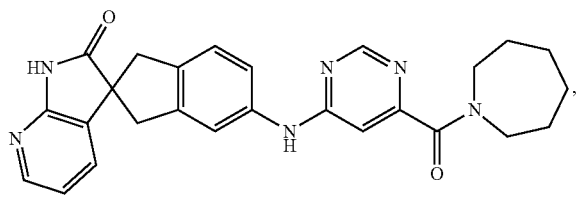 |
| (37) | 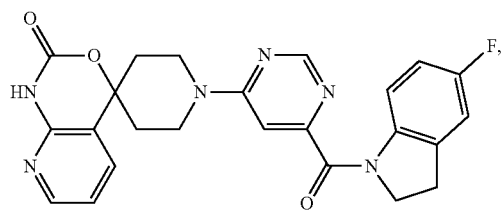 |
| (38) | 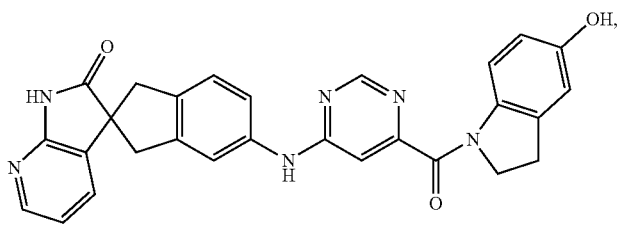 |
| (39) | 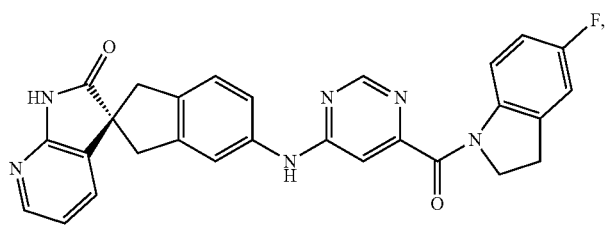 |
| (40) | 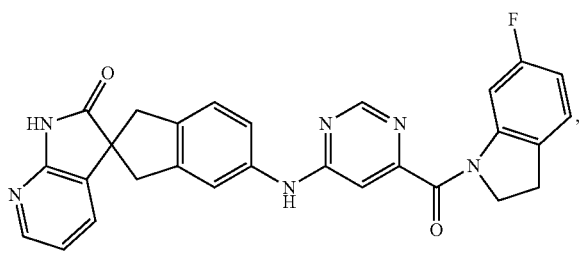 |

| No. | Structure |
|---|---|
| (41) | 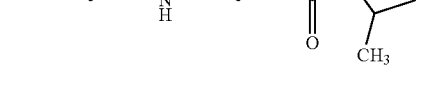 |
| (43) | 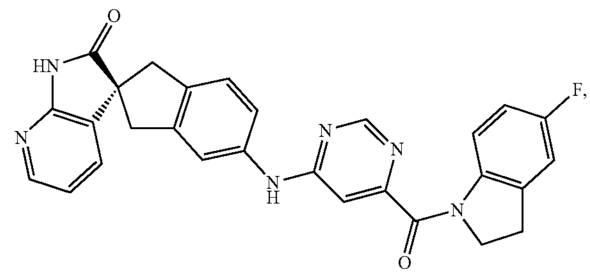 |
| (44) | 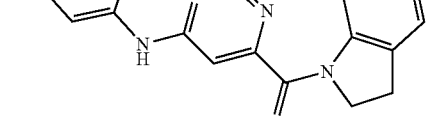 |
| (45) | 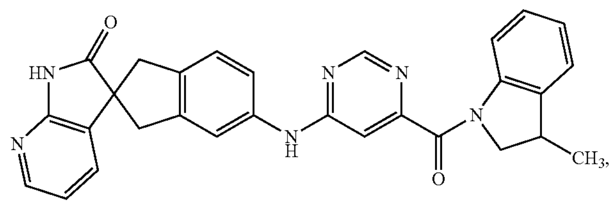 |
| (46) | 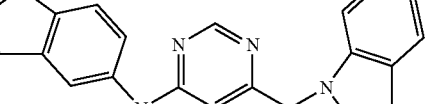 |
| (47) | 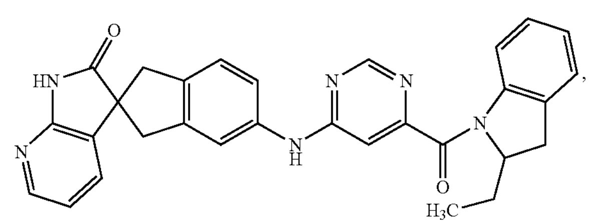 |
| (48) | 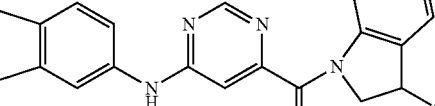 |

| No. | Structure |
|---|---|
| (49) | 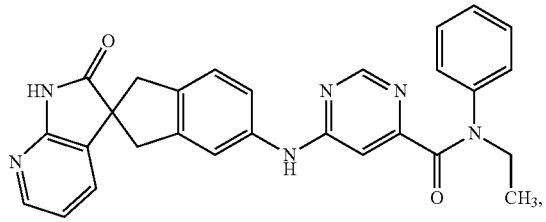 |
| (50) | 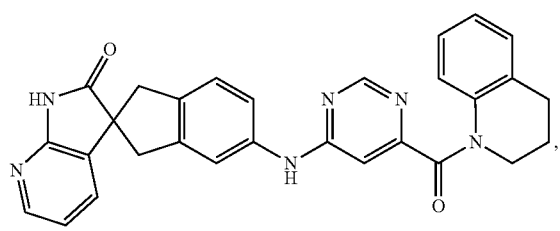 |
| (51) | 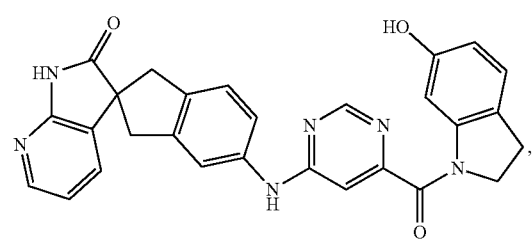 |
| (52) | 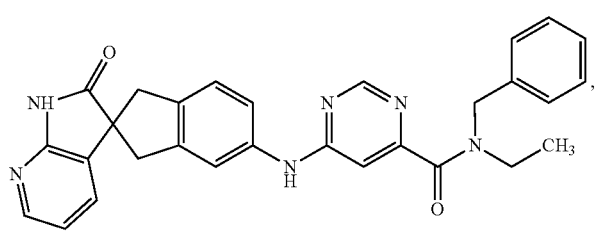 |
| (55) | 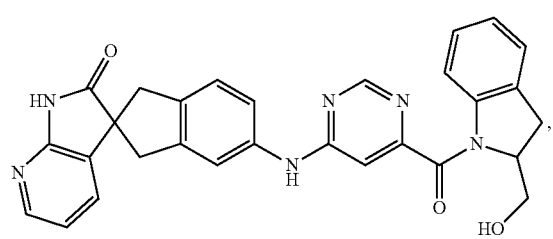 |
| (56) | 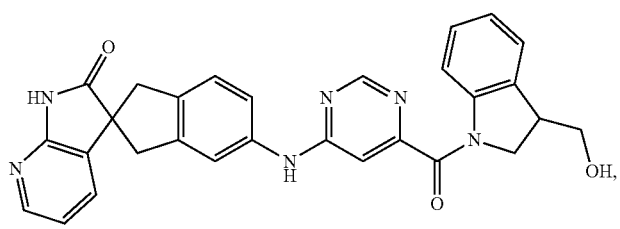 |

-continued
| No. | Structure |
|---|---|
| (57) | 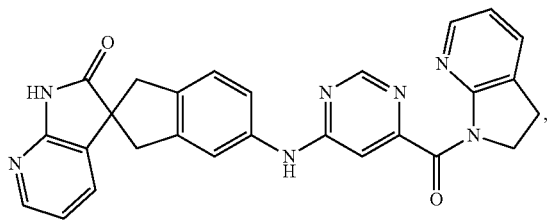 |
| (58) | 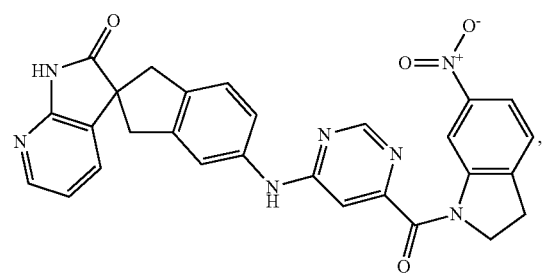 |
| (59) | 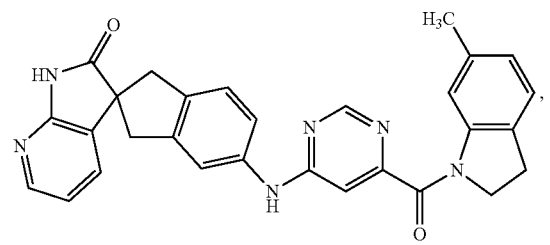 |
| (60) | 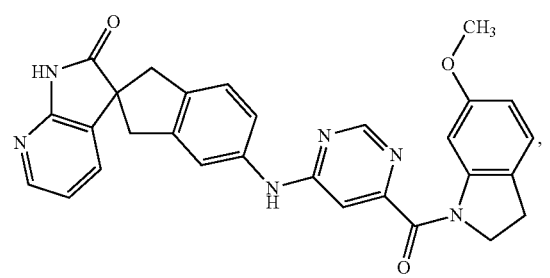 |
| (61) | 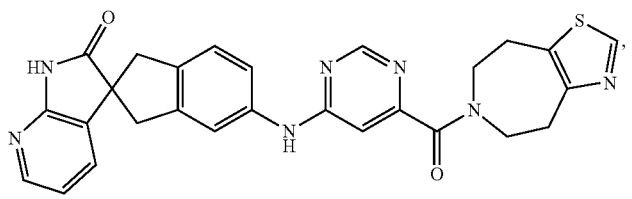 |
| (62) | 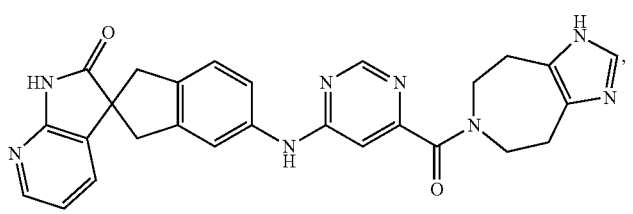 |

| No. | Structure |
|---|---|
| (63) | 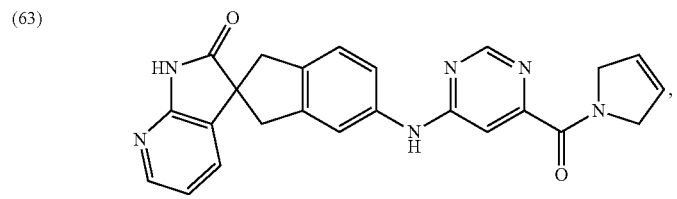 |
| (64) | 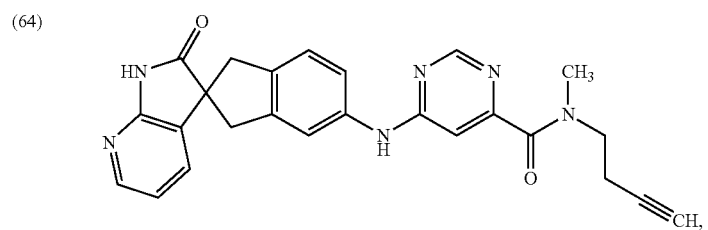 |
| (65) | 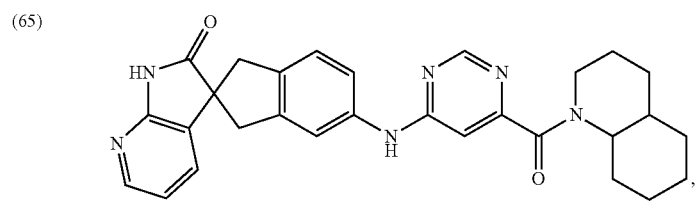 |
| (66) | 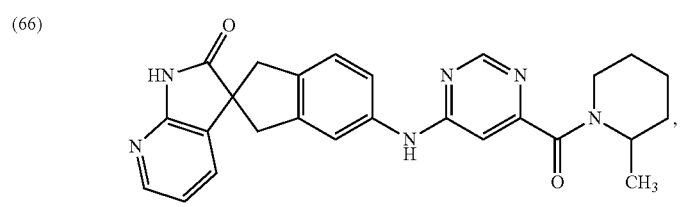 |
| (67) | 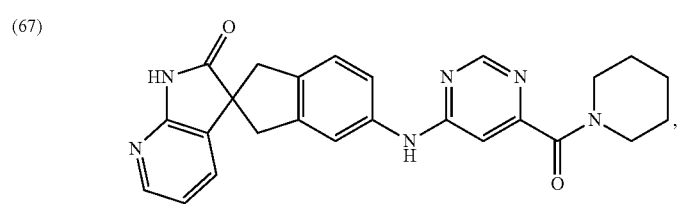 |
| (68) | 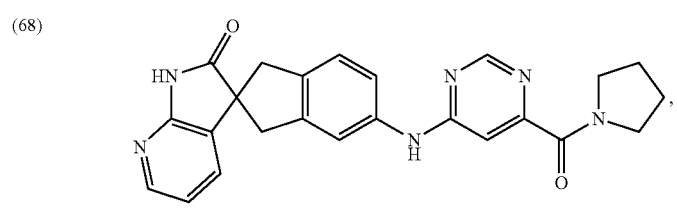 |
| (69) | 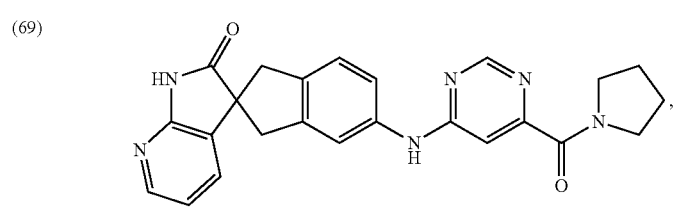 |

| No. | Structure |
|---|---|
| (70) | 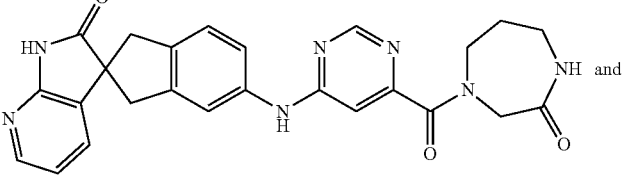 and |
| (71) | 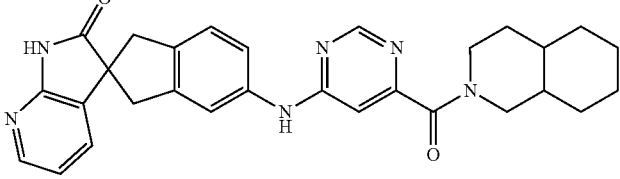 | or a salt thereof.

18. A physiologically acceptable salt of a compound according to any one of claims 1 to 14 and 15 to 17.

19. A pharmaceutical composition comprising a compound according to any one of claim 1 to 14 and 15 to 17, or a physiologically acceptable salt thereof, and a carrier or diluent.

20. A method of treating tension, migraine or cluster headache which comprises administering to a host in need of such treatment a therapeutically effective amount of a compound according to any one of claim 1 to 14 and 15 to 17, or a physiologically acceptable salt thereof.

* * * * *